(12) United States Patent
Klaerner et al.

(10) Patent No.: US 6,833,276 B2
(45) Date of Patent: *Dec. 21, 2004

(54) POLYMER BRUSHES FOR IMMOBILIZING MOLECULES TO A SURFACE AND HAVING WATER-SOLUBLE OR WATER-DISPERSIBLE SEGMENTS THEREIN AND PROBES BONDED THERETO

(75) Inventors: Gerrit Klaerner, Campbell, CA (US); Ralph B. Nielsen, San Jose, CA (US); Paul Mansky, San Francisco, CA (US); Didier Benoit, San Jose, CA (US); Dominique Charmot, Los Gatos, CA (US); Bernd Jandeleit, Sunnyvale, CA (US); Laura T. Mazzola, Redwood City, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 37 days.

This patent is subject to a terminal disclaimer.

(21) Appl. No.: 09/911,683

(22) Filed: Jul. 24, 2001

(65) Prior Publication Data

US 2002/0001845 A1 Jan. 3, 2002

Related U.S. Application Data

(63) Continuation of application No. 09/609,461, filed on Jul. 30, 2000, now Pat. No. 6,692,914, which is a continuation-in-part of application No. 09/347,606, filed on Jul. 2, 1999, now abandoned, and a continuation-in-part of application No. 09/347,607, filed on Jul. 2, 1999, now abandoned, and a continuation-in-part of application No. 09/347,608, filed on Jul. 2, 1999, now abandoned, and a continuation-in-part of application No. 09/347,609, filed on Jul. 2, 1999, now Pat. No. 6,472,486.

(60) Provisional application No. 60/146,936, filed on Jul. 31, 1999, and provisional application No. 60/177,879, filed on Jan. 24, 2000.

(51) Int. Cl.[7] ................... G01N 33/545; G01N 33/546; G01N 33/552; G01N 33/533; C12Q 1/68; C07K 17/06; C07K 17/08

(52) U.S. Cl. ................... 436/532; 436/531; 436/527; 436/546; 435/6; 530/408; 530/409; 530/391.1

(58) Field of Search .................... 436/532, 531, 436/527, 546; 435/6; 530/408, 409, 391.1

(56) References Cited

U.S. PATENT DOCUMENTS

| | | | |
|---|---|---|---|
| 4,581,429 A | 4/1986 | Solomon et al. |
| 4,946,778 A | 8/1990 | Ladner et al. |
| 4,973,493 A | 11/1990 | Guire |
| 5,002,582 A | 3/1991 | Guire et al. |
| 5,030,697 A | 7/1991 | Hugl et al. |
| 5,126,021 A | 6/1992 | Grossman |
| 5,143,854 A | 9/1992 | Pirrung et al. |
| 5,217,492 A | 6/1993 | Guire et al. |
| 5,240,602 A | 8/1993 | Hammen |
| 5,258,454 A | 11/1993 | Berg et al. |
| 5,424,186 A | 6/1995 | Fodor et al. |
| 5,436,327 A | 7/1995 | Southern et al. |
| 5,445,934 A | 8/1995 | Fodor et al. |
| 5,480,723 A | 1/1996 | Klainer et al. |
| 5,512,329 A | 4/1996 | Guire et al. |
| 5,512,439 A | 4/1996 | Hornes et al. |
| 5,530,079 A | 6/1996 | Veregin et al. |
| 5,539,082 A | 7/1996 | Nielsen et al. |
| 5,624,711 A | 4/1997 | Sundberg et al. |
| 5,677,195 A | 10/1997 | Winkler et al. |
| 5,700,637 A | 12/1997 | Southern |
| 5,744,305 A | 4/1998 | Fodor et al. |
| 5,753,439 A | 5/1998 | Smith et al. |

(List continued on next page.)

FOREIGN PATENT DOCUMENTS

| | | |
|---|---|---|
| EP | 0 205 232 A1 | 12/1986 |
| EP | 0 361 229 A2 | 7/1991 |
| EP | 0 780 408 A2 | 2/1999 |
| EP | 1 035 218 A1 | 9/2000 |
| EP | 1 081 163 A1 | 3/2001 |
| EP | 1 095 711 A2 | 5/2001 |
| WO | WO 89/02449 A1 | 3/1989 |
| WO | WO 90/05303 A1 | 5/1990 |
| WO | WO 96/00251 A1 | 1/1996 |
| WO | WO 96/24620 A1 | 8/1996 |
| WO | WO 97/41425 A1 | 11/1997 |
| WO | WO 98/30601 A2 | 7/1998 |
| WO | WO 99/03894 A1 | 1/1999 |
| WO | WO 99/06425 A1 | 2/1999 |
| WO | WO 99/36571 A2 | 7/1999 |
| WO | WO 99/61653 A2 | 12/1999 |
| WO | WO 00/33078 A1 | 6/2000 |
| WO | WO 00/33084 A2 | 6/2000 |
| WO | WO 00/43539 A2 | 7/2000 |
| WO | WO 00/65352 A1 | 11/2000 |

OTHER PUBLICATIONS

J. Ward et al, Proceeding of SPIE–The International Soc. for Optical Engineering (2000), 4097 (Complex Mediums), 221–228.*

(List continued on next page.)

*Primary Examiner*—Mary E. Ceperley
(74) *Attorney, Agent, or Firm*—Senniger Powers

(57) ABSTRACT

Sensors for determining the presence and concentration of bio-molecules in a biological sample are provided in the form of polymer brushes, which comprise a substrate having a surface that is modified with a water-dispersible or water-soluble polymer segment having functional groups that bind probes. The method of synthesis of such sensors preferably includes use of controlled free radical polymerization techniques, and in particular the use of an iniferter initiator, which allows for controlled architecture polymers to modify the surface of the substrate. In this manner functional groups in the polymer chain are removed from the surface, which allows for solution chemistry to be more realistically reproduced with the benefits of a solid bound probe.

14 Claims, 7 Drawing Sheets

U.S. PATENT DOCUMENTS

| | | |
|---|---|---|
| 5,770,456 A | 6/1998 | Holmes |
| 5,800,992 A | 9/1998 | Fodor et al. |
| 5,807,522 A | 9/1998 | Brown et al. |
| 5,824,473 A | 10/1998 | Meade et al. |
| 5,837,832 A | 11/1998 | Chee et al. |
| 5,843,655 A | 12/1998 | McGall |
| 5,846,724 A | 12/1998 | Bensimon et al. |
| 5,858,653 A | 1/1999 | Duran et al. |
| 5,868,938 A | 2/1999 | Bomer et al. |
| 5,872,003 A | 2/1999 | Koster |
| 5,902,723 A | 5/1999 | Dower et al. |
| 5,919,523 A | 7/1999 | Sundberg et al. |
| 5,919,626 A | 7/1999 | Shi et al. |
| 5,932,711 A | 8/1999 | Boles et al. |
| 5,942,555 A | 8/1999 | Swanson et al. |
| 5,998,140 A | 12/1999 | Dervan et al. |
| 6,004,755 A | 12/1999 | Wang |
| 6,013,440 A | 1/2000 | Lipshutz et al. |
| 6,018,041 A | 1/2000 | Drmanac et al. |
| 6,027,880 A | 2/2000 | Cronin et al. |
| 6,040,138 A | 3/2000 | Lockhart et al. |
| 6,040,193 A | 3/2000 | Winkler et al. |
| 6,043,080 A | 3/2000 | Lipshutz et al. |
| 6,045,996 A | 4/2000 | Cronin et al. |
| 6,054,270 A | 4/2000 | Southern |
| 6,057,100 A | 5/2000 | Heyneker |
| 6,077,674 A | 6/2000 | Schleifer et al. |
| 6,083,697 A | 7/2000 | Beecher et al. |
| 6,087,102 A | 7/2000 | Chenchik et al. |
| 6,087,112 A | 7/2000 | Dale |
| 6,087,186 A | 7/2000 | Cargill et al. |
| 6,100,026 A | 8/2000 | Nova et al. |

OTHER PUBLICATIONS

Ingall et al. "Surface Functionalization with Polymer and Block Copolymer Films Using Organometallic Initiators" J. Am. Chem. Soc., vol. 122, No. 32 (2000) pp. 7845–7846.

International Search Report for analogous application No. PCT/US02/00746 dated Apr. 29, 2003.

Y–C. Chang et al. "Surface Initiated Polymerization of Polyglutamate Copolymers" Abstract 304, Presented at the 209th ACS National Meeting in Anaheim, CA (Apr. 2–7, 1995).

Y–C. Chang et al. "Surface Initiated Polymerization of Polyglutamate Copolymers" American Chemical Society, Polymer Preprints, vol. 36, No. 1 (Apr. 1995).

Y–C. Chang et al. "Surface Polymerization of Poly(2–hydroxy ethyl methacrylate) for High Density DNA Arrays" Max–Planck–Institute for Polymer Research—Center on Polymer Interfaces and Macromolecular Assemblies forum, Mainz, Germany (Apr. 26–27, 1999).

Y–C. Chang et al. "Surface Polymerization of Poly(y–Alky-l–L–Glutamate) on Solid Substrates" Macromolecular Symposia, vol. 118 (1997) pp. 641–646.

Y–C. Chang Website at The Henry Samueli School of Engineering, homepage (2 pages) and Publications List (5 pages) printed Sep. 17, 2002.

Anders et al. "Surface Modification with Hydrogels via Macroinitiators for Enhanced Friction Properties of Biomaterials" J.M.S.—Pure Appl. Chem. vol. A36, Nos. 7&8 (1999) pp. 1017–1029.

Baker et al. "Structure of Polymer Brushes Under Shear Flow in a Good Solvent" Macromolecules, vol. 33, No. 4 (2000) pp. 1120–1122.

Benoit et al. "Development of a Universal Alkoxyamine for "Living" Free Radical Polymerizations" Journal of the American Chemical Society, vol. 121, No. 16 (1999) pp. 3904–3920.

Bergbreiter et al. "Meisenhemier Rearrangement and Allyl N–Oxides as a Route to Initiators for Nitroxide–Mediated "Living" Free Radical Polymerizations" Macromolecules, vol. 31, No. 18 (1998) pp. 6380–6382.

Biesalski et al. "Preparation and Characterization of a Polyelectrolyte Monolayer Covalently Attached to a Planar Solid Surface" Macromolecules, vol. 32, No. 7 (1999) pp. 2309–2316.

Boven et al. "Radical Grafting of Poly(methyl methacrylate) onto Silicon Wafers, Glass Slides and Glass Beads" Polymer Communications, vol. 32, No. 2 (1991) PP. 50–53.

Chan et al. "The Biophysics of DNA Hybridization with Immobilized Oligonucleotide Probes" Biophysical Journal, vol. 69, (1995) pp. 2243–2255.

Cheung et al. "Making and Reading Microarrays" Nature Genetics Supplement, vol. 21 (Jan. 1999) pp. 15–19.

Cole et al. "The EBV–Hybridoma Technique and Its Application to Human Lung Cancer" Monoclonal Antibodies and Cancer Therapy, Alan R. Liss, Inc. (1985) pp. 77–96.

Cote et al. "Generation of Human Monoclonal Antibodies Reactive with Cellular Antigens" Proceedings of the National Academy of Sciences vol. 80, No. 7 (Apr. 1983) pp. 2026–2030.

de Boer et al. "Living" Free Radical Photopolymerization Initiated form Surface–Grafted Iniferter Monolayers Macromolecules, vol. 33, No. 2 (2000) pp. 349–356.

Dhar et al. "Modification of Silica Surfaces Using Surface Initiated Polymerization" Abstracts of Papers, Part 2, 215th ACS National Meeting, Dallas, TX (1998) Abstract No. 147.

Fischer "The Persistent Radical Effect In "Living" Radical Polymerization" Macromolecules, vol. 30, No. 19 (1997) pp. 5666–5672.

Glazer "Phycobilisomes: Structure and Dynamics" Annual Review of Microbiology, vol. 36 (1982) pp. 173–198.

Grabarek et al. "Zero–Length Crosslinking Procedure with the Use of Active Esters" Analytical Biochemistry, vol. 185 (1990) pp. 131–135.

Harrison et al. "Reducing Substrate Pinning of Block Copolymer Microdomains with a Buffer Layer of Polymer Brushes" Macromolecules, vol. 33, No. 3 (2000) pp. 857–865.

Hawker et al. "Accurate Control of Chain Ends by a Novel "Living" Free–Radical Polymerization Process" Macromolecules, vol. 28, No. 8 (1995) pp. 2993–2995.

Hawker "Architectural Control in "Living" Free Radical Polymerizations: Preparation of Star and Graft Polymers" Angew. Chem. Int. Ed. Engl., vol. 34, No. 13/14 (1995) pp. 1456–1459.

Hawker et al. "Initiating Systems for Nitroxide–Mediated "Living" Free Radical Polymerizations: Synthesis and Evaluation" Macromolecules, vol. 29, No. 16 (1996) pp. 5245–5254.

Hawker et al. "Manipulation of Surface Properties Using Novel Grafted Copolymer Brushes and Surface Initiated Polymerization" Polymer Preprints, vol. 40, No. 2 (Aug. 1999) p. 101.

Hawker et al. "Manipulation of Surface Properties Using Novel Grafted Copolymer Brushes and Surface–Initiated Polymerization" 218th ACS National Meeting, Abstracts of Papers, Part 2, New Orleans, LA (Aug. 1999) Abstract 345–POLY.

Hawker et al. "Synthesis and Application of Functionalized Speciality Polymers Using 'Living' Free Radical Procedures" Polymer Preprints, vol. 39, No. 1 (Mar. 1998) pp. 626–627.

Hendrickson et al. "Crystal Structure of Core Streptavidin Determined from Multiwavelength Anomalous Diffraction of Synchrotron Radiation" Proceedings of the National Academy of Sciences USA, vol. 86, No. 7 (Apr. 1989) pp. 2190–2194.

Hertler et al. "Group–Transfer Polymerization on a Polymeric Support" Macromolecules, vol. 23, No. 5 (1990) pp. 1264–1268.

Higashi et al. "High–Spatioresolved Microarchitectural Surface Prepared by Photograft Copolymerization Using Dithiocarbamate: Surface Preparation and Cellular Responses" Langmuir, vol. 15, No. 6 (1999) pp. 2080–2088.

Hodges et al. "Preparation of Designer Resins via Living Free Radical Polymerization of Functional Monomers on Solid Support" J. Comb. Chem., vol. 2, No. 1 (2000) pp. 80–88.

Hosoya et al. "In Situ Surface–Selective Modification of Uniform Size Macroporous Polymer Particles with Temperature–Responsive Poly–N–isopropylacrylamide" Macromolecules, vol. 27, No. 14 (1994) pp. 3973–3976.

Huang et al. "Mixed Lamellar Films: Evolution, Commensurability Effects, and Preferential Defect Formation" Macromolecules, vol. 33, No. 1 (2000) pp. 80–88.

Huang et al. "Neutrality Conditions for Block Copolymer Systems on Random Copolymer Brush Surfaces" Macromolecules, vol. 32, No. 16 (1999) pp. 5299–5303.

Huang et al. "Surface–Initiated Radical Polymerization on Porous Silica" Analytical Chemistry, vol. 69, No. 22 (1997) pp. 4577–4580.

Huang et al. "Surface Initiation of Living Radical Polymerization for Growth of Tethered Chains of Low Polydispersity" Macromolecules, vol. 32, No. 5 (1999) pp. 1694–1696.

Huang et al. "Using Surface Active Random Copolymers to Control the Domain Orientation in Diblock Copolymer Thin Films" Macromolecules, vol. 31, No. 22 (1998) pp. 7641–7650.

Huse et al. "Generation of a Large Combinatorial Library of the Immunoglobulin Repertoire in Phage Lambda" Science, vol. 246, No. 4935 (Dec. 1989) pp. 1275–1281.

Husseman et al. "Controlled Synthesis of Polymer Brushed by "Living" Free Radical Polymerization Techniques" Macromolecules, vol. 32, No. 5 (1999) pp. 1424–1431.

Husemann et al. "Manipulation of Surface Properties by Patterning of Covalently Bound Polymer Brushes" Journal of the American Chemical Society, vol. 122, No. 8 (2000) pp. 1844–1845.

Husemann et al. "Surface–Initiated Polymerization for Amplification of Self–Assembled Mono–layers Patterned by Microcontact Printing" Angew. Chem. Int. Ed., vol. 38, No. 5 (1999) pp. 647–649.

Jordan et al. "Surface Initiated Living Cationic Polymerization of 2–Oxazolines" Journal of the American Chemical Society, vol. 120, No. 2 (Jan. 1998) pp. 243–247.

Kohler et al. "Continuous Cultures of Fused Cells Secreting Antibody of Predefined Specificity" Nature, vol. 256, No. 5517 (Aug. 1975) pp. 495–497.

Kozbor et al. "The Production of Monoclonal Antibodies from Human Lymphocytes" Immunology Today, vol. 4, No. 3 (1983) pp. 72–79.

Laschitsch et al. "Thickness Dependence of the Solvent–Induced Glass Transition in Polymer Brushes" Macromolecules, vol. 32, No. 4 (1999) pp. 1244–1251.

Lee et al. "Surface Photograft Polymerization on Segmented Polyurethane Using the Iniferter Technique" Journal of Biomedical Materials Research, vol. 47, No. 4 (1999) pp. 564–567.

Li et al. "Mono– and Dinitroxide Styrene Polymerization Initiators" Macromolecules, vol. 29, No. 26 (1996) pp. 8554–8555.

Lockhart et al. "Expression Monitoring by Hybridization to High–Density Oligonucleotide Arrays" Nature Biotechnology, vol. 14, No. 13, (1996) pp. 1675–1680.

Lueking et al. "Protein Microarrays for Gene Expression and Antibody Screening" Analytical Biochemistry, vol. 270, No. 1 (1999) pp. 103–111.

Malmstrom et al. "Development of a New Class of Rate–accelerating Additives for Nitroxide–Mediated 'Living' Free Radical Polymerization" Tetrahedron Letters, vol. 53, No. 45 (1997) pp. 15225–15236.

Mamlstrom et al. "Macromolecular Engineering via 'living' Free Radical Polymerizations" Macromol. Chem. Phys. vol. 199, No. 6 (Jun. 1998) pp. 923–935.

Mansky et al. "Controlling Polymer–Surface Interactions with Random Copolymer Brushes" Science, vol. 275 (Mar. 1997) pp. 1458–1460.

Mansky et al. "Ordered Diblock Copolymer Films on Random Copolymer Brushes" Macromolecules, vol. 30, No. 22 (1997) pp. 6810–6813.

Matyjaszewski et al. "Polymers at Interfaces: Using Atom Transfer Radical Polymerization in the Controlled Growth of Homopolymers and Block Copolymers from Silicon Surfaces in the Absence of Untethered Sacrificial Initiator" Macromolecules, vol. 32, No. 26 (1999) pp. 8716–8724.

Matyjaszewski et al. "Simple and Efficient Synthesis of Various Alkoxyamines for Stable Free Radical Polymerization" Macromolecules, vol. 31, No. 17 (1998) pp. 5955–5957.

McGall et al. "The Efficiency of Light–Directed Synthesis of DNA Arrays on Glass Substrates" Journal of the American Chemical Society, vol. 119, No. 22 (Jun. 1997) pp. 5081–5090.

Meier et al. "Polymerization of Styrene with Initiator Ionically Bound to High Surface Area Mica: Grafting via an Unexpected Mechanism" vol. 27, No. 6 (1994) pp. 1637–1641.

Nakayama et al. "Preparation of Poly(ethylene glycol)–polystyrene Block Copolymers Using Photochemistry of Dithiocarbamate as a Reduced Cell–Adhesive Coating Material" Biomaterials, vol. 20 (1999) pp. 963–970.

Nakayama et al. "Surface Macromolecular Architectural Designs Using Photo–Graft Copolymerization Based on Photochemistry of Benzyl N–N–Diethyldithiocarbamate" Macromolecules, vol. 29, No. 27 (1996) pp. 8622–8630.

Nakayama et al. "Surface Macromolecular Microarchitecture Design: Biocompatible Surfaces via Photo–Block–Graft–Copolymerization Using N–N–Diethyldithiocarbamate" Langmuir, vol. 15, No. 17 (1999) pp. 5560–5566.

Otsu "Iniferter Concept and Living Radical Polymerization" Journal of Polymer Science, Part A: Polymer Science, vol. 38 (2000) pp. 2121–2136.

Otsu et al. "Solid–Phase Block Copolymer Synthesis by the Iniferter Technique" vol. 19, No. 7 (1986) pp. 2087–2089.

Peng et al. "Polymer Brushes with Liquid Crystalline Side Chains" Macromolecules, vol. 32, No. 20 (1999) pp. 6759–6766.

Petro et al. "Polymers Immobilized on Silica Gels as Stationary Phases for Liquid Chromatography" Chromatographia, vol. 37, No. 9–10 (Nov. 1993) pp. 549–561.

Prucker "Grafting of Polymers to Microparticulate Silica by Using Immobilized Azo Initiators" Chemical Abstracts, vol. 123, No. 18 (1995) Abstract No. 123: 299210z.

Prucker et al. "Mechanism of Radical Chain Polymerizations Initiated by Azo Compounds Covalently Bound to the Surface of Spherical Particles" Macromolecules, vol. 31, No. 3 (1998) pp. 602–613.

Prucker "Synthesis of Poly(styrene) Monolayers Attached to High Surface Area Silica Gels Through Self–Assembled Monolayers of Azo Initiators" Macromolecules, vol. 31, No. 3 (1998) pp. 592–601.

Ruhe "Polymers Grafted From Solid Surfaces" Macromol. Symp., vol. 126 (1997) pp. 215–222.

Sarin et al. "Inhibition of Acquired Immunodeficiency Syndrome Virus by Oligodeoxynucleoside Methylphosphonates" Proceedings of the National Academy of Sciences USA, vol. 85, No. 20 (Oct. 1988) pp. 7448–7451.

Seery et al. "Designing Polymer Surfaces on Gold and Glass Using Surface Initiated Polymerizations" 214th ACS National Meeting, Los Vegas, NV (1997) Abstract 044.

Seery et al. "Direct Synthesis of Polymer Brushes" Polymer Preprints, vol. 40, No. 2 (1999) pp. 148–149.

Seidel et al. "Individual Polymer Paths and End–Point Stretching in Polymer Brushes" Macromolecules, vol. 33, No. 2 (2000) pp. 634–640.

Semenov et al. "Collective Dynamics of Polymer Brushes" Macromolecules, vol. 33, No. 2 (2000) pp. 613–623.

Shah et al. "Using Atom Transfer Radical Polymerization to Amplify Monolayers of Initiators Patterned by Microcontact Printing into Polymer Brushes for Pattern Transfer" Macromolecules, vol. 33, No. 2 (2000) pp. 597–605.

Sidorenko et al. "Radical Polymerization Initiated from a Solid Substrate. 3. Grafting from the Surface of an Ultafine Powder" Macromolecules, vol. 32, No. 14 (1999) pp. 4539–4543.

Southern et al. "Molecular Interactions on Microarrays" Nature Genetics Supplement, vol. 21 (Jan. 1999) pp. 5–9.

Stein et al. "Physicochemical Properties of Phosphorothioate Oligodeoxynucleotides" Nucleic Acids Research, vol. 16, No. 8 (1988) pp. 3209–3221.

Sugawara et al. "Novel Surface Graft Copolymerization Method With Micron–Order Regional Precision" Macromolecules, vol. 27, No. 26 (1994) pp. 7809–7814.

Theato et al. "Stabilization of Lipid Bilayers on Surfaces Through Charged Polymers" J.M.S.—Pure Appl. Chem., vol. A36, No. 7&8 (1999) pp. 1001–1015.

Tovar et al. "Patterning Molecularly Thin Films of Polymers—New Methods for Photolithographic Structuring of Surfaces" Supramolecular Science, vol. 2, No. 2 (1995) pp. 89–98.

Tsubokawa et al. "Effect of Initiating Groups Introduced onto Ultrafine Silica on the Molecular Weight Polystyrene Grafted onto the Surface" Polymer Bulletin, vol. 31, No. 4 (1993) pp. 457–464.

Tsubokawa et al. "Effect of polymerization conditions on the molecular weight of polystyrene grafted onto silica in the radical graft polymerization initiated by azo or peroxyester groups introduced onto the surface" *Colloid & Polymer Science,* vol. 273, No. 11 (1995) pp. 1049–1054.

Tsubokawa et al. "Surface Grafting of Polymers onto Carbon Thin Film" Journal of Applied Polymer Science, vol. 58, No. 8 (Nov. 21, 1995) pp. 1221–1227.

Tsubokawa et al. "Surface Grafting of Polymers onto Glass Plate: Polymerization of Vinyl Monomers Initiated by Initiating Groups Introduced onto the Surface" Journal of Applied Polymer Science, vol. 65 (1997) pp. 2165–2172.

Tsubokawa et al. "Surface Modification of Carbon Microbead by the Grafting of Polymers" J.M.S.—Pure Appl. Chem., vol. A32, No. 3 (1995) pp. 525–535.

Vatansever et al. "Modification of Glass Surfaces by Using Tethered Romp Catalysts" 215th ACS National Meeting, Dallas, TX (1998) Abstract 146.

Wang et al. "Facile Synthesis of New Unimolecular Initiators for Living Radical Polymerizations" Macromolecules, vol. 31, No. 19 (1998) pp. 6727–6729.

Weck et al. "Ring–Opening Metathesis Polymerization from Surfaces" Journal of the American Chemical Society, vol. 212, No. 16 (1999) pp. 4088–4089.

Weisenhorn et al. "Imaging Single–Stranded DNA, Antigen–Antibody Reaction and Polymerized Langmuir–Blodgett Films with an Atomic Force Microscope" Scanning Microscopy, vol. 4, No. 3 (1990) pp. 511–516.

Williams et al. "A New Mechanism Involving Cyclic Tautomers for the Reaction with Nucleophiles of the Water–Soluble Peptide Coupling Reagent 1–Ethyl– 3–(–3–(dimethylamino)propyl)carbodiimide (EDC)" Journal of the American Chemical Society, vol. 103, No. 24 (1981) pp. 7090–7095.

Xia et al. "Soft Lithography" Angew. Chem. Int. Ed., vol. 37 (1998) pp. 550–575.

Yamamoto et al. "Preparation of Well–Defined Polymer Brushes on Silicon Substrate by the Surface–Initiated ATRP Technique and Their Characterization" Polymer Preprints, vol. 40, No. 2 (1999) pp. 401–402.

Yin et al. "Grafting of Poly(Acrylic Acid) onto Nonporous Glass Bead Surfaces" Polymers for Advanced Technologies, vol. 8(1997) pp. 761–766.

International Search Report for PCT/US00/18339 dated Sep. 6, 2000.

* cited by examiner

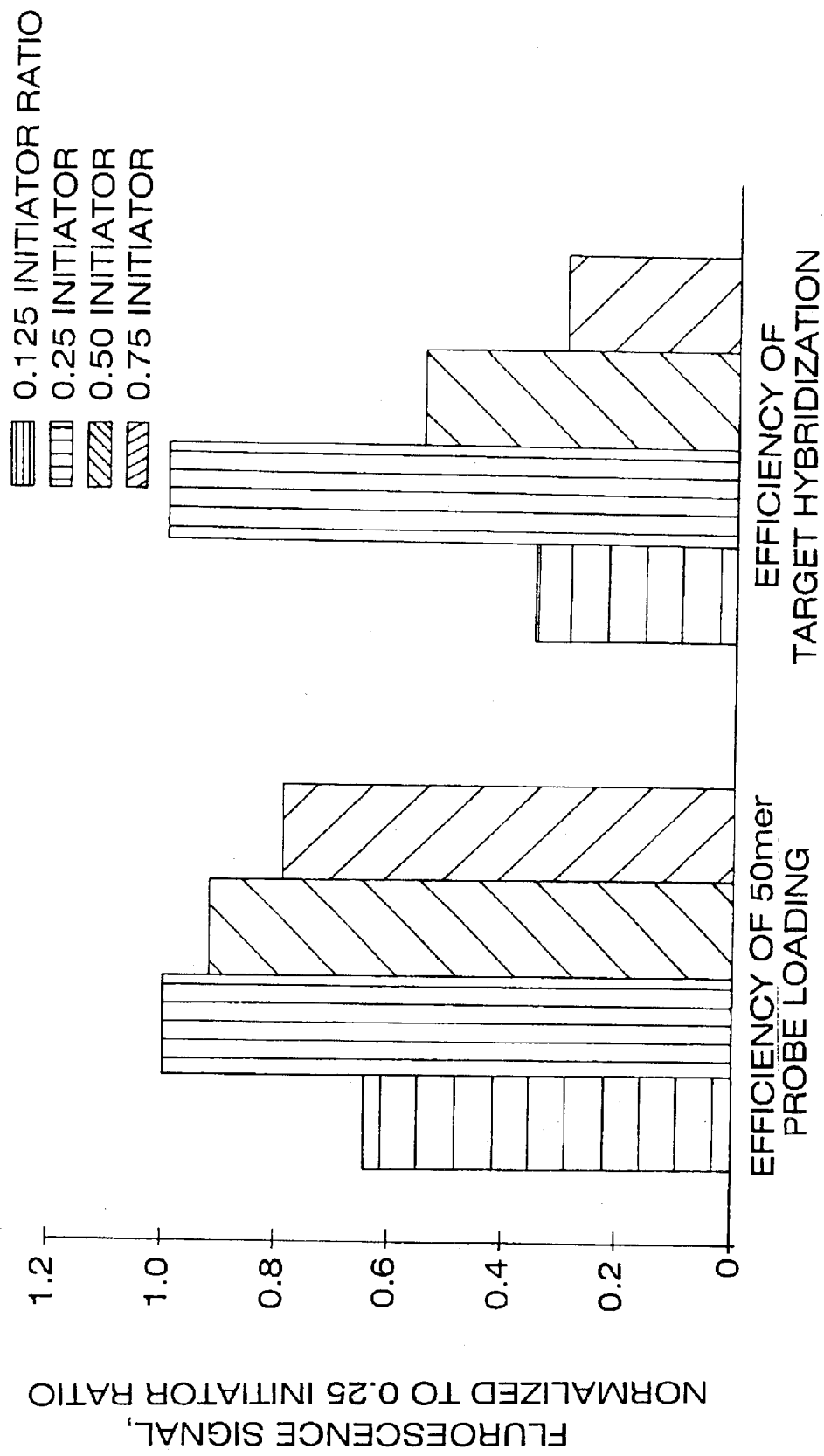

POLYMER BRUSHES FOR IMMOBILIZING MOLECULES TO A SURFACE AND HAVING WATER-SOLUBLE OR WATER-DISPERSIBLE SEGMENTS THEREIN AND PROBES BONDED THERETO

CROSS-REFERENCE TO RELATED APPLICATION

This application is a continuation of, and claims priority from, U.S. Application Ser. No. 09/609,461 (filed Jul. 3, 2000), now U.S. Pat. No. 6,692,914 which is a continuation-in-part of U.S. Application Ser. Nos. 09/347,606, abandoned 09/347,607, abandoned 09/347,608, abandoned and 09/347,609 now U.S. Pat. No. 6,472,486 all of which were filed on Jul. 2, 1999 and which claims the benefit of priority therefrom as well as from U.S. Provisional Application Nos. 60/146,936 (filed Jul. 31, 1999) and 60/177,879 (filed Jan. 24, 2000). All of these related applications are incorporated by reference herein.

BACKGROUND

This invention relates to a polymer brush that features a polymer layer on a substrate surface, the polymer layer being composed of a number of polymer chains each of which include a water-soluble or water-dispersible segment having two termini, one terminus being free and the other being bound to the substrate surface. In one embodiment, the present invention is directed to a sensor wherein probes for biological molecules are attached to these water-soluble or water-dispersible segments. Sensors of this type are particularly useful for analyzing aqueous samples that contain biological materials. The present invention further relates to methods of synthesizing such sensors. In preferred embodiments, the polymers have controlled molecular architectures that allow for tuning the concentration or accessibility of the probes, and thus, for tuning properties (e.g., sensitivity) of the sensor.

Sensors for analyzing biological samples typically have the ability to process samples accurately and rapidly in an aqueous environment. This, in turn, looks to the presence of multiple probes on a single substrate surface capable of selectively interacting with components of the sample. For example, nucleic acid hybridization assays use multiple oligonucleotide probes bound to the substrate surface at pre-selected sites. The oligonucleotide probes, in turn, are available to participate in a hybridization reaction with selected nucleic acid components of the sample. Generally, this interaction of probe and sample relates to the utility of the components of the biological sample, such as the identity, concentration, purity or form of the components being sensed. There are generally many types of probes known, for example, antibodies that may immunoreact with a desired protein in a diagnostic assay, other protein binding assays, and dyes that change color to indicate the concentration of a desired protein, enzyme, small organic molecule, or inorganic molecule such as calcium or lithium.

Attaching probe molecules to surfaces is often difficult because the surfaces lack functional groups that are uniquely reactive in an aqueous system or are readily accessible to the probe molecules as a result of factors such as surface crowding or steric hindrance. This problem becomes particularly acute as the number of functional groups per unit area of surface increases. In addition, once probes are bound to the surface, they must remain accessible to components of the biological sample. Here, too, factors such as steric hindrance may hamper accessibility. Molecular crowding (i.e., density) becomes a critical issue as well, particularly in systems where fluorescence quenching can be an issue.

Controlled free radical polymerization methods with living-type kinetics have been used to covalently bond polymers to the surfaces of substrates and thereby form "polymer brushes." Husseman et al., *Macromolecules* 1999, 32, 1424–31, for example, describes a variety of polymer brushes prepared using such methods. The resulting brushes, however, were not water-soluble or water-dispersible and thus were not suitable for applications involving aqueous samples such as biological samples. Additionally, Husseman et al. fail to address the importance of controlling the grafting density of, or spacing between, the polymer chains attached to the substrate surface, in order to optimize both the number of probes which may be attached for a given application, as well the efficiency of those probes, once attached, to interact with the target molecules.

Accordingly, a need to continues to exist for a polymer brush, as well as a process for the preparation thereof, having polymer chains of a controlled molecular architecture (i.e., composition, functionality, molecular weight, polydispersity, etc.), as well as spacing or grafting density on the substrate surface, such that the attachment of probe molecules of a given size or type can be optimized. Additionally, a need continues to exist for a sensor (i.e., a polymer brush having probe molecules attached thereto), as well as a process for the preparation thereof, having a controlled structure, such that probe accessibility to the target biological molecules can be optimized.

SUMMARY

Thus it is an object of this invention to provide a platform for selectively interacting with biomolecules, such as sensors for biomolecule recognition and bioseparations, among other applications. In preferred applications, it is an object of the invention to provide a sensor comprising a substrate surface, polymers associated with the surface, and probes attached to the polymers, where each of the polymers have at least a water-soluble or water-dispersible segment having functional groups capable of bonding to the probes. In some contexts, these sensors may be considered to be "polymer brushes."

It is also an object of this invention to provide biosensors that feature controlled-architecture polymers bound to a surface of a substrate that include water-dispersible or water-soluble segments to which probes for biological molecules are covalently bound via functional groups found on the segments.

Although the invention is more specifically described herein in the context of a biosensor, it is to be understood that the invention is not necessarily to be limited to such applications.

It is another object of this invention to provide polymer modified surfaces or articles.

It is yet another object of this invention to provide a method of making polymer-modified surfaces using free radical polymerization, preferably controlled free radical polymerization having living-type kinetics.

This invention provides the advantage of careful control of the identity, surface grafting density or spacing, and molecular architecture of the functionalized polymer chains. Accordingly, use of this invention provides the ability to prepare a functionalized surface that, in terms relative to the accessibility of surface-bound functional groups to probe molecules, and probe molecules to biological sample components, approximates that of an aqueous solution. At the same time, the probes are tethered to the surface, thereby facilitating analysis following contact with a biological sample.

This invention provides functionalities that bind probes, which are not attached to a flat surface. This means that solution chemistry is more closely simulated, surface effects are reduced, and as a result the sensors of this invention provide increased sensitivity, increased signal, increased signal to noise ratios and increased dynamic range.

In addition, those of skill in the art are able to choose monomers that yield functionalized surface brushes that display a low fluorescent background due to the lack of non-specific binding of the bio-molecule in the sample.

Overall sensitivity of the sensor is also improved, it is believed, due to the spacing of the functional groups that bind the probes from the surface of the substrate. In other words, increased sensitivity has been observed, which is believed to result from the fact that the functional groups that bind the probes are now attached to a polymer chain thereby distancing the probes (and hence the related biochemistry) from the surface of the substrate, reducing, if not completely eliminating, surface effects.

Briefly, therefore, the present invention is directed to a polymer brush for binding a molecule in an aqueous sample in an assay. The polymer brush comprises a substrate having a surface, and a layer on the substrate surface comprising polymer chains. The polymer chains have at least two termini and a water-soluble or water-dispersible intermediate portion between the termini, one terminus being free and the other terminus being bound to the substrate surface. The terminus of each polymer chain that is bound to the substrate surface comprises a residue of a surface bound initiator having the formula

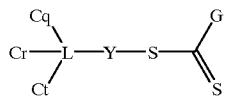

wherein: C is a moiety on the surface of the substrate; L is a linker group capable of bonding to at least one C moiety; q, r and t are independently 0 or 1, provided the sum of q+r+t is at least 1; Y is a residue capable of initiating free radical polymerization upon homolytic cleavage of the Y—S bond; S is sulfur; and, G is a nitrogen or an oxygen heteroatom. Additionally, the intermediate portion of each polymer chain has a weight average molecular weight of at least about 1000, is substantially free of crosslinks to an intermediate portion of another polymer chain, contains repeat units derived from an acrylamide-based monomer and at least one other monomer, and contains functionalized sites which have been formed in their active state (reacting directly with the probe molecules, as further described herein).

The present invention is further directed to a method for detecting a biological molecule in an aqueous sample comprising contacting a polymer brush of the present invention with said sample, and thereafter analyzing said polymer brush for the presence or quantity of said biological molecule.

The present invention is still further directed to a method for preparing a sensor for detecting a biological molecule in an aqueous sample. The method comprises bonding an iniferter initiator to a substrate surface at one or more points to form a derivatized surface, said iniferter initiator comprising an initiator-control agent adduct having the formula:

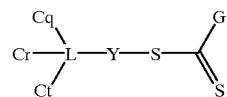

wherein: C is a moiety on the surface of the substrate; L is a linker group capable of bonding to at least one C moiety; q, r and t are independently 0 or 1, provided the sum of q+r+t is at least 1; Y is a residue capable of initiating free radical polymerization upon homolytic cleavage of the Y—S bond; S is sulfur; and, G is a nitrogen or an oxygen heteroatom. The derivatized surface is then contacted with a composition comprising a water-soluble or water-dispersible free radically polymerizable monomer mixture, the mixture containing an acrylamide-based monomer and at least 1 other monomer, under reaction conditions to form bound polymer chains comprising a water-dispersible segment having a weight average molecular weight of at least about 1000 and one or more active functionalized sites thereon, the active site(s) reacting directly with a probe selective for the biological molecule. Unbound polymer is separated and then a probe is bonded to the bound polymer chains through the active functionalized sites.

The present invention is further directed to polymer brushes prepared by the methods of the present invention.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 7 is a bar graph illustrating efficiency of oligonucleotide loading and hybridization as a function of chain density.

DETAILED DESCRIPTION

Accessibility Considerations

The invention provides platforms for selectively interacting with molecules, in general, and biomolecules, in particular. Although the invention is more specifically described herein in the context of a biosensor, it is to be understood that the invention is not necessarily to be limited to such applications.

In preferred applications, the invention provides a sensor for detecting various molecules in a biological sample, the sensor featuring controlled-architecture polymers bound, and more preferably covalently bound, to a surface of a substrate. More specifically, the invention provides a polymer brush, suitable for binding biological molecules, comprising a substrate having a surface, a layer on the substrate surface which comprises a plurality of polymer chains, each chain containing at least one water-dispersible or water-soluble segment to which biological probes are bound, preferably covalently bound, via functional groups found on these segments. As further described herein, in order to enable the accessibility of the biological probes to approach the accessibility of probes which are in solution, the water-soluble (or water-dispersible) segments to which they are attached are preferably free of covalent crosslinking, have a weight average molecular weight of at least about 1,000, and at least have two termini with one terminus being free and the other being bound, and preferably covalently bound, to the substrate surface. Probe molecule accessibility to biomolecules, including in some cases biopolymers, in an aqueous sample is further enhanced by the water-soluble or water-dispersible nature of the segments to which they are attached, the segments providing an environment that is compatible with the sample in which the analysis is performed.

Functional Group Accessibility

Figure 1:
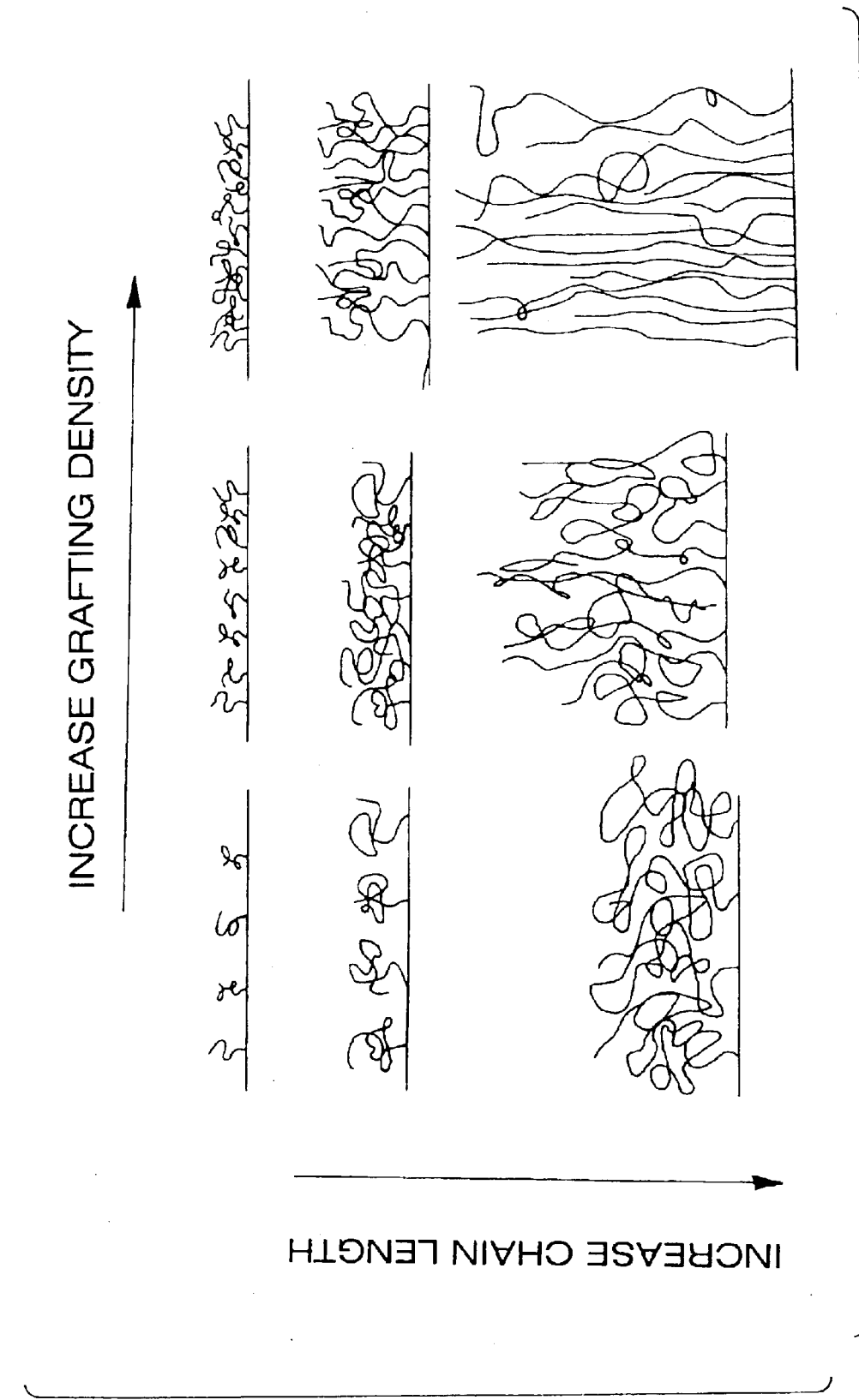
FIG. 1 is a schematic drawing showing the effect of increasing grafting density and increasing polymer chain length on a hypothetical surface to which polymer chains are bound.

The nature of the problem associated with functional group accessibility is generally illustrated in FIG. 1, which depicts a hypothetical surface to which a number of polymer chains are bound. As further described in greater detail below, without being held to a particular theory, it is generally believed that, for polymers of a given composition and chain length, as the average chain grafting density (i.e., the average number of bound chains per unit area) increases, the number of accessible functional groups (i.e., the number of functional groups on the polymer chains which are capable of attaching to a molecule of a given size) increases. However, as the grafting density continues to increase, eventually chains are close enough to become entangled and otherwise sterically hinder the functional group-bearing sites, thereby limiting the ability to attach a probe molecule to the polymer chain at these sites; that is, as the grafting density continues to increase, eventually a point may be reached where the number of accessible functional groups begins to decrease due to increased steric hinderance, a reduction of total free volume, a reduction of the mesh size, and a hindered diffusion of the biomolecules, even though the total number of functional groups continues to increase. If the grafting density increases further, the polymer chains can become so tightly packed or so entangled that essentially the only functional groups accessible to a probe are located at or near to the chain ends (e.g., near the surface below which the grafting density essentially approaches zero).

Figure 6:
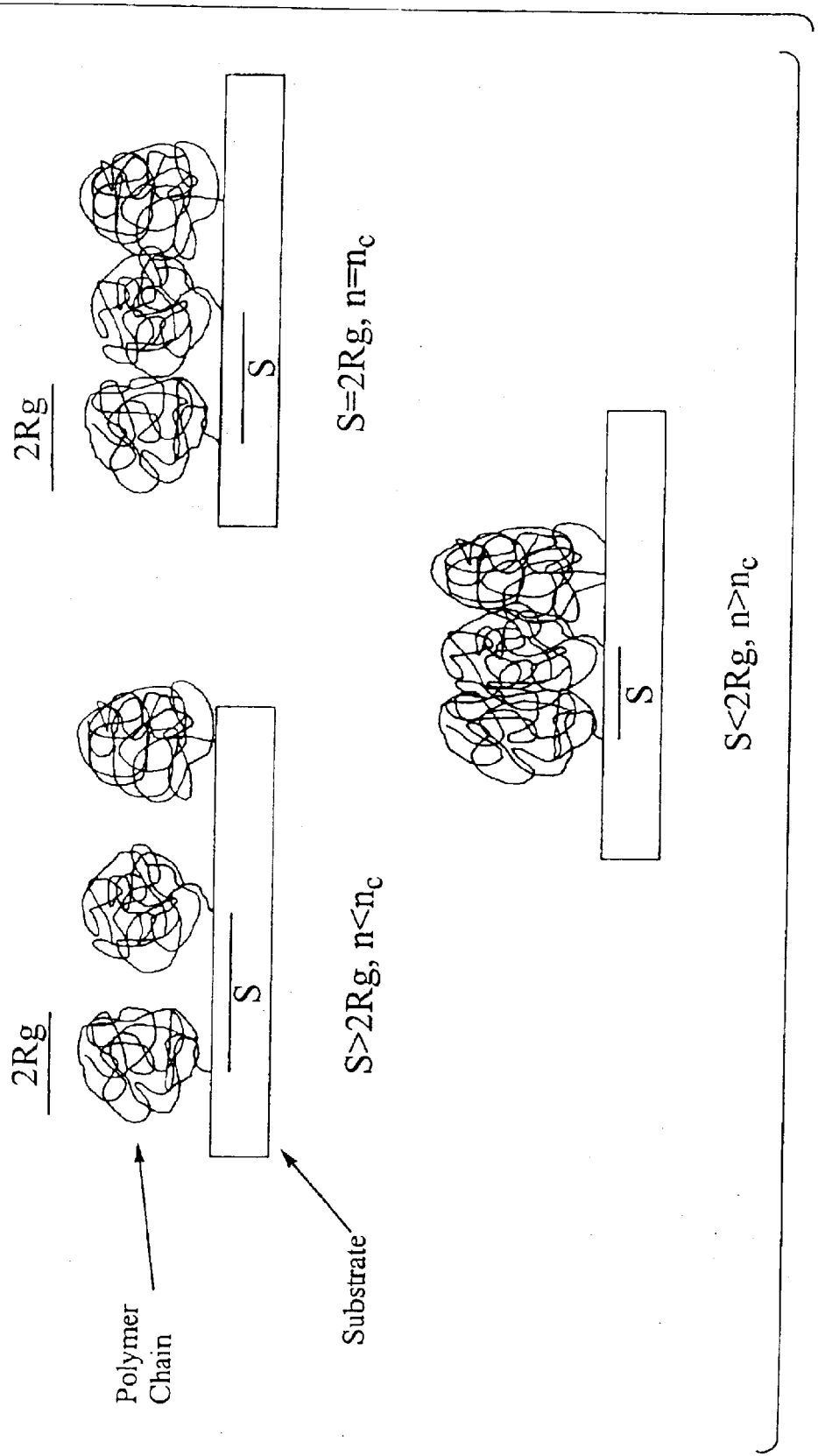
FIG. 6 is a schematic drawing between chain spacing, S, radius of gyration, Rg, and chain grafting density, n, and a critical chain grafting density, $n_c$, at which chain entanglements begin.

A similar phenomenon is believed to occur as chain length increases for a given grafting density. If the segments are short enough so that the average coil diameter is significantly less than the average distance between attachment points, then there is no overlap between the segments. As the segments are made longer, the size of the coils which they form increases until they overlap. With further increase in the chain length, the chains begin to stretch away from the substrate. Once the chains are stretched, further increase in the chain length at a fixed grafting density leads primarily to an increase in the "wet thickness" of the brush, but does not lead to significant further increases in the average polymer concentration within the brush or a reduction of the mesh size. Mesh sizes may be determined, for example, by means analogous to those described in U.S. Pat. No. 5,126,021. Accessibility issues are also graphically displayed in FIG. 6, where it is shown that there exists a critical chain density, $n_c$, which is the point at which surface bound polymer chains begin to entangle. As described herein, this density may be controlled to control the accessibility of the functional groups on the polymer as desired for a particular embodiment.

The present invention addresses the problem of functional group accessibility by disclosing how to control various aspects of the preparation methods, including for example the density of available functional moieties on the surface (controlled, for example, by various surface treatments, as described herein and in the literature), the chain lengths (e.g., molecular weight), chain grafting density, and the type and/or number of functional group-containing monomers, thus enabling those of skill in the art to design a sensor with a desired number of available or accessible functional groups present. Stated another way, the present invention discloses how to control the manner by which surface-bound polymers having water-soluble or water-dispersible segments are prepared to enable functional group accessibility to be adjusted which, in turn, enables the polymer-modified surface to be tailored for a given application to optimize subsequent probe attachment and probe availability for sample screening.

In this way the invention provides the ability to control the number of functional groups that are available for binding probes of a biosensor, and ultimately thereby to control or tune the sensitivity and other properties of the biosensor. More specifically, depending on the volume occupied by the probe molecules in a particular solution (e.g., aqueous), the grafting density of the polymer chains can be tuned to accommodate such probe molecules to avoid surface crowding and optimized accessibility of the probe molecules to the bio-process. It is believed that increased numbers of functional groups, along with minimizing surface effects as discussed above, advantageously provides improved sensitivity of the probe in a bio-process, along with increasing signal, increasing signal to noise ratios and increasing dynamic range (i.e., increasing ability to detect decreasing numbers of target molecules in the sample, as further described herein).

Referring to FIGS. 2–5, in one embodiment of the present process, a radical initiator is bound to the surface of a substrate to form a derivatized substrate surface (e.g., FIGS. 2, 3 and 4), which is subsequently contacted with one or more monomers to form surface-bound polymer chains (e.g., FIG. 5) which extend from the substrate surface generally in a direction normal to the substrate surface. In one embodiment, the polymer chains are not substantially crosslinked to other strands, covalently or otherwise, thus permitting a range of movement substantially independent of other polymer chains. According to one approach (and as further described herein), it can be assumed that substantially all functionalities originally on the surface are bound to either an initiator or initiator-control agent adduct or, in some embodiments, a dummy molecule (i.e., a molecule which does not participate in a subsequent polymerization reaction). The monomers are chosen to provide desired functional groups (e.g., hydroxyl, carboxyl, amino, thiol, etc. groups) on the polymer. Desired probes are then attached to the functional groups to complete the sensor.

The average distance between the polymer chains depends, at least in part, upon the size of the probes to be attached as well as the sensing process to be employed. Typically, however, the average distance between the polymer chain attachment points is less than about 10 times the radius of gyration (Rg) of polymer chain under the conditions of the assay being employed, preferably less than about 4 times Rg, and more preferably less than about equal to twice the Rg of the polymer chain. Without being held to a particular theory, it is generally believed that about twice the radius of gyration or more is preferred because, if the polymer chains are further apart than their diameter, then there will be an unnecessary amount of space between them; that is, if the polymer chains are further apart than their diameter there will be empty areas which could be filled with additional polymer chains without causing any significant additional chain overlap and crowding.

Those of skill in the art will also understand that grafting density and molecular weight may be expressed in terms of a "mesh size," which relates to the size of the molecule that may diffuse into, or access, the free volume or space between the polymer chains. Stated another way, for a polymer brush of a given grafting density and molecular weight, a molecular volume or size threshold exists, below which molecules may diffuse into the free volume or space between the chains, while above which the molecules are repelled or prevented from entering this free volume (instead remaining at or near the surface of the polymer layer comprised of the polymer chains). Accordingly, the mesh size of the polymer brush in some embodiments should be sufficient to allow diffusion of the analyte molecule (e.g., the probe molecule to be attached to the segment functional groups or the target molecule which is to bind with the probe) into this free volume between the surface-bound polymer chains, and preferably in a commercially practical period of time. If there are multiple target analytes, then the mesh should be at least as large as the largest target analyte. Typically, therefore, the mesh size may range from greater than about 0.1, 0.2, 0.5 or even 1 times the radius of gyration of the analyte molecule, up to greater than about 1, 2, 4 or even 5 times the radius of gyration of the analyte molecule. In other contexts, this theory is discussed in U.S. Pat. No. 5,126,021, which is incorporated herein by reference.

Examples of anlyte molecules commonly of interest in the art include:

Single-strand DNA: As determined by means common in the art (in this case, Atomic Force Microscopy; see, e.g., Weisenhorn et al., *Scanning Microscopy*, 4(3), 1990, pp. 511–516), the spacing between bases in a single-strand DNA segment is roughly about 5 Å. Because the single-strand DNA is very flexible and can coil upon itself, the width or thickness of a coiled 25 mer is about 6 Å, while the average contour length is about 50 Å.

Additionally, common radii of gyration (Rg) of single-strand DNA of various sizes known in the art (see, e.g., Chan et al., *Biophysical Journal*, 69, 2243–55 (1995)), include:

| Size (# of bases) | Rg (Å) |
| --- | --- |
| 6 | 10 |
| 30 | 40 |
| 160 | 250 |
| 2686 | 1190 |
| 4373 | 1600 |

Double-strand DNA: As determined by means common in the art (see, e.g., L. Stryer, *Biochemistry*, W. H. Freeman, pp. 76–77 (1988)), a double-strand DNA has a regular structure which is more rigid than the single-strand counterpart, and a length which has been calculated to be about 3.2 Å per base pair. Therefore, a double-strand 25 mer would have a length of about 80 Å, with a helical diameter of about 20 Å, and an estimated radius of gyration of about 45 Å.

Proteins: As determined by means common in the art (see, e.g., Hendrickson et al., PNAS 86, 1989), Streptavidin (SA) has a molecular weight of about 60 kDaltons, with dimensions of about 54×58×48 Å, which equals about 150,336 Å$^3$, and a radius of gyration of about 30 Å. Similarly, Phycoerythrin (PE) has been found to have a molecular weight of about 240 kDaltons, with an estimated molecular volume of about 600,000 Å$^3$, and a radius of gyration of about 50 Å. The SA-PE conjugate molecular volume is about 750,000 Å$^3$ (see, e.g., Glazer, A. Ann., *Rev. Microbiol.*, 36, pp.173–198 (1982)), and a radius of gyration of about 50 Å.

Related to the concept of free volume between the water-soluble (or water-dispersible) segments bound to the substrate surface is another parameter, referred to herein as the "swelling ratio." Briefly, this is the ratio of the solvated brush thickness to the dry film thickness, and indicates both the degree of expansion of the brush as well as the "free volume" fraction in the solvated brush. The solvated film thickness, as further described herein, may be measured using techniques standard in the art, including neutron scattering and reflectivity, the surface force apparatus, and scanned probe microscopy (such as AFM).

In general, brushes with equivalent dry thickness, but with different molecular weight and grafting density, may demonstrate a significant variation in the degree of swelling and the height of the solvated brush as a function of polymer chain molecular weight. For example, for a 10 Å thick dry film, the solvated thickness is 123 Å for a Mw=10,000 polymer, 573 Å for a Mw=100,000 polymer, and 2660 Å for a Mw=1,000,000 polymer. Thus although the total amount of polymer present per unit area is the same in both cases (expressed, for example, as mass per unit area), the higher molecular weight polymer becomes distributed over a much larger volume, and at much lower concentration, than the lower molecular weight polymer.

Similarly, it can be seen that for the same dry film thickness, the solvated brush made up of a higher molecular weight polymer has a much larger mesh size than a lower molecular weight polymer. For example, for a 40 Å thick dry film, the calculated mesh sizes for solvated brushes having three different molecular weights are 20 Å, 64 Å, and 204 Å, for molecular weights of 10,000, 100,000, and 1,000,000 gm/mole, respectively. As was discussed above regarding the brush height and density, the same number of monomers or the same mass of polymer is distributed in a much more open and accessible way when the polymer has the form of a smaller number of very long segments, versus a larger number of shorter segments.

In general, mesh size depends largely on the absolute grafting density (expressed in picomoles per square centimeter), and not so much on the molecular weight or the dimensionless grafting density. That is, a brush with a specified mesh size can be made to include a larger total volume and total number of binding sites by increasing the molecular weight while keeping the chain grafting density, n, essentially fixed.

The brush structure may be optimized with respect to both sensitivity and kinetics of attachment by always choosing the highest possible molecular weight, and tuning the mesh size and entanglement lifetime via the grafting density. By extending a brush with a very open structure (large mesh size) a great distance away from the substrate, it may be possible to achieve sensitivity much higher than is attainable with brushes commercially available to-date while maintaining a mesh size which is much larger than the size of the biomolecules of interest, thereby permitting very rapid diffusion of the biomolecules throughout the brush and possibly faster kinetics of attachment.

Regardless of the manner by which the "openness" of the brush is defined (i.e., by a swelling ratio, grafting density or mesh size), the important factor to be noted is the free movement of the polymer segments and the ability of molecules of a particular size (e.g., probe or target molecules) to diffuse into the polymer layer comprised of these segments. Accordingly, as mentioned herein, the substantial absence of permanent crosslinks (e.g., covalent crosslinks), and preferably all types of crosslinking, between these segments is preferred so that any entanglements (i.e., obstructions to segmental motion and molecular diffusion or movement) are short lived, thus maximizing the "openness" or mobility of the polymer brush.

The total number of functional groups for the attachment of probe is, at least in part, a function of polymer chain molecular weight, the number of functional groups per polymer chain and the grafting density of polymer chains on the substrate surface. Because of steric hindrance and/or polymer chain overlap, not all functional groups will necessarily be accessible to probe. The number of accessible functional groups may be determined by means common in the art. For example, the number of accessible functional groups, in a given area or volume, may be determined by adding dye molecules to the polymer-coated substrate of the present invention which bind to the accessible functional groups of the polymer chains. Once attached, the dye molecules may then be cleaved from the surface, collected and measured to determine the number of molecules that were attached to the surface, which in turn corresponds to the number of functional groups accessible to the dye molecules. The number of attached, or "cleavable," dye molecules also corresponds to the number of functional groups that would be accessible to probe molecules of a size similar to that of the dye molecules used in the analysis.

While the number of accessible function groups for a given brush configuration will vary with the size of the dye molecules utilized in the test (or, alternatively, the size of the probe molecules to be attached), generally speaking the number of accessible functional groups or sites for small molecules (e.g., small dye molecules having a size of, for example, less than about 10 Å) will typically range from about 20, 25 or even 30 picomoles/cm$^2$, up to about $5 \times 10^4$, $5 \times 10^5$, or even $5 \times 10^6$ picomoles/cm$^2$ (as determined by the cleavable dye analysis methods described herein). However, as the size of the molecule to be attached increases, these ranges may also change. For example, if the molecule to be attached is a protein (which in some cases may have a molecular volume 100 times greater than the dyes molecules referenced above), the number of accessible functional sites for the same surface may range from about 1, 5 or even 10 picomoles/cm$^2$ up to about $1 \times 10^4$, $1 \times 10^5$, or even $1 \times 10^6$. Sizes of common molecules which may be attached to the accessible functional sites include, for example:

Approximate Dye or Probe Size

Fluorescein: D ~10 Å
Dansyl choloride: D ~10 Å
8 mer ss oligo: Rg ~10 Å
25 mer ss oligo: Rg ~30 Å
50 mer ss oligo: Rg ~100 Å
Streptavidin (SA): D ~55 Å
IgG antibody: D ~65 Å
Phycoerythrin (PE): D 100 Å
SA-PE conjugate: D ~120 Å where D is diameter (used herein for molecules which have a well-defined structure), Rg is radius of gyration (used herein for molecules which do not have a well-defined structure, such as molecules having a random coil structure), ss is single strand and ds is double strand.

It is to be noted that which the Cleavable Dye Analysis may be used to determine the number of accessible functional groups, alternative methods known in the art may also be used to determine the total or actual number of functional groups in the polymer brush. For example, one method involves the use of radioactive or labeled monomers in the polymerization process. Once the polymer chains have been grown, analysis will provide the total number of monomer units which have been incorporated into the brush, which directly correlates to the number of functional groups present.

Substrates

A substrate is generally a material having a defined surface (e.g., rigid or semi-rigid surface). In many embodiments, at least one surface of the substrate will be substantially flat, although in other embodiments small beads, pellets, porous, etched substrates or irregular objects may provide the surface. The substrate may be organic or inorganic. Examples of suitable substrates include glass (e.g., silica glass), quartz, fiber optic threads, silicon (including silicon dioxide), inorganic and organic microspheres, plastic and polymer-coated substrates. The substrate may also take any desired size or shape, such as a square or round flat chip or a sphere. The substrate may also be a composite material or a multi-layer material with one or more materials presented at the surface.

As is generally known in the art, the surface of the substrate will contain functional groups (e.g., such as hydroxyl groups). The density of these functional groups is a function of the type of substrate material and any treatment steps applied to that substrate. For example, using known techniques, such as acid treatment (e.g., using a commercial product called Nochromix (Godax Laboratories)), the surface can be cleaned and left in a hydrophilic state. Polymer substrates may have functional groups intrinsic to the polymer or may have surface functional groups introduced by chemical treatment, corona discharge, plasma treatment, etc. Those of skill in the art may also use established methods for determining the density of the functional groups on the surface of substrates, such as titration, ellipsometry, X-ray photoelectron spectroscopy, fluorescent labeling, surface energy and contact angle measurements, and the like. Determining the concentration of functional groups per unit area on the surface of the substrate to be modified with the polymer chains discussed herein may be important to determining the grafting density of the polymer chains, as discussed herein. In many cases, knowledge of the surface being used will allow those of skill in the art to estimate or assume the number of functional groups per unit area, thereby providing a reasonable estimate of the amount of reagents to use in order to obtain a desired chain density per unit area. For example, an excess of reagent may be used when it is desired to attach polymer chains to all available surface functionalities. Substrates that do not contain accessible functional groups can also be used in the sensors of this invention, provided that they are first coated with a coating that provides such functional groups (as discussed herein).

Polymers Attached to the Surface of the Substrate

Water-dispersible/Water-soluble Segments

In accordance with the present invention, a layer is formed on the surface of a substrate, the layer comprising a plurality of polymer chains. Each of these polymer chains has two termini and a water-soluble or water-dispersible intermediate portion between the termini, one terminus being free and the other terminus being bound to the substrate surface. The water-soluble or water-dispersible intermediate portion typically has a weight average molecular weight of at least about 1,000, and depending upon the particular assay, it may preferably have a weight average molecular weight of at least about 10,000, 50,000, 100,000, 200,000, 300,000, 400,000, 500,000 or even at least about 750,000. In addition, the intermediate portion contains functionalized sites for the attachment of a probe for binding the molecule and is substantially free of crosslinks to the intermediate portion of other polymer chains. As a result, one terminus of each of the chains is free to extend into an aqueous environment and the other terminus is bound to the substrate surface, either directly (including, for example, where the end of the water-soluble or water-dispersible segment is bound to a portion of the initiator, or linker-initiator, molecule attached to the substrate surface, as further described herein) or indirectly (including, for example, (i) where an intervening, hydrophobic segment of polymer is present between the water-soluble or water-dispersible segment and the substrate surface, or (ii) where a triblock copolymer is formed, the central block being for example hydrophobic and attached or associated with the substrate surface in some way).

In this regard it is to be noted that, as used herein, "terminus" generally refers to end regions of the polymer chain, within which various polymer architectures may be present (e.g., linear chains, branched chains, etc.); that is, it is to be understood that, as used herein, "terminus" does not necessarily refer to the last atom at each end of the principal polymer chain.

It is to be further noted that, as mentioned herein, in order to maximize the "solution-like" character of the probes, it is preferred that these water-soluble or water-dispersible segments be substantially free (i.e., less than about 50%, 25%, 10%, 5%, or even about 1%) of covalent crosslinking, and more preferably substantially free of all types of physical crosslinking as well.

Generally speaking, the polymer brushes of the present invention may be prepared by one of two general approaches, (i) the "grafting from" approach, whereby the polymer chain is grown from the substrate surface, and (ii) the "grafting onto" approach, whereby a preformed polymer chain is linked onto the substrate surface. The "grafting from" approach includes the attachment of an initiating moiety onto a substrate capable of starting the polymerization of monomers. Possible polymerization techniques include radical, cationic, anionic, and metathesis, as well as insertion-type chain growth mechanisms. In one embodiment, the radical polymerization process is preferred due to its robustness towards aqueous environments and the large range of functional monomers available for this type of polymerization. Radical polymerizations can be implemented in a number of different ways known in the art, each having as a common feature that a radical forming species is linked to the substrate surface through the functional sites available on the surface. Standard radical initiators include, for example, azo and peroxide initiators, as well as redox systems which lead to uncontrolled polymerizations.

Uncontrolled free radical polymerizations usually produce broader molecular weight distributions, and moreover the number of chain keeps growing as the reaction proceeds, as opposed to controlled polymerization where ideally all the chains are formed at the beginning of the reaction. To a first approximation, the number of grafted chains is equal to the sum of the initiation events, which depend upon the half-life of the bound initiators and the initiator efficiency. "Initiator efficiency" refers to the fraction of the radicals which, once formed, actually generate a new chain. When implementing uncontrolled free radical polymerization, reaction conditions are chosen in order to control the chain density and the molecular weight. For example, in one embodiment, uncontrolled polymerization is carried out so as to decompose all the bound initators (achieved by selecting the proper combination of reaction time and temperature). More specifically, if $t_{1/2}$ is the half-life of the bound initators at a given temperature, then the reaction time is preferably $5*t_{1/2}$. The chain density is then the density of initiators bound on the surface, weighted by the initiator efficiency.

For uncontrolled free radical polymerizations, it is difficult to control the chain length because the radical concentration is not uniform in the polymerization mixture. Here, the non-covalently attached radicals on the surface can diffuse away from the substrate and, as a result, the local radical concentration will be extremely low, leading to uncontrollably high molecular weights. One way to address both the control of chain density as well as the control of molecular weight is to implement living free radical polymerization (LFRP) techniques. In the case of LFRP, the control of molecular weight is enabled through a control agent which reversibly deactivates the propagating radical. Living free radical polymerization techniques include, for example, nitroxide mediated polymerization, degenerative transfer (such as reversible addition/fragmentation transfer), atom transfer radical polymerization, among other techniques known to people skilled in the art. In one specific case the initiator and the control agent are combined in one molecule which is referred to as a initiator-control agent adduct. To gain control of molecular weight it is necessary to control the radical concentration at the vicinity of the surface. One way to address this issue is to add both extra initiators and/or adducts, as well as control agents into the polymerization mixture.

Various combinations of initiating moieties, control agents and adducts, as well as the manner by which they are employed (e.g., in solution, bound to the surface, or both), may be used in the preparation of the polymer brushes of the present invention including, for example:

| Approach | Surface   | Solution      |
|----------|-----------|---------------|
| 1        | Initiator | —             |
| 2        | Initiator | initiator     |
| 3        | Initiator | Control agent |
| 4        | Adduct    | adduct        |
| 5        | Adduct    | control agent |
| 6        | Adduct    | —             |

In one embodiment, an initiator-control agent adduct is attached to the surface via the initiator moiety and non-surface bound adduct is added to the polymerization mixture. This approach leads to the formation of both polymer bound to the substrate surface as well as polymers in solution (which enable valuable information to be learned about the resulting surface because the molecular weight, monomer incorporation and molecular weight distribution are believed to be identical for both polymers). This technique leads to excellent molecular weight control, narrow polydispersities and allows one to monitor the polymer brush growth by measuring the properties of the solution grown polymer. In another preferred embodiment, the adduct is also attached to the substrate surface, but here only the control agent (instead of the adduct) is added to the polymerization mixture.

In yet another embodiment, no adduct is used but the control agent is added at a concentration similar to the steady-state concentration achieved in the above embodiment wherein adduct is both bound to the substrate surface and present in solution. Hence, the radicals that are found stem mostly from the bound initiator/bound initiator-control agent adduct. The control over molecular weight is ensured by the stable free radical purposely added in the polymerization reaction. As the polymerization proceeds mainly from the surface, virtually no polymer is formed in the solution. Polymer growth is monitored by measuring the polymer layer thickness (e.g. by ellipsometry). Since no polymer is formed in solution, this approach has the advantages of providing (i) a lower viscosity reaction mixture, which facilitates the recovery of monomer and isolation of the modified substrate, and (ii) a lower cost of manufacturing, since no solution adduct is used.

The "grafting onto" approach provides for the preparation of the present polymer brushes from pre-formed polymer chains having water-soluble or water-dispersible segments, the polymer chains having functional groups that react with the substrate surface. A variety of chain coupling techniques are useful to attach the pre-formed polymer chains to the substrate surface, either by covalent bonding or physical interaction. Covalent coupling is, for example, achieved by chemical reaction between electrophilic entities (such as, for example, acyl halides, isocyanates, sulfonyl halides, activated esters and the like) and nucleophilic entities (such as, for example, hydroxyl, amine, thiol and the like), the nucleophilic or electrophilic groups being present either on the water-soluble or water-dispersible segment or the substrate surface. Many other techniques known by those skilled in the art, which result in bond formation between carbon atoms, heteroatoms, metals and combination thereof are also applicable. The immobilization of blocks copolymers or graft copolymers is also an efficient way to prepare polymer brushes, whereby these block/graft copolymers comprise (i) water-soluble or water-dispersible segments at their termini (as defined herein), or as pendant entities, and (ii) one or more other segments which exhibit some affinity towards the substrate surface. Such segmented macromolecules can be anchored through, for example, hydrophobic interaction, hydrogen bonding or coulombian interaction. Segmented polymers can be chosen among the following examples: polystyrene-b-polyethyleneoxide, polyethyleneoxide-b-polypropyleneoxide-b-polyethyleneoxide, polymethylmethacrylate-b-polyethyleneoxide, polystyrene-b-poly(meth)acrylic acid, polystyrene-b-polyvinyl pyridine, polydimethysiloxane-b-polyethyleneoxide, polydimethylaminoethylmethacrylate-b-polymethacrylic acid and the like. According to another method, polymer brushes can also be built from polymer particles stabilized by hydrophilic polymers that are deposited on the surface and allowed to fuse in a coherent film by the action of drying.

The grafting process occurs gradually over time periods of hours to days, and the grafted layer is built up continuously. The rate of grafting also increases with the concentration of dissolved polymer. Generally, a limiting value of the brush thickness is approached at long times, but by stopping the grafting process at an earlier selected time it is possible to control the ultimate grafting density, so long as this is less than the ultimate limiting value. While this makes it impossible to access very high grafting densities, because the grafting process is self-limiting, as discussed herein high grafting densities are typically unsuitable, as they lead to reduced accessibility of the binding sites. It will be understood by those of skill in the art that "grafting" is used in multiple ways in this specification, and that "grafting density" does not require use of the "grafting onto" approach to surface preparation.

Surface-bound Initiators/Spacer Molecules

The above-noted polymer segments may be bound to the surface through covalent bonding or non-covalent bonding (such as, for example, electrostatic, hydrophobic or affinity binding interactions). In other embodiments, there may be a functional group attached to the polymer segment that is designed to interact with the surface to bind the segment to the surface. For example, the polymer segment may include an —SH group that will interact with certain surfaces, such as gold, to bind it to the surface; other embodiments include Langmuir-Blodgett films, lipid monolayers and lipid bilayers, for the attachment of the polymers.

However, in one embodiment, the polymer segments are attached to the surface functionalities by means of a surface bound initiator which is suitable for free radical polymerization; that is, the polymer segment is attached as a result of, for example, the reaction of monomer with an initiator (such as one suitable for free radical polymerization) that has first been attached to the surface functionalities. The initiator for the free radical polymerization of the polymer attached to the surface may be any known initiator for water-soluble or water-dispersible monomers. Known initiators include peroxides and the like. In other embodiments, a free radical control method is employed, such as a reversible chain transfer process, atom transfer radical polymerization or stable free radical controlled polymerizations. In the specific case of the use of nitroxide control agents, the nitroxide may serve as a control agent or as a chain transfer agent to control molecular weight.

Figure 2:
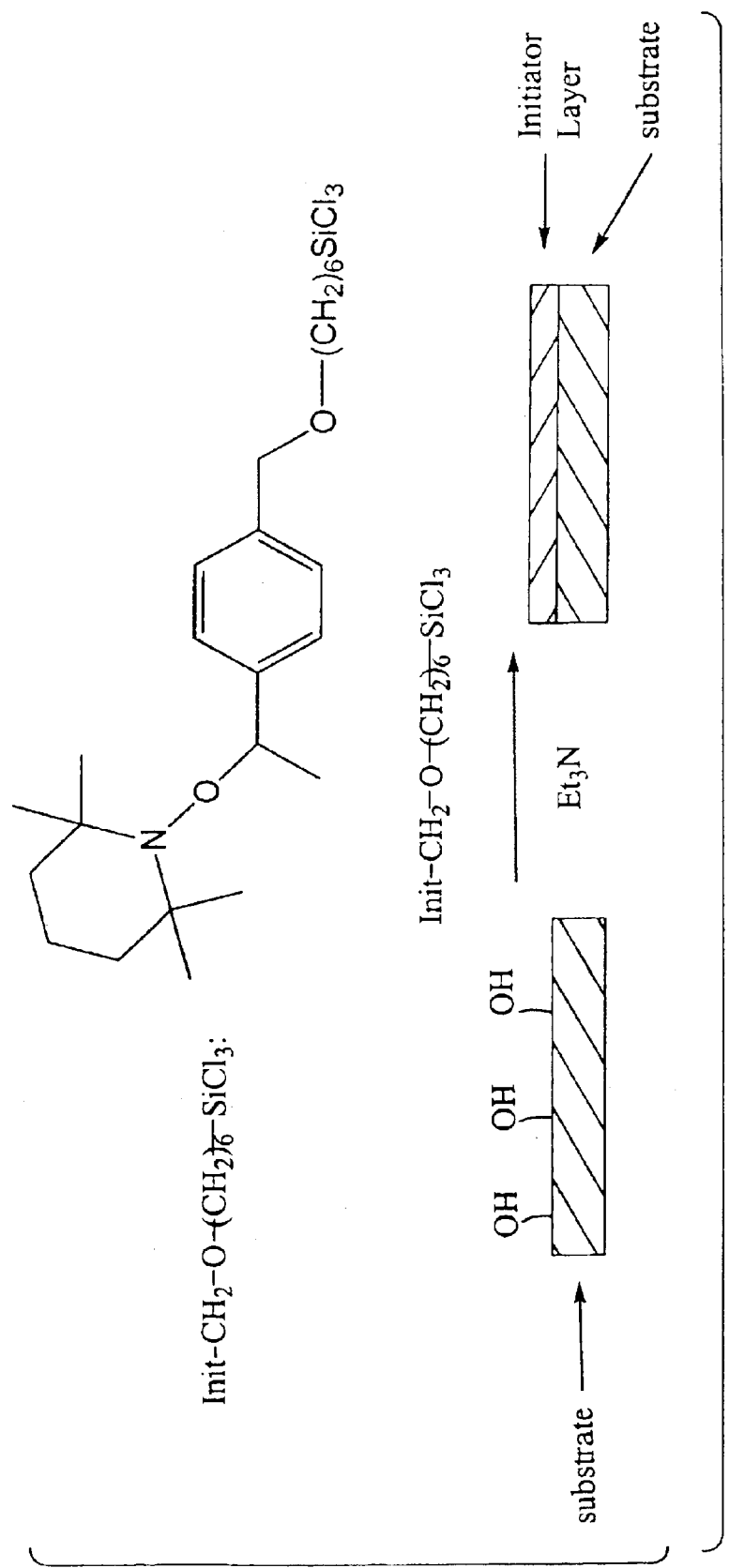
FIGS. 2–5 are schematic drawings showing a method for forming surface-bound polymers having water-soluble or water-dispersible segments bearing functional groups available for bonding to various probe molecules.

When a surface bound initiator is employed, preferably the initiator is covalently bound to the surface of the substrate and is capable of initiating a free radical polymerization reaction with living-type kinetics. A surface-bound initiator may be characterized by the general formula:

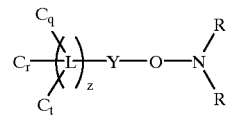

wherein: C is a functional moiety on the surface of the substrate; L is a linker group capable of bonding to at least one C moiety; q, r, and t, independently, are 0 or 1; z is 0 or, preferably, 1; O is oxygen, N is nitrogen; and, R is a substituent, as further described herein. The remainder of the structure (i.e., —Y—O—NR$_2$) is an initiator-control agent adduct, described in greater detail below. When bound to the surface, at least one of q, r or t must be 1. The C moiety is a portion of the surface functionality and is typically oxygen because, as shown in FIG. 2, hydroxyl groups are typically found on the surface of commonly used substrates such as silicon wafers and glass. However, it is possible to bond the initiator to other surface moieties as well. The above formula show the initiator-control agent adduct attached to the substrate surface. For addition to the surface, the starting molecule takes the form (L)$_z$—Y—O—NR$_2$, with the same definitions for L, Y, R and z.

The linker group, L, is optional; that is, the initiator may be directly bound to the substrate surface. However, in some embodiments a linker may be preferred because it helps space the polymer chains away from the substrate surface, which may enhance the accessibility of functional groups on the polymer chains. The length and identity of the linker group is selected depending on the type of surface to which the initiator will be bound and the identity of the particular initiator. In addition, the linker group moieties preferably do not substantially interfere with the polymerization reaction.

As generally indicated above, linkers have an end-group capable of binding to the surface of the substrate, and may be selected from the group consisting of substituted alkyl, heteroalkyl and polyethylene glycol. When substituted alkyls are used, it is preferred that one end of the alkyl chain is substituted with a silyl group.

Figure 3:
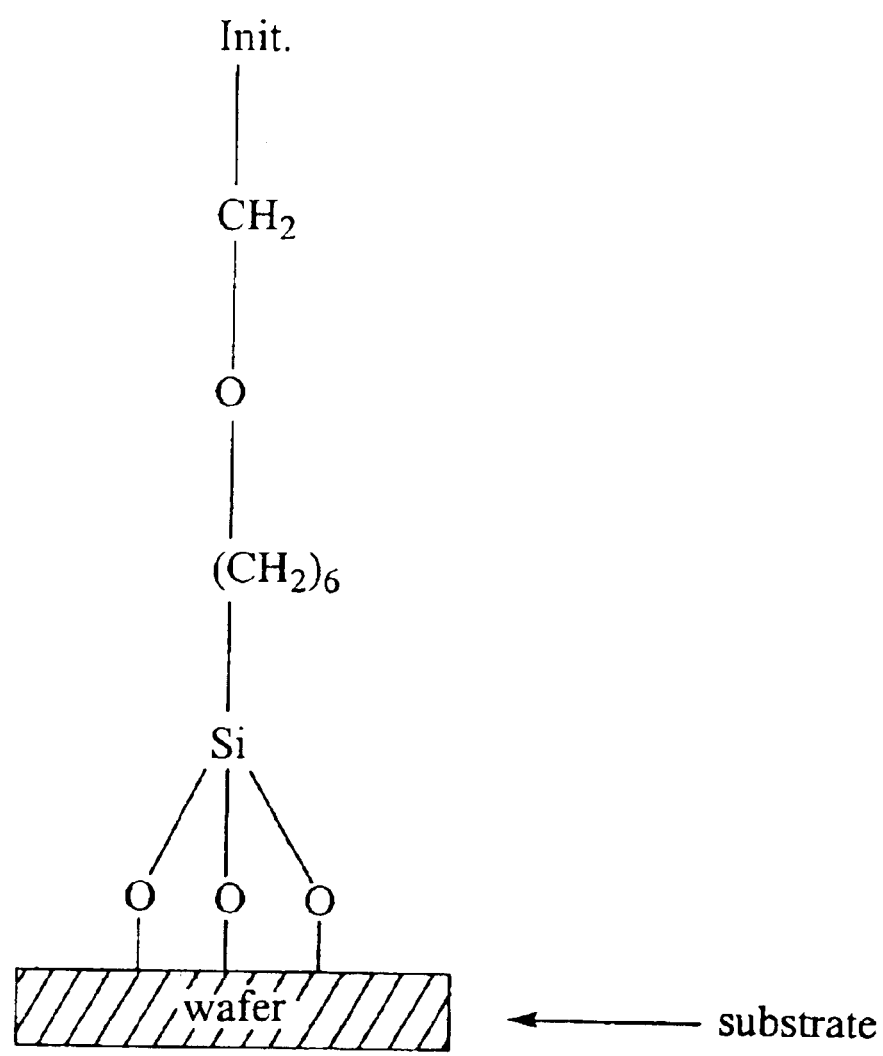
Figure 4:
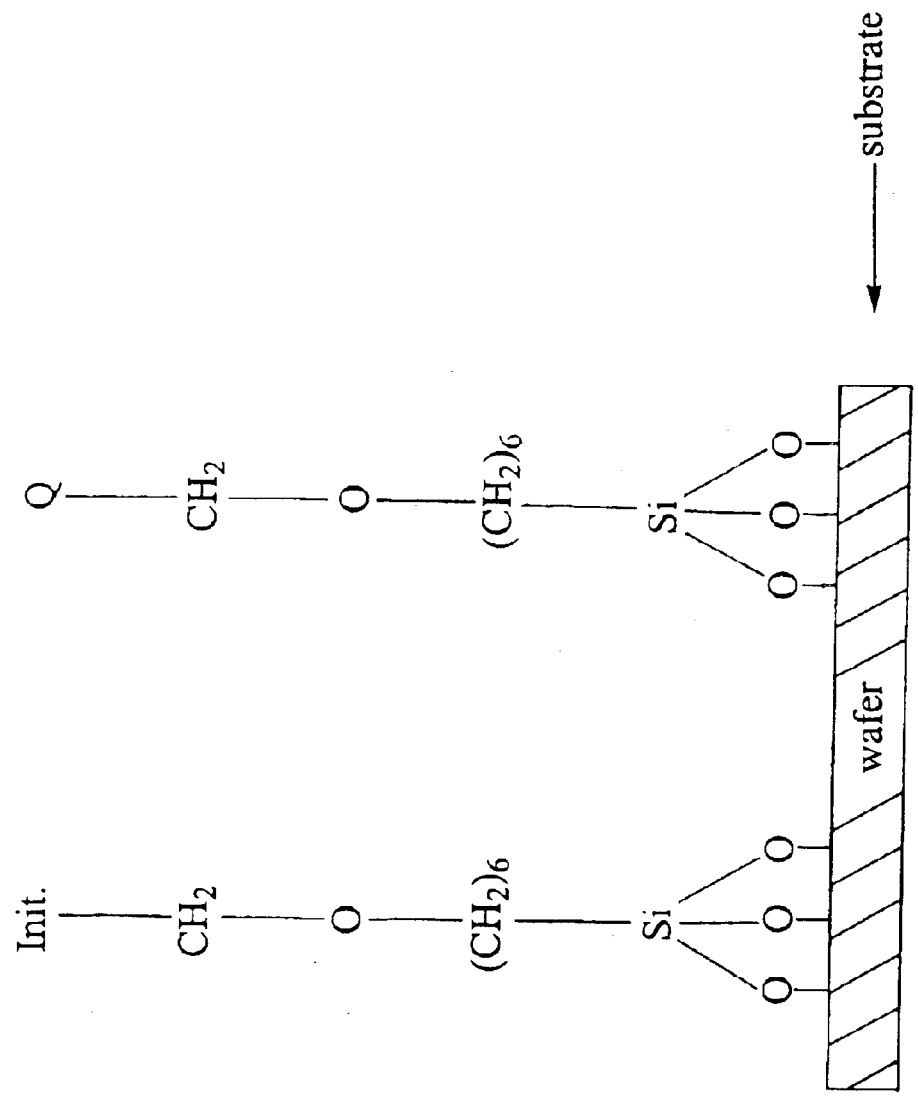

In a particularly preferred embodiment, wherein Si or a $SiO_2$ based surface are used (e.g., such as silicon, silica, fused silica glass, quartz or other silicon based glasses), it is especially desirable for the linker group to include a silicon atom, as shown in FIGS. 2–4, because silicon bonds readily to such surface hydroxyl groups. Additional spacing may be provided by an alkyl or alkoxy group separating the silicon atoms from the initiator-control agent adduct. Linear alkyl and alkoxy groups are preferred because they do not interfere with the subsequent free radical polymerization. To maximize the stability of the bond between the surface hydroxyl groups and the silicon atom, it is desirable to include at least three atoms, and preferably up to about eight atoms, in the group separating the silicon atom from the initiator-control agent adduct.

As shown in FIGS. 3 and 4, the initiator is bonded to the substrate surface through the linker atom through at least one attachment site, but preferably to two or (as shown in the figures) three sites of attachment. As further illustrated below (see, e.g., "Stability Test"), bonding to multiple surface moieties advantageously increases stability by ensuring that the initiator will remain tethered to the substrate even if one or more bonds between the linker atom and the surface moieties were to break. Although covalent bonding of the polymer to the surface (e.g., via the linker, L and initiator fragment, Y) is the preferred embodiment, in other embodiments, the polymer is associated with the surface through bonding other than covalent bonding. Alternative non-covalent binding techniques can be selected from among ion pair association, hydrophobic interaction, metallic complexes, multiple H-bonding systems and other host-guest interactions.

In order to control, adjust or optimize the accessibility of functional groups on water-soluble (or water-dispersible) segments of the surface-bound polymer chains to probe molecules, it is important to control the surface grafting density of these segments. As described in more detail below, the desired grafting density, or spacing between these segments, is at least in part a function of the size of the probes to be attached to the functional groups, the grafting density decreasing as the probe size increases in order to prevent, for example, steric hinderance from impeding probe attachment. One useful way of accomplishing this objective is through the use of "dummy" or "spacer" molecules bound to the surface, as shown in FIG. 4. In one embodiment, these surface-bound spacer molecules are very similar to the surface-bound initiator molecules, so that the chemistry of the polymerization reaction is not substantially affected. In some embodiments the spacers are characterized by the formula:

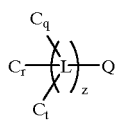

where C is a functional moiety on the surface of the substrate (as defined above); q, r, and t, independently, are 0 or 1; L is a linker group (as defined above) that is capable of bonding to at least one C moiety; z is 0 or 1; and Q is a group that is substantially incapable of initiating free radical polymerization. Q can, for example, be selected from the group consisting of alkyl, substituted alkyl, alkoxy, substituted alkoxy, aryl, substituted aryl, and combinations thereof. When bound to a surface, at least one of q, r or t is 1. The above formula shows the spacer or dummy molecules attached to the surface. Thus, the spacer or dummy molecules may be added to the surface by using a molecule that fits the formula $(L)_z$—Q, with the same definitions for L, Q and z.

Because these surface-bound dummy or spacer molecules are incapable of reacting with a monomer or otherwise binding a water-soluble (or water-dispersible) segment as described herein, they perform the role of neutral space-holders, thereby allowing control of the grafting density of the water-soluble (or water-dispersible) segments on the surface. In some embodiments, this control is important to prevent the grafting density of these surface-bound segments from becoming so high the functional groups are not accessible for binding probes and/or the probes are not accessible to the sample components (i.e., the "target" molecules of the sample). The relative concentration of surface-bound initiator (or surface-bound initiator-control adduct) to surface-bound spacer molecules can be selected based upon the surface grafting density desired or needed for a particular application. For example, in some embodiments the concentration of surface-bound spacer molecules exceeds that of the surface-bound initiators (or initiator-control adducts), the ratio ranging from about 1000:1 to about 1:1 (i.e., about 1000:1, 500:1, 100:1, 50:1, 25:1,10:1, 5:1, etc.), while in other embodiments the concentration of surface-bound initiators exceeds that of the surface-bound spacer molecules, the ratio ranging from about 100:1 to about 1:1 (i.e., about 100:1, 50:1, 25:1, 10:1, 5:1, 3:1, etc.). In other words, in some embodiments the dummy to initiator ratio can range from 100 mol % initiator (i.e., no dummy molecules present) to 0.001 mol % initiator. Typically, however, the dummy to initiator ratio ranges from about 95% initiator/5 mol % dummy to about 1 mol % initiator/99 mol % dummy. Depending upon the molecular weight of the polymer chains attached to the substrate surface and the molecular size of, for example, the probe to be attached, this ratio may range from about 75 mol % initiator/25 mol % dummy to about 10 mol % initiator/ 90 mol % dummy.

The surface density of initiator or initiator-control adducts can be expressed as a normalized value representing the ratio of the available substrate surface functionalities having an initiator (or initiator control adduct) attached thereto to the total number of such available substrate surface functionalities. For example, when substantially all of the available substrate surface functionalities have an initiator (or initiator control adduct) attached, then the surface is considered to have a polymer chain population distribution of about 1 (assuming each surface bound initiator acts as a site for the initiation of a polymer chain). Further, when about 50% of the available surface functionalities have an initiator (or initiator control adduct) attached and the remainder of the surface functionalities have a dummy molecule attached, then the surface is considered to have a polymer chain population distribution of about 0.5. Similarly, when about 25% of the available surface functionalities have an initiator (or initiator control adduct) attached and the remaining 75% of the surface functionalities have a dummy or spacer molecule attached, then the surface is considered to have a polymer chain population distribution of about 0.25. Moreover, the population distribution of initiator or initiator-control adducts may be estimated, as a first approximation assuming equally competitive binding, based on the relative amount of dummy or spacer molecules to, when present, the amount of initiator (or initiator-control adduct) in the polymerization mixture. In this manner, those of skill in the art will appreciate how to adjust the population distribution of the polymer chains on the substrate surface, as may be desirable for a particular sensor or application. The chain population distribution, based on the fraction of initiator on the surface to the total number of surface sites (assuming all are occupied by either initiator or dummy molecules), may range from about 0.01 to about 1, more typically from about 0.2 to about 0.8.

In this regard it is to be noted that, as further described herein (see, e.g., discussion below under the heading "Density Calculation"), grafting density may also be calculated based on the molecular weight of the polymer chain segments and the thickness of the polymer layer on the substrate surface. Generally speaking, segment grafting density may range, for at least some embodiments, from greater than about 0.001, 0.01, 0.1 or event 1 picomole/cm² to greater than about 100 picomoles/cm² or more. Typically, however, the segment grafting density will range from less than about 1 picomole/cm² to about 100 picomoles/cm², from about 2 to about 75 picomoles/cm², from about 5 to about 55 picomoles/cm², from about 10 to about 45 picomoles/cm², or from about 15 to about 35 picomoles/cm².

Initiators

As noted above, and as shown in FIGS. 2–5, in one embodiment the initiator is preferably capable of initiating free radical polymerization with living-type kinetics. Useful molecules for this purpose are initiator-control agent adducts that decompose in situ to yield a control agent and a free radical initiator. Control agent is generally used herein to refer to a molecule that comprises a free radical that cannot initiate a polymerization under polymerization conditions, which are discussed herein. The initiator-control agent adduct can be characterized by the general formula:

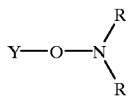

where Y is a residue capable of initiating a free radical polymerization upon cleavage of the Y—O bond (and is more fully defined below) and each R, which may be the same or different, is independently selected from the group consisting of hydrocarbyl and substituted hydrocarbyl. Optionally, the two R groups may be joined together; that is, each R may be linked to the other by, for example, a hydrocarbylene or heterohydrocarbylene moiety, forming a heterocyclic ring structure with the nitrogen atom. Many free radical control initiators of this type have been disclosed previously, for example, in U.S. Pat. No. 4,581,429, WO 98/30601, WO 96/24620, and WO 99/03894, each of which is incorporated herein by reference. Again, the above formula shows the initiator-control agent adduct without the linker. For addition to the surface with a linker, the starting molecule takes the form $(L)_z$—Y—O—$NR_2$, with the same definitions for L, Y, R and z.

More preferably, the control agents used in this invention are nitroxide control agents having an alpha-destabilizing moiety, with alpha-hydrido nitroxide control agents being particularly preferred. Particularly preferred control agent-initiator adducts capable of generating these control agents can be characterized by the general formula:

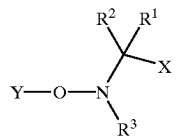

where each of $R^1$, $R^2$ and $R^3$ may be the same or different, independently selected from the group consisting of hydrogen, straight chain, branched or cyclic substituted or unsubstituted hydrocarbyl groups, including, for example, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof. $R^1$ and $R^2$ may be joined together in a cyclic ring structure; likewise, $R^2$ and $R^3$ may be joined together in a cyclic ring structure that may have fused with it another saturated or aromatic ring. It is to be noted that the above formula shows the initiator-control agent adduct without the linker. For addition to the surface with a linker, the molecule takes the form $(L)_z$—Y—O—$NR^3(CR^1R^2X)$, with the same definitions for L, Y, $R^1$, $R^2$, $R^3$, X and z.

X is a moiety that is capable of destabilizing the free radical such as, for example, a hydrogen or phosphate group. In this regard it is to be noted that by "destabilizing moiety" or "capable of destabilizing" it is meant that the moiety, "X", allows the free radical to destabilize, decompose, destroy, or otherwise remove itself from the reaction (e.g. spontaneously or by interaction with another such control agent), or to be destabilized, be decomposed, be destroyed or be removed from the reaction by the addition of a reagent.

It is to be noted, however, that when X is hydrogen, preferably the $R^3$ moiety is selected from among the group such that, relative to the nitrogen atom, no alpha hydrogens are present in $R^3$. Stated another way, with regard to the preferred nitroxide control agent-initiator adducts, generally represented by the above structure, it is preferred that only one hydrogen atom is alpha to the nitrogen atom. Accordingly, when $R^3$ is alkyl, for example, it is preferred that $R^3$ be a tertiary alkyl moiety. Furthermore, when X is hydrogen, it is preferred that $R^1$ and $R^2$ be other than hydrogen, as well.

For the aqueous solution polymerization, it is preferred that one of the R groups ($R^1$, $R^2$ or $R^3$) includes a water-solubilizing group, such as sulfonate, sulfate, carboxylate, hydroxyl, amino, ammonium and the like, to enhance the solubility of the control agent. The presence of monomer in the reaction mixture can, in some cases, also enhance the solubility of the control agent.

In more specific embodiments, each $R^1$, $R^2$ and $R^3$ is independently selected from a group consisting of alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl and silyl. Specific examples of $R^1$, $R^2$ and $R^3$ are methyl, ethyl, propyl, butyl, cyclopentyl, cyclohexyl, cyclooctyl, phenyl, benzyl, trimethylsilyl, those specific moieties listed in the above definitions and the like. In alternative embodiments, $R^1$, $R^2$ or $R^3$ may include a water-solubilizing group, such as $SO_3G$, where G is Na, K and the like. In a preferred embodiment, $R^1$ is an aryl (such as phenyl), $R^2$ is an alkyl (such as isopropyl) and $R^3$ is either an alkyl or a heteroalkyl (such as tert-butyl or $Me_3SiOCH_2(CH_3)_2C$). In an alternative preferred embodiment, $R^1$ is aryl (such as phenyl), $R^2$ is a cycloalkyl (such as cyclohexyl or cyclopentyl) or a tertiary alkyl (such as tert-butyl) and $R^3$ is either a tertiary alkyl or a heteroalkyl (such as tert-butyl or $Me_3SiOCH_2(CH_3)_2C$). In still another preferred embodiment, $R^1$ is a substituted alkyl (such as $NC(CH_3)_2C$) and $R^2CNR^3$ form a cyclic ring structure.

Y is a residue capable of initiating free radical polymerization upon homolytic cleavage of the Y—O bond, including, for example, alkyl, substituted alkyl, alkoxy, substituted alkoxy, heteroalkyl, substituted heteroalkyl, aryl, and substituted aryl residues. Use of such adducts can eliminate concerns about the speed of initiation of polymer chains, effectively initiating all polymer chains at substantially the same time upon addition of the adduct to the monomer under polymerization conditions. The adducts may be prepared by methods known in the art, such as those disclosed in WO 99/03894, which is incorporated herein by reference. In another such embodiment, the control agent is generated in situ from the nitrone precursor, as is also discussed in WO 99/03894. The adducts are, for polymerization in aqueous solution, preferably water soluble, or at least water soluble in the presence of the monomer.

In another embodiment, the adducts useful in this invention encompass compounds having a monomer, oligomer or polymer disposed between the Y residue and the oxygen atom of the adduct, as shown in the formula below. Thus, embodiments including compounds of the structure shown in this formula are within the definition of "adduct" as that term is applied to the invention; that is, the growing polymer chain, as well as the "capped" chain, can themselves be considered adducts (with Y'—(M)$_n$—being considered the Y moiety). An adduct comprising an oligomer or polymer of this invention may be characterized by the formula:

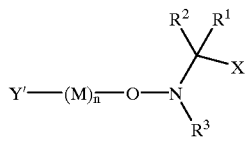

where $R^1$, $R^2$, $R^3$ and X have the above-recited meanings and scope, and Y' can be the same as Y as recited above; M is one or more monomer units selected from the monomers described herein, and n is zero, 1, or greater than 1. Thus, for example, when n is zero, the compound of the formula collapses to the compound of the previous formula. When n equals 1, the compound of this formula can be considered a first-monomer adduct. When n is 2 or more, the compounds of this formula are considered to be oligomer adducts or polymer adduct. All of such various adducts are capable of initiating the free radical polymerizations of the invention. The above formula shows the initiator-control agent adduct without the linker. For addition to the surface with a linker, the molecule takes the form $(L)_z$—Y—α—$(M)_n$—$ONR^3$ $(CR^1R^2X)$, with the same definitions for L, Y, $R^1$, $R^2$, $R^3$, X and z. If attached to the surface, the previously defined C would be added to this formula.

It is frequently convenient to generate the Y (or Y') radical in the presence of monomer and control agent, and to isolate an adduct where n ranges from 1 to about 5, is preferably 2 or 3, and is more preferably 1. These are isolable compounds that can be easily purified and used in subsequent polymerization processes of the invention.

The Polymerization Process

In a preferred embodiment of the present invention, the polymerization reaction is a controlled, living free radical polymerization reaction of the type generally described in Husseman et al., *Macromolecules* 1999, 32, 1424–31, the contents of which are hereby incorporated by reference.

More specifically, the substrate surface is analyzed to estimate or specifically determine the amount of surface functionalities that are available for binding the polymer chains via one of the methods discussed herein. If necessary, the surface is modified to adjust the amount (e.g., concentration per unit area or location on the surface) and type of surface functionality, for example by acid treatment or coating the surface. After the surface is prepared, in accordance with various embodiments of the present invention, the initiators, initiator-control adducts and/or dummy or spacer molecules may be attached to the surface via the surface functionalities; that is, once the substrate surface has been prepared, one or more of these may be attached to the surface or, alternatively, added in solution at some point during the polymerization process (as further described in detail below in the general procedure portion of the example section). In those embodiments wherein the surface is to be further modified, typically before doing so the desired surface grafting density of the polymer chain segments is determined.

In those embodiments wherein the substrate surface is further modified prior to initiation of polymerization, such as by the attachment of initiators or initiators-control adducts and/or dummy molecules to the substrate surface, the substrate surface is generally referred to herein as a "derivatized surface." Subsequently, the derivatized surface is placed into a polymerization system that contains the desired monomers. As discussed below, unbound or "free" initiators or initiator-control adduct, which generally refers to initiators or initiator-control adducts that are not bound to the substrate surface, can also be included in the polymerization system. Accordingly, in one embodiment the polymerization system includes at least the desired monomers, the derivatized surface and the unbound initiators or initiator-control adducts under polymerization conditions, while in a second embodiment no unbound initiators or initiator-control adducts are present in the polymerization system.

For controlled radical polymerizations generally, when present, the number of unbound initiators or initiator-control adducts may be greater than the number of bound initiators or initiator-control adducts. The addition of unbound initiators or initiator-control adducts, therefore, creates an overall concentration of control agent in the polymerization system which is believed to control the growth of both bound (insoluble) and unbound (e.g., typically soluble) polymer chains. In general, depending on the surface and the method used to polymerize the polymer, a useful range for the ratio of the number of unbound initiator or initiator-control agent adduct to number of surface bound initiator or initiator-control agent adduct is from about zero:1 to about $1 \times 10^7$:1. Thus, when the ratio is zero, there is no unbound initiator or initiator-control agent adduct. In those embodiments wherein unbound initiator or initiator-control agent adduct is present, preferably this ratio is not less than about 10:1, where the unbound initiator or initiator adduct is at least 10 times greater than the bound initiator or initiator adduct.

By having both bound and unbound adducts, polymerization results in the formation of both bound and unbound polymers. The unbound polymer can then be removed, e.g., by washing the derivatized substrate with water or other solvent to yield the article. As discussed elsewhere, the bound polymer chain ends may be modified, for example to remove the control agent and replacement of the same with a functionality. Also, it will be appreciated by those of skill in the art that only the derivatized surface, or a portion thereof, needs to be exposed to the polymerization system.

In other embodiments, the entire substrate may be immersed in the polymerization mixture.

Using both bound and unbound adducts overcomes the problem associated with many surface polymerizations of not being able to form a sufficient number of polymer chains bonded to the surface. Moreover, because both the bound and unbound polymers are formed under the same conditions, they can have substantially the same composition. Accordingly, the unbound polymer can be analyzed to determine properties such as molecular weight, extent of branching, etc. and thereby provide a convenient way of determining the properties of the bound polymer without disturbing the bound polymer. Furthermore, the molecular weight of the unbound polymer can be correlated with the thickness of the polymer layer on the surface. The amount of incorporated functional group containing co-monomer can be determined by $^1$H NMR spectroscopy of the unbound polymer.

It is to be noted, however, that "free" initiator is not required and, in some cases, may preferably be absent from the polymerization system. When free initiator is not present, the polymerization reaction may be controlled by using an unbound control agent in the polymerization mixture such as, for example, a nitroxide radical control agent having the general formula:

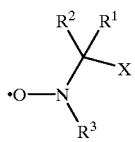

In this approach, polymer growth is monitored by measuring the polymer layer thickness (e.g. by ellipsometry). The molecular weight may then be calculated from the thickness of a substrate with a known density of initiating sites. The appropriate concentration of the stable free radical to be added to the polymerization mixture may be determined empirically, or it may be deduced from ESR experiments performed.

Conducting the present process in this manner (i.e., in the absence of free initiator) is advantageous for a number of reasons. For example, because initiator is not present in solution, essentially no polymer is formed therein, which facilitates the washing procedure; that is, because essentially no polymer is formed in the solution, repeated washings are not required to remove the "free" polymer from the surface. In addition, the approach is comparably more cost effective as a result of the fact that significantly less of what is typically very expensive polymerization initiator can be used.

When no "free" initiator or initiator-control agent adduct is used, chain length may be tuned by the concentration of control agent in solution and the reaction time. For example, high concentrations of control agent will need longer reaction times in order to grow polymers of a given molecular weight. In general, depending upon the surface and the polymerization method used, a useful range of control agent concentration is 1'10−8 mol/L to about 1×10$^{31}$ $^1$ mol/L. The control agent is preferably the nitroxide radical control agent depicted above. However, other methods may be employed, such as ATRP or iniferter, where the control agent is generally a ligated metal at a high oxidation state or a dithio compound, respectively. When using the iniferter process, the surface-bound initiator has a general formula:

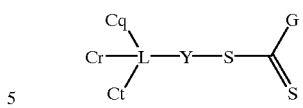

wherein S is sulfur and L, Y, C, q, r and t are as defined herein. Additionally, G is nitrogen or oxygen (such as in the case of NR$^2{}_2$ and OR$^3$, respectively, R$^2$ and R $^3$ being as defined herein but typically being hydrocarbyl). The control agent has the general formula:

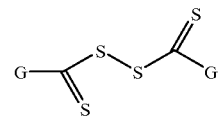

wherein G is as defined above. The reaction is triggered by UV initiation. Such an approach is further described herein with reference to nitroxide-mediated living free radical polymerizations.

If desired, one or more accelerators may be added to the reaction mixture. Examples of suitable accelerators include alkylating and acylating agents, Lewis Acids, ketones, aldehydes, anhydrides, acid esters, imides, oxidants and reducing agents. Specific accelerators include acetic acid, acetic anhydride, camphor sulfonic acid, other sulfonic acids, acetole (1-hydroxyacetone) and the like. Other accelerators useful herein are recited in Hawker et al., "Development of a New Class of Rate-Accelerating Additives for Nitroxide-Mediated 'Living' Free Radical Polymerization," Tetrahedron, Vol. 53, No. 45, pp. 15225–15236 (1997), which is incorporated herein by reference.

Polymerization reaction conditions may be adjusted to control the polymer length and architecture. Polymerization conditions include a temperature in the range of from about minus 40° C. to about 300° C., preferably between about 25° C. and about 200° C., more preferably between about 50° C. and about 150° C., and most preferably between about 70° C. and about 130° C. Alternatively, the temperature may be between about room temperature and 250° C. Polymerization conditions also include a pressure between about ambient pressure up to about 100 atmospheres. The atmosphere may also be one of the polymerization conditions, and the atmosphere may be air, nitrogen, argon or another suitable atmosphere. Polymerization conditions also include the time for reaction, which may be from about 0.5 hours to about 72 hours, preferably in the range of from about 1 hour to about 24 hours, more preferably in the range of from about 2 hours to about 12 hours. The ratios of components (e.g., initiators/control agents, monomers and accelerators) in the polymerization mixture may be important. The initiator to free radical control agent ratio (with the assumption that the amount of initiator is approximately equivalent to the number of radicals produced) is typically in the range of from about 1:0.1 to about 1:4, more preferably the range of from about 1:0.3 to about 1:2 and most preferably the range of from about 1:0.4 to about 1:1.6. Another ratio that may be controlled is the monomer to initiator (or initiator-control adduct) ratio, which typically is in the range of from about 10:1 to about 10,000:1, more preferably the range of from about 100:1 to about 10,000:1 and most preferably the range of from about 100:1 to about 1000:1. When an accelerator is present the ratio of free radical control agent to accelerator is typically in the range of from about 1:0.1 to about 1:4, more preferably the range of from about 1:0.3 to about 1:2 and most preferably the range of from about 1:0.4 to about 1:1.6.

It is to be noted here that, in the case of living-type polymerizations when an excess of unbound initiator or initiator-control agent (as discussed above) is used, it is this excess of unbound initiator or initiator-control agent that determines the monomer to initiator ratio, and thus the molecular weight of the polymer chain in solution as well as on the surface.

A single substrate may have more than one type of polymer chain, including polymer chains with different types, numbers and spacing of functional groups, polymer chains with different molecular weights, etc. In addition, different areas of the substrate surface may feature different arrangements and/or densities of polymer chains. In this way, a single substrate can, if desired, perform multiple analytical operations, making the derivatized substrates particularly useful for complex nucleic acid hybridization studies.

The polymer architecture (including, for example, the identity and length of the polymer chains; the extent, if any, of branching within the chain; the concentration of functional groups, the thickness of the resulting polymer layer, etc.) may be carefully controlled and selected depending on the desired characteristics of the end product. Within these parameters, a large degree of design flexibility is available. The polymers, for example, can be homopolymers or copolymers prepared from two or more different monomers. The copolymers, in turn, can be random copolymers, block copolymers or graft copolymers. To improve the stability of the water-soluble (or water-dispersible) segment attachment to the surface (or to the linker), a first part of the polymer chain containing the water-soluble (or water-dispersible) segment can be crosslinked and then linear chains may be grown from the crosslinked base. In order to perform this crosslinking a bi-functional monomer may be used.

It is to be noted in this regard, however, that if crosslinking is employed, the crosslinking sites should be spaced sufficiently far from the water-soluble or water-dispersible segments and near the substrate surface in order to ensure maximum mobility of these segments.

As used herein, "block copolymer" refers to a polymer comprising at least two segments of differing composition; having any one of a number of different architectures, where the monomers are not incorporated into the polymer architecture in a solely statistical or uncontrolled manner. Although there may be three, four or more monomers in a single block-type polymer architecture, it will still be referred to herein as a block copolymer. In some embodiments, the block copolymer will have an A-B architecture (with "A" and "B" representing the monomers). Other architectures included within the definition of block copolymer include A-B-A, A-B-A-B, A-B-C, A-B-C-A, A-B-C-A-B, A-B-C-B, A-B-A-C (with "C" representing a third monomer), and other combinations that will be obvious to those of skill in the art. In another embodiment, the block copolymers that may be used in the sensors of this invention include one or more blocks of random copolymer together with one or more blocks of single monomers. Thus, a polymer architecture of A-J, A-J-B, A-B-J, A-J-B-J-C, J-J'-J, etc. is included herein, where J and J' are random blocks of monomers A and B or of monomers B and C. Moreover, the random block can vary in composition or size with respect to the overall block copolymer. In some embodiments, for example, the random blocks J or J' will account for between 5 and 80% by weight of the mass of the block copolymer. In other embodiments, the random blocks J or J' will account for more or less of the mass of the block copolymer, depending on the application. Furthermore, the random block may have a compositional gradient of one monomer to the other (e.g., A:B) that varies across the random block in an approximately algorithmic fashion, with such algorithm being either linear having a desired slope, exponential having a desired exponent (such as a number from 0.1–5) or logarithmic. The random block may be subject to the same kinetic effects, such as composition drift, which would be present in any other radical copolymerization and its composition, and size may be affected by such kinetics, such as Markov kinetics. Any of the monomers listed elsewhere in this specification may be used in the block copolymers. A "block" within the scope of the block copolymers of this invention typically comprises about 10 or more monomers of a single type (with the random blocks being defined by composition and/or weight percent, as described above). In preferred embodiments, the number of monomers within a single block is about 15 or more, about 20 or more or about 50 or more. However, in an alternative embodiment, the block copolymers of this invention include blocks where a block is defined as two or more monomers that are not represented elsewhere in the copolymer. This definition is intended to encompass adding small amounts of a second monomer at one or both ends of a substantially homopolymeric polymer. In this alternative embodiment, the same copolymer architectures discussed above apply. This definition is therefore intended to include telechelic polymers, which include one or more functional end groups capable of reacting with other molecules. Thus, generally, a telechelic polymer is a block copolymer within the definitions of this invention. The functional groups present at one or both ends of a telechelic polymer may be those known to those of skill in the art, including, for example, hydroxide, aldehyde, carboxylic acid or carboxylate, halogen, amine and the like, which have the ability to associate or form bonds with another molecule.

The polymer chains may be linear or non-linear. Examples of non-linear molecules include branched and star polymers. The star molecules typically have anywhere between 2 and 12 arms growing from a common core, although structures having more than 12 arms can also be prepared. Branched polymer chains include polymer molecules in which there are side branches of linked monomer molecules protruding from various central branch points along the main polymer chain. Hence a branched polymer molecule can include two or more polymeric segments covalently bonded to each other at a point other than their common ends—either directly (e.g., through functional groups on side chains thereof), or indirectly through a linking moiety. The various "branches" of branched polymers can include polymeric segments having substantially the same or different repeat units, and can themselves be homopolymers or copolymers. The extent of branching is selected based upon the particular application for which the surface-bound polymers are intended.

With respect to crosslinking it is to be noted that, it is typically preferred for the water-soluble (or water-dispersible) segment to have a single point of attachment to the substrate surface (i.e., having a single terminus, as defined herein, attached to the surface) and be substantially free of covalent crosslinking, and preferably all crosslinking. Compared to the permanent entanglements present in a chemically crosslinked gel layer, for example, the entanglements present in a brush composed of singly attached polymer are relatively short lived. These entanglements constantly form and dissipate, so that any loop in the polymer layer which blocks the motion of a biomolecule in a particular direction is temporary. In contrast, in a chemically crosslinked gel, a loop or other obstructing entanglement can act as a permanent impediment or barrier to the movement of a biomolecule through the layer. Thus, in the case of a singly end-grafted brush, penetration of large biomolecules into the brush is facilitated by the dissipation of these entanglements in advance of the moving biomolecule. Therefore, a polymer layer comprised of singly end-attached, non-crosslinked water-soluble (or water-dispersible) segments offers many advantages in comparison to the alternative structures, such as cross linked gel layers or polymer pseudo-brushes where each chain has multiple points of attachment.

The polydispersity index of the polymer can generally range from about 1 to about 100. The polydispersity may be adjusted depending on the application. In the case of living polymerizations, it typically ranges from about 1 to about 2.5, while under certain conditions it may be less than about 2 (range from about I to about 2), with values of less than about 1.8, 1.6, 1.5, 1.4, 1.3, 1.2, or even about 1.1 being attainable. Hence, it is possible to control process conditions to achieve a polydispersity index ranging from about 1 to about 1.8, from about 1 to about 1.6, or from about 1 to about 1.5. In a controlled polymerization, the polydispersity typically is less than about 2.

The molecular weight of the polymer chains is adjusted to suit the needs of a particular sensor or application, as discussed in connection with FIG. 1. In general, the molecular weight is adjusted to be sufficiently high such that the functional group-bearing segments (i.e., the water-soluble or water-dispersible segments) are spaced from the surface to the point where they simulate the behavior of a polymer chain in solution with respect to the ability to bond probe molecules to the functional groups. As discussed herein, the polymer chain preferably has a water-soluble or water-dispersible segment that has a molecular weight of at least about 1,000, but can also have a molecular weight of not less than about 2,000, not less than about 10,000, not less than about 50,000, or not less than about 100,000. The incorporation of the functional-group containing monomer may also be calculated relative to other monomer(s) present in the polymer chain. In this context, the relative mole percent of the functional-group containing monomer to other monomer (s) present in the polymer chain may be in the range of from about 1 to 100, more specifically about 2 to 50, without regard to the specific polymer architecture.

Unless otherwise specifically noted, the molecular weight values recited herein are weight-average molecular weights (as determined by size-exclusion chromatography, SEC, performed on polymer chains formed in solution during the polymerization process), based on correlation to narrow linear polystyrene standards. For example, a SEC-observed Mw value of 100,000 means that the measured polymer has the same hydrodynamic volume as the polystyrene of the molecular weight 100,000 under the conditions used for both calibration and characterization (DMF+0.1% TFA) of all samples.

It is to be noted, however, that the actual molecular weight of the polymer may differ from the observed molecular weight, as determined by SEC. For example, in some cases the actual molecular weight may vary from the observed molecular weight of the polymer by at least about +/−10%, 25%, 50% or more. The actual molecular weight, as used herein, means the weight-average of the actual weight of polymer molecules in the polymer based on the actual atomic structure thereof. Because of the inherent difficulties in determining actual molecular weight, however, the actual molecular weight can be approximated by other suitable means. For example, for purposes of the present invention, the actual molecular weight can be approximated as the target molecular weight. The target molecular weight refers to the estimated molecular weight based on the total amount (e.g., moles) of monomer to be incorporated into polymer during the polymerization reaction, as determined by the amount (e.g., moles) of initiator, and the monomer to initiator ratio, assuming that each initiator starts one chain, and that all monomer is incorporated. In situations where initiator efficiency is about 0.9 or less, and/or monomer conversion is less than about 95%, then adjustments for the target molecular weight are made based on initiator efficiency and/or monomer conversion, respectively.

In other embodiments, characterization of the polymer bristle can be accomplished via cleaving the polymers from the surface of the substrate and subsequent analysis, as described above, including chromatography or nuclear magnetic resonance (NMR). The usefulness of this technique depends on the type of surface and the overall amount of polymer available from the cleavage step.

The resulting surface-bound polymer chains include water-soluble or water-dispersible segments having a molecular weight of at least 1,000, preferably at least 2,000 and even more preferably a molecular weight that is adjusted according to the desired length of the polymer chains, which, as discussed elsewhere herein, depends upon, inter alia, the application of the sensors. These segments may be located anywhere along the polymer chain, although they are preferably located at or near the free termini of the chains. These segments further contain functional groups to which probe molecules, described in greater detail, below, can be covalently or non-covalently bonded. Examples of useful functional groups for this purpose include —OH, —COOH, —NH$_2$, —SH, —SCN, —C(O)H, combinations thereof and the like. The selection of useful functional groups is dependent on the application of the sensor, generally, and can be adjusted with the proper selection of monomers. In order to adjust the number of functional groups on the bound polymers, the appropriate concentration of functional group containing monomer is added to the polymerization system, discussed above. Typically, the ratio of functional group containing monomer to non-functional group containing monomer is adjusted to a predetermined ratio prior to adding monomer to the polymerization system. Useful ranges of functional group containing monomer relative to the total amount (volume, mass or moles) of monomer added to the polymerization system include about 0.5% to about 99% function group containing monomer, more specifically from about 10% to about 90%, even more specifically about 15% to about 50% and most specifically about 15% to about 30%.

The polymers may be prepared from a variety of monomers. A particularly useful class of water-soluble or water-dispersible monomers features acrylamide monomers having the formula:

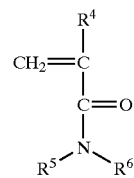

where $R^4$ is H or an alkyl group; and $R^5$ and $R^6$, independently, are selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, and combinations thereof; $R^5$ and $R^6$ may be joined together in a cyclic ring structure, including heterocyclic ring structure, and that may have fused with it another saturated or aromatic ring. An especially preferred embodiment is where $R^5$ and $R^6$, independently, are selected from the group consisting of hydroxy-substituted alkyl, polyhydroxy-substituted alkyl, amino-substituted alkyl, polyamino-substituted alkyl and isothiocyanato-substituted alkyl. In preferred embodiments, the polymers include the acrylamide-based repeat units derived from monomers such as acrylamide, methacrylamide, N-alkylacrylamide (e.g., N-methylacrylamide, N-tert-butylacrylamide, and N-n-butylacrylamide), N-alkylmethacrylamide (e.g., N-tert-butylmethacrylamide and N-n-butylmethacrylamide), N,N-dialkylacrylamide (e.g., N,N-dimethylacrylamide), N-methyl-N-(2-hydroxyethyl)acrylamide, N,N-dialkylmethacrylamide, N-methylolmethacrylamide, N-ethylolmethacrylamide, N-methylolacrylamide, N-ethylolacrylamide, and combinations thereof. In another preferred embodiment, the polymers include acrylamidic repeat units derived from monomers selected from N-alkylacrylamide, N-alkylmethacrylamide, N,N-dialkylacrylamide and N,N-dialkylmethacrylamide. Preferred repeat units can be derived, specifically, from acrylamide, methacrylamide, N,N-dimethylacrylamide, and tert-butylacrylamide.

Copolymers can include two or more of the aforementioned acrylamide-based repeat units. Copolymers can also include, for example, one or more of the aforementioned polyacrylamide-based repeat units in combination with one or more other repeat units. The monomers are selected such that the resulting copolymer contains water-soluble or water-dispersible segments. Examples of other such repeat units include those derived from monomers suitable for forming copolymers such as styrene, substituted styrene, alkyl acrylate, substituted alkyl acrylate, alkyl methacrylate, substituted alkyl methacrylate, acrylonitrile, methacrylonitrile, isoprene, butadiene, ethylene, vinyl acetate and combinations thereof. Functionalized versions of these monomers may also be used. Specific examples include methyl methacrylate, ethyl methacrylate, propyl methacrylate (all isomers), butyl methacrylate (all isomers), 2-ethylhexyl methacrylate, isobornyl methacrylate, methacrylic acid, benzyl methacrylate, phenyl methacrylate, methacrylonitrile, a-methylstyrene, methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile, styrene, glycidyl methacrylate, 2-hydroxyethyl methacrylate, 2-hydroxyethyl methylacrylate, hydroxypropyl methacrylate (all isomers), hydroxybutyl methacrylate (all isomers), N,N-dimethylaminoethyl methacrylate, N,N-diethylaminoethyl methacrylate, triethyleneglycol methacrylate, itaconic anhydride, itaconic acid, glycidyl acrylate, 2-hydroxyethyl acrylate, hydroxypropyl acrylate (all isomers), hydroxybutyl acrylate (all isomers), N,N-dimethylaminoethyl acrylate, N,N-diethylaminoethyl acrylate, triethyleneglycol acrylate, vinyl benzoic acid (all isomers), diethylaminostyrene (all isomers), α-methylvinyl benzoic acid (all isomers), diethylamino a-methylstyrene (all isomers), p-vinylbenzene sulfonic acid, p-vinylbenzene sulfonic sodium salt, trimethoxysilylpropyl methacrylate, triethoxysilylpropyl methacrylate, tributoxysilylpropyl methacrylate, dimethoxymethylsilylpropyl methacrylate, diethoxymethylsilylpropyl methacrylate, dibutoxymethylsilylpropyl methacrylate, diisopropoxymethylsilylpropyl methacrylate, dimethoxysilyl propyl methacrylate, diethoxysilylpropyl methacrylate, dibutoxysilylpropyl methacrylate, diisopropoxysilylpropyl methacrylate, trimethoxysilylpropyl acrylate, triethoxysilylpropyl acrylate, tributoxysilylpropyl acrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilylpropyl acrylate, diethoxysilylpropyl acrylate, dibutoxysilylpropyl acrylate, diisopropoxysilylpropyl acrylate, maleic anhydride, N-phenylmaleimide, N-butylmaleimide, butadiene, isoprene, chloroprene, ethylene, vinyl acetate, 2-(2-oxo-1-imidazolidinyl)ethyl 2-methyl-2-propenoate, 1-[2-[[2-hydroxy-3-(2-propyl) propyl]]amino]ethyl]-2-imidazolidinone, N-vinyl pyrrolidone, N-vinyl imidazole, crotonic acid, vinyl sulfonic acid, and combinations thereof.

It is to be noted that the attachment of probes or other molecules to the water-soluble or water-dispersible segment of the polymer chain may be achieved by a number of ways including, for example: (i) post-polymerization activation and derivatization (wherein the probe molecules react with the functional moieties on the segments after polymerization, and after the moieties have been activated, as further described herein); (ii) post-polymerization derivatization (wherein the probe molecules react directly with active functional moieties, the moieties having been formed in their active state as part of the polymerization process); and, (iii) the monomers are modified so as to include the probe molecules prior to polymerization. Alternatively, however, it is to be further noted that these water-soluble or water-dispersible segments can be derived from hydrophobic polymers prepared from hydrophobic monomers, these polymers subsequently being made water-soluble or water-dispersible by means of, for example, alkylation, phosphorylation, carboxylation, amination, sulfonation, sulfatation, metallation and the like.

After the polymerization reaction, in preferred embodiments with living-type polymerizations, the polymer chain end that carries the control agent can be modified, with for example, a reduction step that yields a functional chain end or in a radical exchange step to introduce other functionalities. Probes may be attached to these modified chain ends.

Figure 5:
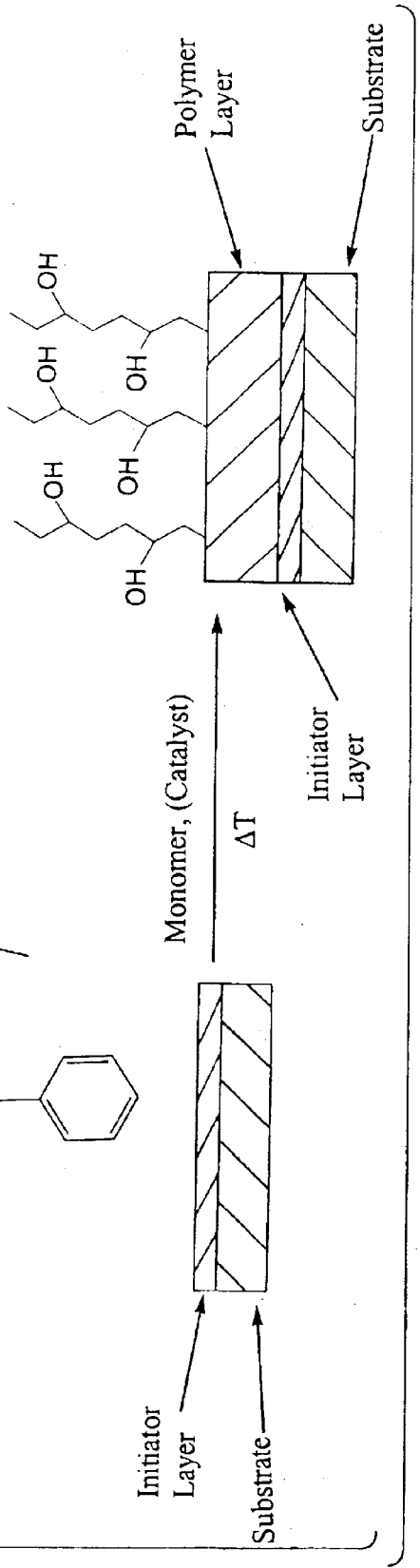

As shown in part of FIG. 5, the polymer-modified surface may be referred to as having a "polymer layer" on top of the surface. The depiction in FIG. 5 actually shows the substrate (e.g., a wafer), an initiator layer (e.g., bound initiator or initiator-control adduct), a "polymer layer" and then some polymer chains on top of the polymer layer. The polymer chains on top of the polymer layer are part of the polymer layer and are shown for illustration purposes to show what the polymer layer comprises in the embodiment shown in FIG. 5. Generally, the polymer-modified surface will have a determinable thickness. The thickness of the polymer layer, measured from the substrate surface, is selected based upon the particular application. In general, however, dry thickness of the polymer layer ranges from about 20 to about 2000 angstroms, while in some embodiments this thickness may range from about 30 to about 1500 angstroms, or from about 50 to about 1000 angstroms, all of which are useful for analyzing biological samples of various types.

It is to be noted that the thickness is measured as a dry thickness, in the absence of solvent, by ellipsometry as known to those of skill in the art. See, e.g., "A User's Guide to Ellipsometry", by Harland G. Tompkins (Academic Press (owned/published by Harcourt Brace Jovanovich), 1993), which is incorporated herein by reference. Also, depending on the chain molecular weight and grafting density, as well as the solvent, the polymer chains can also be measured when in the presence of a solvent. This "wet thickness" might be many times the dry thickness. The polymer chain conformation in solvent can also be measured by means known to those of skill in the art (as further described herein).

Probes

A wide variety of biological probes can be employed in connection with the present invention. In general, the probe molecule is preferably substantially selective for one or more biological molecules of interest. The degree of selectivity will vary depending on the particular application at hand, and can generally be selected and/or optimized by a person of skill in the art.

The probe molecules can be bonded to the functional group-bearing polymer segments using conventional coupling techniques (an example of which is further described herein below under the heading "Application"). The probes may be attached using covalently or non-covalently (e.g., physical binding such as electrostatic, hydrophobic, affinity binding, or hydrogen bonding, among others). For example, one technique is the in situ synthesis of probes onto the polymer. See, e.g., Sundberg et al., U.S. Pat. No. 5,919,523 which is incorporated herein by reference. Another technique is the covalent attachment of pre-formed probes (e.g., spotting of probes), which can be achieved as long as a functionality for covalent attachment (such as an amine, hydroxyl, thiol, etc.) is present. Spotting techniques are generally known (see, for example, U.S. Pat. Nos. 5,424, 186; 5,677,195; and, 5,744,305, which are incorporated herein by reference for all purposes). In an alternative embodiment, the probes can be bonded, preferably covalently bonded to the monomer units (before polymerization), and then incorporated into the substrate-bound polymer during the polymerization reaction.

Typical polymer brushes functionalities that are useful to covalently attach probes are chosen among hydroxyl, carboxyl, aldehyde, amino, isocyanate, isothiocyanate, azlactone, acetylacetonate, epoxy, oxirane, carbonate sulfonyl ester (such as mesityl or tolyl esters), acyl azide, activated esters (such as N(hydroxy)succinimide esters), O-acyliso-urea intermediates from COOH—carbodiimide adducts, fluoro-aryle, imidoester, anhydride, haloacetyl, alkyliodide, thiol, disulfide, maleimide, aziridine, acryloyl, diazo-alkane, diazo-acetyl, di-azonium, and the like. These may be provided by copolymerizing functional monomers such as 2-hydroethyl(meth)acrylate, hydroxyethyl(meth) acrylamide, hydroxyethyl-N(methyl) (meth)acrylamide, (meth)acrylic acid, 2-aminoethyl(meth)acrylate, amino-protected monomers such as maleimido derivatives of amino-functional monomers, 3-isopropenyl, αα-dimethylbenzylisocyanate, 2-isocyanato-ethylmethacrylate, 4,4-dimethyl-2-vinyl-2-oxazoline-5-one, acetylacetonate-ethylmethacrylate, and glycidylmethacrylate.

Post derivatization of polymer brushes proves also to be efficient. Typical methods include activation of —OH functionalized groups with, for example phosgene, thiophosgene, 4-methyl-phenyl sulfonylchoride, methylsulfonylchloride, and carbonyl diimidazole. Activation of carboxylic groups can be performed using carbodiimides, such as 1-ethyl-3-(3-dimethylamino-propyl) carbodiimide hydrochloride, or 1-cyclohexyl-3-(2-morpholinoethyl) carbodiimide, among others. Aldehyde groups can be synthesized from the periodate-mediated oxidation of vicinal —OH, obtained from hydrolysis of epoxy functional brushes. Alternatively, aldehyde groups are attached by reaction of bis-aldehydes (e.g., glutaraldehyde) onto amino-modified polymer brushes. Amino-functional brushes can also be prepared by reacting di-amino compound on aminoreactive brushes, such as N(hydroxy) succinimide esters of carboxylates brushes. (Other state-of-the-art coupling chemistries, such as described in *Bioconjuguate Techniques*, Greg. T. Hermanson, Academic Press, 1996, are also applicable and are incorporated herein by reference.)

One useful class of probes is nucleic acid-containing probes, such as nucleic acid polymers. As used herein, a "nucleic acid" of the nucleic-acid containing probe includes DNA, RNA, and derivatives thereof. For example, the nucleic acid can be DNA or RNA-based molecules containing bases other than adenine, cytosine, guanine, thymine, or uracil (e.g., bromothymine or azaguanine), sugars other than deoxyribose or ribose (e.g., arabinose, 2'-O-methylribose xylulose, or hoexose), or modified phosphate backbones. A modified phosphate backbone can include, for example, phosphorothioate, phosphorodithioate, phosphoramidothioate, phosphoramidate, phosphordiamidate, methylphosphonate, alkyl phosphotriester, and formacetal linkages, or analogs thereof. In addition, the nucleic acid-containing probe can be a peptide nucleic acid ("PNA"), or an uncharged or possibly positively charged nucleic acid derivative that contains a pseudopeptide backbone. Peptide nucleic acids can be produced using standard techniques as described, for example, in U.S. Pat. No. 5,539,082, which is hereby incorporated by reference.

Nucleic acid polymer probes are typically at least six nucleotides in length, and can range in size up to the length of an entire chromosome. Typically, nucleic acid probes are oligonucleotides that are 8 to 100 nucleotides in length (e.g., 15 to 30, 40, 50 nucleotides) or complementary DNA fragments ("cDNA") that are partial or complete (e.g., having 100 to 5,000 nucleotides).

Nucleic acid probes can be synthesized by standard methods known in the art such as, for example, by use of an automated nucleic acid synthesizer of the type commercially available from Biosearch and Applied Biosystems. Phosphorothioate oligonucleotides can be synthesized according to the method of Stein et al. (*Nucleic Acids Res.*, 1988, 16:3209–3221), which is hereby incorporated by reference. Methylphosphonate oligonucleotides can be prepared by use of controlled pore glass polymer supports, as described by Sarin et al. (*Proc. Natl. Acad. Sci. USA*, 1988, 85(20) :7448–7451).

Nucleic acid probes also can be isolated from genomic DNA, total cellular RNA, or messenger RNA ("mRNA") using standard methods known in the art. For example, the nucleic acid probes may be obtained from microdissected RNA, a clone set from a genome of interest (e.g., a set of expressed sequence tags ("ESTs") or a cDNA library), a restriction enzyme fragment, or a polymerase chain reaction ("PCR") product. PCR refers to a procedure or technique in which target nucleic acids are amplified. Generally, sequence information from the ends of the region of interest or beyond is employed to design oligonucleotide primers that are identical or similar in sequence to opposite strands of the template to be amplified. PCR can be used to amplify specific sequences from DNA as well as RNA (reverse-transcriptase PCR), including sequences from total genomic DNA or total cellular RNA. Primers are typically 14 to 40 nucleotides in length, but can range from 10 nucleotides to hundreds of nucleotides in length. These primers can be used to incorporate chemical "hooks" for attaching the probe to the activated polymer (e.g., by incorporating a terminal amine, thiol, or biotin moiety). PCR is described, for example, in PCR Primer: A Laboratory Manual, ed. by C. Dieffenbach and G. Dveksler, Cold Spring Harbor Laboratory Press, 1995.

Amino acid polymers, such as polypeptides, represent a second class of useful probes. As used herein, "amino acid polymers" or interchangeably, "polypeptide," refers to a chain of amino acids, regardless of length and regardless of functionality. Typically, the polypeptide is at least 5 amino acid residues in length and can range up to a full-length protein. Short polypeptides can be created using automated synthesis, nearly identical to the above description for DNA with Applied Biosystems instrumentation. Moreover, the polypeptide can have a known or suspected functionality or partial functionality (e.g., as a component of a functionally active moiety). Non-limiting examples of polypeptides include enzymes, receptors, and antibodies. As used herein, the term "antibody" includes polyclonal antibodies, monoclonal antibodies, humanized or chimeric antibodies, single chain antibodies, Fab fragments, and $F(ab)_2$ fragments. Polyclonal antibodies are heterogeneous populations of antibody molecules that are contained in the sera of immunized animals. Monoclonal antibodies, which are homogeneous populations of antibodies with affinity for a particular epitope of an antigen, can be prepared using standard methodology. In particular, monoclonal antibodies can be obtained by any technique that provides for the production of antibody molecules by continuous cell lines in culture such as described by Kohler et al. (Nature, 256:495 (1975)); the human B-cell hybridoma technique (Kosbor et al., Immunology Today, 4:72 (1983) and Cole et al., Proc. Natl. Acad. Sci. USA, 80:2026 (1983)); and the EBV-hybridoma technique (Cole et al., "Monoclonal Antibodies and Cancer Therapy," Alan R. Liss, Inc., pp. 77–96 (1983)). Such antibodies can be of any immunoglobulin class including IgG, IgM, IgE, IgA, IgD, and subclasses thereof. A hybridoma producing the monoclonal antibodies can be cultivated in vitro or in vivo. As those of skill in the art will understand, the immobilization of proteins has been linked to the loss of secondary structure, and thus the overall activity in non-aqueous environments; it is believed that the present invention provides a pathway to enable a sensor using protein probes that have sufficient activity of the immobilized proteins. Applications involving such polypeptide probes (e.g., antibodies) can be used, for example, as biosensors in diagnostic assays, as well as separation media for bioseparations (e.g. affinity chromatography).

A chimeric antibody is a molecule in which different portions are derived from different animal species, such as those having a variable region derived from a murine monoclonal antibody and a human immunoglobulin constant region. Chimeric antibodies can be produced through standard techniques.

Single chain antibodies are formed by linking the heavy and light chain fragments of the Fv region via an amino acid bridge, resulting in a single chain polypeptide. Single chain antibodies can be produced using standard techniques as described, for example, in U.S. Pat. No. 4,946,778.

Antibody fragments can be generated using known techniques. For example, such fragments include $F(ab')_2$ fragments that can be produced by pepsin digestion of the antibody molecule, and Fab fragments that can be generated by reducing the disulfide bridges of $F(ab')_2$ fragments. Alternatively, Fab expression libraries can be constructed as described, for example, in Huse et al., Science, 246:1275 (1989).

The probe can also be a cell. The cells can be naturally occurring or modified cells. In some embodiments, the cells can be genetically modified to express surface proteins (e.g., surface antigens) having known epitopes or having an affinity for a particular biological molecule of interest. Examples of useful cells include blood cells, liver cells, somatic cells, neurons, and stem cells. Other biological polymers can include carbohydrates, cholesterol, lipids, etc.

While biological molecules can be useful as probes in many applications, the probe itself can be a non-biological molecule. In one case, the dye probe can be used for selective biomolecule recognition, as generally described herein. Non-biological probes can also include small organic molecules that mimic the structure of biological ligands, drug candidates, catalysts, metal ions, lipid molecules, etc. Also, dyes, markers or other indicating agents can be employed as probes in the present invention in order to enable an alternative detection pathway. A combination of dyes can also be used. Dyes can also be used, in another case, as a substrate "tag" to encode a particular substrate or a particular region on a substrate, for post-processing identification of the substrate (polymer probe or target).

The sensors can also be utilized in a multi-step or "sandwich" assay format, wherein a number of biomolecule targets can be applied or analyzed in sequential fashion. This approach may be useful to immobilize a protein probe for the desired biomolecule target. It may also be applied as a form of signal enhancement if the secondary, tertiary, etc. biomolecules serve to increase the number of signal reporter molecules (i.e., fluorophores). For example, an attached probe may bind a protein target A through affinity binding or covalent attachment. Some portion of protein A then acts as a probe to immobilize protein target B through affinity binding or covalent attachment. Some portion of protein B then acts as a probe to immobilize protein target C through affinity binding, and so on. A similar assay may be performed using duplex and triplex DNA, RNA, PNA and/or some combination thereof.

The sensors can be used to analyze biological samples such as blood, plasma, urine, saliva, tears, mucuous derivatives, semen, stool samples, tissue samples, tissue swabs and combinations thereof. For example, where the probes are nucleic acids, the resulting sensor can be used to monitor expression levels of genes or to identify mutations or polymorphisms, or to detect the genetic material related to a disease state. In either case, target nucleic acids (i.e., free nucleic acid molecules) typically are labeled and hybridized to the tethered nucleic acid probes. For example, the target nucleic acid molecules can be fluorescently labeled and hybridized with the tethered probes under suitable conditions. Fluorescence from target nucleic acids that hybridize at discrete locations on the sensor surface can be detected by a fluorescence reader (e.g., such as a laser scanning device, a CCD camera, a confocal scanning device or plate reader, etc.). Hybridization of target nucleic acids that are labeled with a radioisotope can be detected by phosphor-imaging. Alternative methods of detection include electronic signal detection in which positive hybridization events are detected by electron transfer reactions (e.g., as described in U.S. Pat. No. 5,824,473), by the use of mass spectrometry (e.g., as described in U.S. Pat. No. 5,872,003), by electrical charge, or by magnetic detection techniques, among others.

Hybridization conditions can be tailored for particular applications. For example, hybridization conditions may differ based on length or base composition of the probes and target nucleic acids. Standard blocking agents such as Denhardt's reagent and sheared salmon sperm DNA can be used to minimize background hybridization as described, for example, in Southern et al., *Nature Genet.*, supplement, 1999, 21:5–9 and Cheung et al., *Nature Genet.*, supplement, 1999, 21:15–19.

Sensors in which the tethered probes are polypeptides can be used, for example, to screen or characterize populations of antibodies having specific binding affinity for a particular target antigen or to determine if a ligand had affinity for a particular receptor, according to procedures described generally in Leuking et al., *Anal. Biochem.*, 1991, 270(1):103–111. Target polypeptides can be labeled, e.g., fluorescently or with an enzyme such as alkaline phosphatase, or radio labeling for easy detection.

Analyses/Measurements

Density Calculation

The present invention enables the "tailoring" of the surface of a polymer brush in order to achieved a desired number of accessible functional groups on its surface. As previously noted, one factor which must be controlled as part of the tailoring process is the grafting density of the water-soluble (or water-dispersible) segments on the substrate surface. One method for determine segment grafting density is by calculation based on the molecular weight of the polymer chains grown in solution ($M_{gpc}$) during the polymerization process (as a result of initiator being present both on the substrate surface and in the polymerization solution or system), and the polymer layer thickness, as determined by ellipsometry (t) measurements of the polymer layer on the modified substrate surface. This calculation is achieved using the following formula:

$$\text{Grafting Density} = (1 * 10^{4} * t * \rho / M_{gpc})$$

wherein grafting density is expressed in picomoles/cm², t is expressed in Angstroms, $\rho$ is specific gravity and is expressed in grams/cm³ and molecular weight ($M_{gpc}$) is expressed in g/mole. This formula is used in Experiments 1–8, below, in order to calculate segment grafting density.

In those instances wherein no free initiator is used in the polymerization process, no polymer forms in solution. As a result, polymer brushes molecular weights cannot be measured directly. Therefore, in order to calculate the molecular weight, the polymer thickness (t) is measured from a substrate with a known density of polymer chain initiating sites (which directly correlates to the grafting density). Based on this information, the molecular weight ($M_{gpc}$, g/mole) can then be calculated using the above formula (i.e., $M_{gpc}$, =1*10⁴*t* $\rho$/grafting density).

Cleavable Dye Test

This method may be used to quantify the number of functional groups generally accessible to a probe or target biomolecule which are about the same size as the dye molecule being used, to optimize small molecule modification (i.e., activation), and to quantify covalently attached oligonucleotides/probes (e.g., DNA). Generally speaking, the functional groups on the polymer chain segments are quantified by attaching a dye molecule of a given size to each of the functional sites which are accessible to molecules of that size, washing the substrate to remove excess/unbound dye, cleaving the bound dye molecules, collecting the cleaved dye molecules, and then measuring the amount of dye collected for a given surface area, using HPLC analysis with a fluorescence detector.

The amount or concentration of dye in the solution is calculated from the fluorescence signal using a calibration curve obtained from a model reaction. From this concentration data, the number of dye molecules can be determined, which then can be directly correlated to the number of functional groups on the water-soluble (or water-dispersible) segments that were accessible to molecules of a size about equal to, or less than, the size of the dye molecules employed in the test. If the surface area of the brush is known, a number of accessible functional groups per unit area may then be calculated. This test method can also be used in a similar manner to quantify the number of accessible functional groups for the probe or other molecule directly, by attaching a dye molecule to the probe that is to be attached.

Stability Test

The present invention enables the preparation of substrates (both planar and non-planar surfaces) having water-soluble (or water-dispersible) segments attached thereto, and optionally probes attached to these segments, which are highly stable. More specifically, the present invention enables the attachment of these segments to the substrate surface, and likewise the attachment of probes to the segments, in a manner which prevents their detachment upon exposure to subsequent processing steps. For example, experience to-date has shown that biosensors prepared in accordance with the present process may be heated to a temperature above about 40° C., preferably ranging from about 40 to about 60° C., in an aqueous solution for about 16 hours (conditions commonly employed in gene expression tests) with less than about a 20% loss of probes from the segments, or segments from the substrate surface. In fact, in some cases loss may be less than about 15%, less than about 10%, or even less than about 5%. In contrast, existing sensors, such as those comprised of a glass substrate to which is attached a DNA probe by means of a silane linker, commonly experience a loss of up to about 90% of the linkers which connect the probe to the substrate surface (and therefore the probes themselves), rendering the sensor significantly less sensitive.

Film Thickness Measurements

Polymer layer or film thickness may be measured as a dry thickness (i.e., in the absence of solvent) by, among other methods known to those of skill in the art, ellipsometry. (See, e.g., "A User's Guide to Ellipsometry", by Harland G. Tompkins (Academic Press, owned/published by Harcourt Brace Jovanovich, 1993), which is incorporated herein by reference.) Briefly, the thickness is determined by reflecting polarized light from the film surface and analyzing the change in the polarization state which results from the reflection. This can be related to the film thickness and index of refraction by comparing the results of the measurement with the results of a model calculation, which incorporates thickness and index as variable parameters.

Also, depending on the chain molecular weight and grafting density, as well as the solvent, the polymer chains can also be measured when in the presence of a solvent (i.e., in the "swollen" state). This "wet thickness" might be many times the dry thickness depending on the segment molecular weight, the segment persistence length, and the segment grafting density. The polymer chain conformation in solvent might be measured with neutron reflectivity or with contact methods such as by Atomic Force Microscopy ("AFM"—which provides a measure of compliance, which is similar to elasticity of the polymer on the surface; film thickness may also be measured, providing you can determine a baseline or edge within the scan), or by Surface Force Apparatus.

Applications

Once the functional group-bearing polymer chains have been grown on the substrate surface, it may be necessary to "activate" the functional groups prior to probe coupling. Various activation and coupling techniques are known in the art. These techniques may vary depending upon the particular application. Accordingly, while the following procedures are intended for illustrative purposes, those of skill in the art would be able to use these procedures, or procedures similar thereto, in order to achieve the desired results.

Carbonyidiimidazole(CDl) Activation of Hydroxyl-functionalized Polymers on Glass Slides Glassware used in the procedure are all oven dried at 150° C. and placed inside a dry glove box while warm. All measurements and weighings are done inside the dry box, as well. Glass slides used as substrates are dried in vacuum oven at 40° C. (24 in Hg) overnight.

In a glove box, a hydroxyl-functionalized polymer brush, bound on a glass slide, is placed in a 20 ml glass vial, which is then filled with a 0.5 M stock solution of carbonyldiimidazole in anhydrous acetonitrile. The vial is sealed tight and wrapped with electric tape (to ensure the seal). The vial is removed from the dry box and placed on horizontal shaker for 24 hrs. The vial is opened at the end of the 24 hr period in ambient air, and then the glass slide is washed with anhydrous Acetonitrile several times. After air drying, the slide is stored in a dry, dark place until needed.

Coupling of Amine-functionalized Oligonucleotide Probes onto CDI-activated Polymer Brush Printing and coupling of oligonucleotide probes onto the CDI-activated polymer brushes is achieved as follows: to begin, three different stock solutions (100, 50 and 25 $\mu$M) of a 50 mer oligonucleotide (amine functionality in 3' position and Cy3 dye in 5' position), were prepared with a total concentration of 150 mM sodium phosphate (pH=8.5). The oligonucleotides were then spotted onto the glass slide using a 1 $\mu$L pipette in varying amounts on different regions of the substrates in a array format, for purposes of comparison.

After spotting was complete, the slides were incubated in a glass chamber at room temperature for 18 hrs. A blocking solution containing 50 mM ethanolamine, 0.1 M Tris and 0.1 weight percent SDS (pH=9) was then prepared. The modified slides were washed with the blocking solution at room temperature for 1 hr. and subsequently rinsed with water and air dried.

Activation of Carboxylate-functionalized Polymers and Coupling of Amine-functionalized Oligonucleotide Probes A carboxylate-functionalized (COOH) polymer can be activated, and amine-functionalized probes can be coupled, via the commonly-known technique of carbodiimide activation. For example, using EDC [1-ethyl-3-(3-dimethylaminopropylcarbodiimide], an amine-functionalized probe can be coupled to the activated polymer by a single-step condensation via the amine-reactive intermediate, O-acylisourea. This intermediate is unstable in aqueous solution and must be immediately reacted with the amine-functionalized probe. (see, e.g., Williams & Ibrahim, JACS, 103, 1981, p. 7090–7095.)

Alternatively, the amine-terminated probe can be coupled in two steps by using EDC and NHS [N-hydroxysuccinimide]. In this method, the polymer functional sites retain a stable, amine-reactive NHS ester functionality in the presence of water, which can later be coupled with the amine-functionalized probe. (see, e.g., Grabaraek & Gergely, Anal. Biochem., 185, 1990, p. 131–135.)

General Technique for Hybridization and Scanning Oligonucleotide (and cDNA) Arrays Once the polymer brush has been successfully activated and the probes attached, the resulting "biosensor" may be used in scanning procedures common in the art (see, e.g., Lockhart et al., Nature Biotechnology (14), 1996, pp. 1675-). A scanning procedure such as the following may also be used.

The above-referenced probe-activated brushes were immerse in either (i) a 4×SSC target solution (i.e., a solution comprising 30 mM sodium chloride, 3 mM sodium citrate and 0.1% SDS; pH 8.0), or (ii) a 6×SSPE target solution (i.e., a solution comprising 0.9 M sodium chloride, 60 mM $NaH_2PO_4$, 6 mM EDTA and 0.005% Triton X-100; pH 7.6), both of which additionally contained RNA or DNA target molecules. In one embodiment, the hybridization can be performed by exposing the whole slide to the target solution, in this case by immersing or otherwise placing about 24 to 100 L of the target solution on the array under a 22 mm×22 mm glass cover slip (used in order to limit the amount of solution which evaporates during the process). Hybridization may also be achieved by exposing the array to a much larger amount of the target solution (e.g., about 500 microliters to about 500 milliliters of solution, but this typically requires some form of flow cell, and/or agitation of the bulk solution).

Hybridization was then achieved by heating each of the probe-attached brushes at about 40 to about 65° C. for a period of time (ranging from about 4 to about 24 hrs, depending on target molecule being studied). If a biotinylated target molecule is used, the hybridized brush is additionally incubated with 2 g/ml fluorescenated streptavidin or streptavidin-phycoerythrin (SAPE) in the hybridization buffer at about 40° C. for 5–10 min.

To scan the resulting hybridized brushes in solution, they are first rinsed or gently agitated with fresh hybridization buffer for about 5–10 minutes, and then they are scanned for surface fluorescence using a confocal microarray scanner (such as, for example, a Hewlett Packard GeneArray scanner).

To scan the resulting hybridized brushes dry, they are first rinsed or agitated in a solution comprising a 1×SSC solution (i.e., the above-referenced 4×SSC solution being dilutioned by a factor of 4), the cover slip being removed if necessary, after which the brushes are removed and blotted dry. The rinse step is repeated twice, each time using a more dilute solution (i.e., the above 1×SSC solution first being diluted by a factor of 5, and then a factor of 20). The brushes are then spun dry by centrifugation in a slide rack (Beckman GS-6 tabletop centrifuge at 600 RPM for 2 mins.), after which the brushes are scanned for surface fluorescence using a microarray scanner (such as, for example, an AXON GenePix or GSI Lumonics ScanArray scanner).

Advantageously, the brushes may be used to accurately call in excess of 90%, 95%, 97%, 98%, or 99% of the targets in an analyte-containing solution.

Definitions

As used herein, the phrase "characterized by the formula" is not intended to be limiting and is used in the same way that "comprising" is commonly used. The term "independently selected" is used herein to indicate that the R groups, e.g., $R^1$, $R^2$ and $R^3$ can be identical or different (e.g. $R^1$, $R^2$ and $R^3$ may all be substituted alkyls or $R^1$ and $R^2$ may be a substituted alkyl and $R^3$ may be an aryl, etc.). A named R group will generally have the structure that is recognized in the art as corresponding to R groups having that name. For the purposes of illustration, representative R groups as enumerated above are defined herein. These definitions are intended to supplement and illustrate, not preclude, the definitions known to those of skill in the art.

The term "alkyl" is used herein to refer to a branched or unbranched, saturated acyclic hydrocarbon radical. Suitable alkyl radicals include, for example, methyl, ethyl, n-propyl, i-propyl, n-butyl, t-butyl, i-butyl (or 2-methylpropyl), etc. In particular embodiments, alkyls have between 1 and 200 carbon atoms, between 1 and 50 carbon atoms, or between 1 and 20 carbon atoms.

The term alkenyl is used herein to refer to a branched or unbranched acyclic hydrocarbon radical having at least one carbon-carbon double bond. Exemplary alkenyl radicals include, for example, 2-propenyl (or allyl), vinyl, etc. In particular embodiments, alkenyls have between 1 and 200 carbon atoms, between about 1 and 50 carbon atoms, or between about 1 and 20 carbon atoms. In addition, this term embraces radicals having both "cis" and "trans" orientations, or alternatively, "E" and "Z" orientations.

The term akynyl is used herein to refer to a branched or unbranched acyclic hydrocarbon radical having at least one carbon-carbon triple bond. In particular embodiments, alkynyls have between 1 and 200 carbon atoms, between about 1 and 50 carbon atoms, or between about 1 and 20 carbon atoms.

"Substituted alkyl," "substituted alkenyl" and "substituted alkynyl" refer to the alkyl, alkenyl and alkynyl radicals, respectively, as just described in which one or more hydrogen atoms to any carbon of these radicals is replaced by another group such as a heteroatom, halogen, aryl, substituted aryl, cycloalkyl, cycloalkenyl, substituted cycloalkyl, substituted cycloalkenyl and combinations thereof. Exemplary substituted alkyls include, for example, benzyl, trifluoromethyl and the like.

The term "heteroalkyl," "heteroalkenyl" and "heteroalkynyl" refer to the alkyl, alkenyl and alkynyl radicals, respectively, described above in which one or more of the carbon chain atoms of these radicals is replaced by a heteroatom selected from the group consisting of N, O, P, B, S, Si, Se and Ge. The bond between the carbon atom and the heteroatom may be saturated or unsaturated. Thus, an alkyl substituted with a heterocycloalkyl, substituted heterocycloalkyl, heteroaryl, substituted heteroaryl, alkoxy, aryloxy, boryl, phosphino, amino, silyl, thio, or seleno is within the scope of the term heteroalkyl. Suitable heteroalkyls include cyano, benzoyl, 2-pyridyl, 2-furyl, $Me_3SiOCH_2(CH_3)_2C-$ and the like.

The term "cycloalkyl" is used herein to refer to a saturated cyclic non-aromatic hydrocarbon radical having a single ring or multiple condensed rings. Exemplary cycloalkyl radicals include, for example, cyclopentyl, cyclohexyl, cyclooctanyl, bicyclooctyl, etc. In particular embodiments, cycloalkyls have between 3 and 200 carbon atoms, between 3 and 50 carbon atoms or between 3 and 20 carbon atoms.

The term "cycloalkenyl" is used herein to refer to a partially unsaturated (i.e., having at least one carbon-carbon double bond), cyclic non-aromatic hydrocarbon radical having a single ring or multiple condensed rings. Exemplary cycloalkenyl radicals include, for example, cyclopentenyl, cyclohexenyl, cyclooctenyl, etc. In particular embodiments, cycloalkyls have between 3 and 200 carbon atoms, between 3 and 50 carbon atoms or between 3 and 20 carbon atoms.

"Substituted cycloalkyl" and "substituted cycloalkenyl" refer to cycloalkyl and cycloalkenyl radicals, respectively, as just described wherein one or more hydrogen atoms to any carbon of these radicals is replaced by another group such as a halogen, alkyl, alkenyl, alkynyl, substituted alkyl, substituted alkenyl, substituted alkynyl, aryl, substituted aryl, cycloalkyl, cycloalkenyl, substituted cycloalkyl, substituted cycloalkenyl, heterocyclo, substituted heterocyclo, heteroaryl, substituted heteroaryl, alkoxy, aryloxy, boryl, phosphino, amino, silyl, thio, seleno and combinations thereof. Exemplary substituted cycloalkyl and cycloalkenyl radicals include, for example, 4-dimethylaminocyclohexyl, 4,5-dibromocyclohept-4-enyl, and the like.

The term "aryl" is used herein to refer to an aromatic substituent that may be a single aromatic ring or multiple aromatic rings which are fused together, linked covalently, or linked to a common group such as a methylene or ethylene moiety. The common linking group may also be a carbonyl as in benzophenone or oxygen as in diphenylether or nitrogen in diphenylamine. The aromatic ring(s) may include phenyl, naphthyl, biphenyl, diphenylether, diphenylamine and benzophenone among others. In particular embodiments, aryls have between 1 and 200 carbon atoms, between 1 and 50 carbon atoms or between 1 and 20 carbon atoms.

"Substituted aryl" refers to aryl as just described in which one or more hydrogen atom to any carbon is replaced by one or more functional groups such as alkyl, alkenyl, alkynyl, substituted alkyl, substituted alkenyl, substituted alkynyl, cycloalkyl, cycloalkenyl, substituted cycloalkyl, substituted cylcoalkenyl, heterocyclo, substituted heterocyclo, halogen, alkylhalos (e.g., $CF_3$), hydroxy, amino, phosphino, alkoxy, thio and both saturated and unsaturated cyclic hydrocarbons which are fused to the aromatic ring(s), linked covalently or linked to a common group such as a methylene or ethylene moiety. The linking group may also be a carbonyl such as in cyclohexyl phenyl ketone. Specific examples of substituted aryls include perfluorophenyl, chlorophenyl, 3,5-dimethylphenyl, 2,6-diisopropylphenyl and the like.

The term "heterocyclo" is used herein to refer to saturated, partially unsaturated and unsaturated cyclic radicals (including, for example, cycloalkyl and cycloalkenyl radicals as described), wherein one or more or all carbon atoms of the radical are replaced by a heteroatom such as nitrogen, phosphorus, oxygen, sulfur, silicon, germanium, selenium, or boron. Additionally, the term "heteroaryl" as used herein refers to a specific example of a class of unsaturated cyclic radicals wherein one or more carbon atoms of an aromatic ring or rings are replaced by a heteroatom(s) such as nitrogen, oxygen, boron, selenium, phosporus, silicon or sulfur. Heteroaryl refers to structures that may be a single aromatic ring, multiple aromatic ring(s), or one or more aromatic rings coupled to one or more nonaromatic ring(s). In structures having multiple rings, the rings can be fused together, linked covalently, or linked to a common group such as a methylene or ethylene moiety. The common linking group may also be a carbonyl as in phenyl pyridyl ketone. As used herein, rings such as thiophene, pyridine, isoxazole, phthalimide, pyrazole, indole, furan, etc. or benzo-fused analogues of these rings are defined by the term "heteroaryl." Other exemplary heterocyclo radicals include, for example, piperazinyl, morpholinyl, tetrahydropyranyl, tetrahydrofuranyl, piperidinyl, pyrrolidinyl, oxazolinyl, and the like.

"Substituted heterocyclo" and "substituted heteroaryl" refer to heterocyclo and/or heteroaryl radicals as just described wherein one or more hydrogen atom to any atom of the radical is replaced by another group such as a halogen, alkyl, substituted alkyl, aryl, substituted aryl, heteroaryl, substituted heteroaryl, alkoxy, aryloxy, boryl, phosphino, amino, silyl, thio, seleno and combinations thereof. Exemplary substituted heteroaryl radicals include, for example, 4-N,N-dimethylaminopyridine. Other exemplary substituted heterocyclo radicals include, for example, N-methylpiperazinyl, 3-dimethylaminomorpholine, and the like.

"Hydrocarbyl" refers to univalent hydrocarbyl radicals containing 1 to about 30 carbon atoms, preferably 1 to about 24 carbon atoms, most preferably 1 to about 12 carbon atoms, including branched or unbranched, saturated or unsaturated species, such as alkyl groups, alkenyl groups, aryl groups, and the like. The term "lower hydrocarbyl" intends a hydrocarbyl group of one to six carbon atoms, preferably one to four carbon atoms. The term "hydrocarbylene" intends a divalent hydrocarbyl moiety containing 1 to about 30 carbon atoms, preferably 1 to about 24 carbon atoms, most preferably 1 to about 12 carbon atoms, including branched or unbranched, saturated or unsaturated species, or the like. The term "lower hydrocarbylene" intends a hydrocarbylene group of one to six carbon atoms, preferably one to four carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and "heterohydrocarbylene" refer to hydrocarbylene in which at least one carbon atom is replaced with a heteroatom.

The term "alkoxy" is used herein to refer to the —OZ$^1$ radical, where Z$^1$ is selected from the group consisting of alkyl, substituted alkyl, cycloalkyl, substituted cycloalkyl, heterocylcoalkyl, substituted heterocycloalkyl, silyl groups and combinations thereof as described herein. Suitable alkoxy radicals include, for example, methoxy, ethoxy, benzyloxy, t-butoxy, etc. A related term is "aryloxy" where Z$^1$ is selected from the group consisting of aryl, substituted aryl, heteroaryl, substituted heteroaryl, and combinations thereof. Examples of suitable aryloxy radicals include phenoxy, substituted phenoxy, 2-pyridinoxy, 8-quinalinoxy and the like.

As used herein the term "silyl" refers to the —SiZ$^1$Z$^2$Z$^3$ radical, where each of Z$^1$, Z$^2$, and Z$^3$ is independently selected from the group consisting of alkyl, substituted alkyl, cycloalkyl, heterocycloalkyl, heterocyclic, aryl, substituted aryl, heteroaryl, substituted heteroaryl, alkoxy, aryloxy, amino, silyl and combinations thereof.

As used herein the term "boryl" refers to the —BZ$^1$Z$^2$ group, where each of Z$^1$ and Z$^2$ is independently selected from the group consisting of alkyl, substituted alkyl, cycloalkyl, heterocycloalkyl, heterocyclic, aryl, substituted aryl, heteroaryl, substituted heteroaryl, alkoxy, aryloxy, amino, silyl and combinations thereof.

As used herein, the term "phosphino" refers to the group —PZ"$_n$, where each of Z" is independently selected from the group consisting of hydrogen, oxygen, substituted or unsubstituted alkyl, cycloalkyl, heterocycloalkyl, heterocyclic, aryl, heteroaryl, silyl, alkoxy, aryloxy, amino and combinations thereof, where n is z to 4 depending on the phosphorus oxidation state.

The term "amino" is used herein to refer to the group —NZ$^1$Z$^2$, where each of Z$^1$ and Z$^2$ is independently selected from the group consisting of hydrogen, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "thio" is used herein to refer to the group —SZ$^1$, where Z$^1$ is selected from the group consisting of hydrogen, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "seleno" is used herein to refer to the group —SeZ$^1$, where Z$^1$ is selected from the group consisting of hydrogen, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "saturated" refers to lack of double and triple bonds between atoms of a radical group such as ethyl, cyclohexyl, pyrrolidinyl, and the like.

The term "unsaturated" refers to the presence one or more double or triple bonds between atoms of a radical group such as vinyl, acetylenyl, oxazolinyl, cyclohexenyl, acetyl and the like.

The phrase "living-type kinetics" refers to a polymerization where substantially all chains are reactive and propagating throughout the course of the polymerization reaction, and where a plot of chain length versus conversion is approximately linear.

The phrase "water-soluble" when used in connection with a polymer chain or a polymer chain segment which is soluble in an aqueous solution under some conditions (including, for example, aqueous solutions at a selected pH or in the presence of one or more selected buffers, etc.). Additionally, the phrase "water-dispersible" refers to a polymer chain which includes some entity which is not solvated by water.

The term "radius of gyration" or "Rg" refers to one-half the mean square end-to-end distance of a linear chain molecule in solution.

The sensors of this invention provide increased sensitivity of measurements as well as lower signal to noise ratios, as compared to known surface bound sensors. The invention will now be described further by way of the following examples.

EXAMPLES

Example 1

The following example illustrates one approach for the preparation of a monomer suitable for use in the present invention for polymer brush preparation.

I. Synthesis of N-Methyl,N-(2-hydroxyethyl)acrylamide

A. Synthesis of N-Methyl,N-2-(1-Trimethylsiloxy) ethylacrylamide

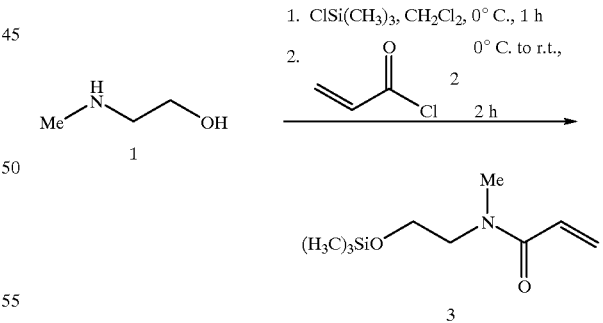

An ovendried 4 L three-necked flask equipped with an overhead mechanical stirrer, a 250 mL dropping funnel and an adapter to an argon line was charged under an atmosphere of argon with 113 g (1.5 mol, 121 mL) 2-(methylamino) ethanol (1), commercially available from Sigma-Aldrich, 1500 mL of anhydrous dichloromethane, and 334 g (460 mL, 3.3 mol) of triethylamine. The solution was chilled to ca. 0° C. (icebath) and 171 g (1.58 mol, 200 mL) of chlorotrimethylsilane (TMSCl) were added dropwise. Upon completion of the exothermic reaction (ca. 1 h), the reaction mixture is cooled again to ca. 0° C. (icebath) and acryloyl chloride (2) (136 g, 1.5 mol, 122 mL) were added dropwise and the reaction mixture was stirred for ca. 2 h with warming to room temperature. The pH of the reaction mixture should be established at ca. 9. The reaction was quenched by careful addition of 2 L of water. After thoroughly mixing, the aqueous layer was decanted off and the procedure was repeated twice (2×1000 mL). After thoroughly mixing, the aqueous layer was separated and the solution was dried ($Na_2SO_4$) and the solvent removed under reduced pressure to yield an orange-yellow product 3 of sufficient purity (>95% by $^1H$ NMR) which can be used without further purification in the next step. In the case of triethylammonium chloride impurities the washing protocol is repeated and the crude product was freed from excess triethylamine in high vacuo.

$^1H$ NMR (300 MHz, $CDCl_3$, room temp., (E)/(Z)-isomers): 6.53 (dd, J=16.8, 2.4 Hz, 1H, CH=CHH), 6.48 (dd, J=16.5, 2.4 Hz, 1H, CH=CHH), 6.26–6.13 (2 dd, superimposed, 2×1H, CH=CHH), 5.62–5.46 (2×dd, superimposed, 2×1H, CH=CHH), 3.60 (t, J=6.3 Hz, 2H, $CH_2CH_2O$), 3.55 (t, J=6.3 Hz, 2H, $CH_2CH_2O$), 3.40 (t, J=6.3 Hz, 2H, $CH_2CH_2O$), 3.35 (t, J=6.3 Hz, 2H, $CH_2CH_2O$), 3.03 (s, 3H, $NCH_3$), 2.91 (s, 3H, $NCH_3$), −0.01 (2s, superimposed, 2×9H, $Si(CH_3)_3$), both diastereoisomers) ppm.

B. Synthesis of N-Methyl,N-2-(1-hydroxy)ethylacrylamide:

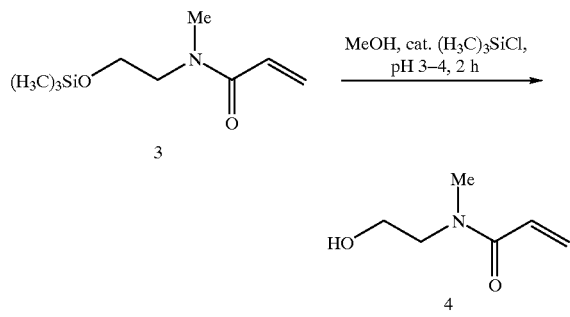

An ovendried 3 L round-bottomed flask equipped with a magnetic stir and an adapter to an argon line was charged under an atmosphere of argon with the crude product 3 obtained in step B and dissolved in 1.5 L of anhydrous methanol. Chlorotrimethylsilane was added dropwise the reaction mixture till the pH reached 3–4 (ca. 10 mL). The reaction mixture turns from orange to yellowish upon cleavage. Upon completion of the reaction, the solvent was removed under reduced pressure to yield 169 g (87%) of 4 as an orange crude product of sufficient purity which can be used without further purification in the following polymerization step.

$R_f$: 0.25 (EtOAc/MeOH=40:1). $^1H$ NMR (300 MHz, DMSO-$d^6$, room temp., (E)/(Z)-isomers): 6.76 (dd, J=16.5, 10.2 Hz, 1H, C(=O)CH=CHH), 6.73 (dd, J=16.5, 10.8 Hz, 1H, C(=O)CH=CHH), 6.08 (dd, J=16.8, 2.7 Hz, 1H, C(=O)CH=CHH), 6.06 (dd, J=16.5, 2.4 Hz, 1H, C(=O)CH=CHH), 5.65 (dd, J=10.5, 2.7 Hz, 1H, C(=O)CH=CHH), 5.60 (dd, J=10.5, 2.4 Hz, 1H, C(=O)CH=CHH), 4.80 (t, J=5.1 Hz, 1H, OH), 4.67 (t, J=5.4 Hz, 1H, OH), 3.53–3.45 (m, 2H, $CH_2CH_2OH$, both diastereoisomers), 3.45–3.37 (m, 2×2H, $CH_2CH_2OH$, both diastereoisomers), 3.06 (s, 3H, $NCH_3$), 2.88 (s, 3H, $NCH_3$) ppm.

C. N-Dansylcystamine (10):

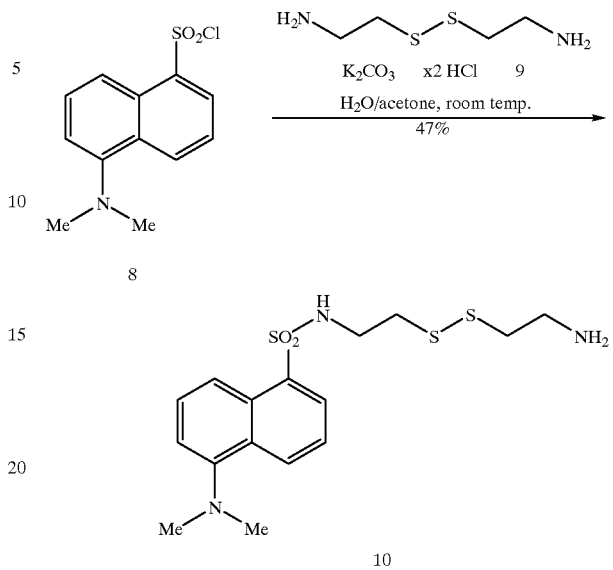

A 250 mL round-bottomed flask equipped with a magnetic bar and a 100 mL addition funnel was charged with cystamine dihydrochloride (9) (4.95 g, 22 mmol), $K_2CO_3$ (7.28 g, 52.8 mmol) and 50 mL of deionized water. Dansyl chloride (8) (1.00 g, 3.7 mmol) was dissolved in 20 mL of acetone and was added dropwise to the aqueous solution by means of the addition funnel. The reaction mixture turned from slight orange to yellow-green in two hours. Upon completion of the reaction, acetone was removed under reduced pressure. The reaction mixture was extracted with ethyl acetate (2×100 mL). The organic extracts were combined and washed with brine and dried over $MgSO_4$. After filtration and evaporation, the crude product was further purified by MPLC (silica gel, EtOAc/MeOH=2:1) to yield 670 mg (47%) of a yellow-green solid.

$R_f$: 0.48 (EtOAc/MeOH=1:1, stained with 2% ninhydrin). $^1H$ NMR (300 MHz, $CDCl_3$, room temp.): δ 8.51 (d, J=8.7 Hz, 1H, Ar—H), 8.25 (dd, J=8.7 Hz, 2H, Ar—H), 7.57–7.47 (m, 2H, Ar—H), 7.16 (d, J=7.5 Hz, 1H, Ar—H), 3.22 (t, J=6.3 Hz, 2H, $CH_2CH_2NHSO_2$), 2.86 (s, 8H, $NCH_3$, $CH_2CH_2NH_2$), 2.62 (t, J=6.3 $CH_2SSC H_2$), 2.57 (t, J=6.3 Hz, $CH_2SSC H_2$) ppm.

General Procedures: Examples 2–14 Using "Free" Initiator/initiator-Control Adduct Surface modifications were carried out on 2×3 and 1×3 inch fused silica glass wafers and 1 inch round silicon wafers. The wafers were cleaned with acetone and dichloromethane prior to use. The initiator-control agent adducts were tethered to the wafer surface via a short alkyl spacer (five carbon atoms) using silane chemistry following the procedure described in Husseman et al., Macromolecules 1999, 32, 1424–31. The corresponding chloromethyl adduct was treated with 1-pentenol using sodium hydride in dimethylformamide (DMF). Subsequent hydrosilylation with trichlorosilane/chloroplatinic acid in 1:1 ethanol/dimethoxyethane yielded the surface-active initiator-control agent adduct.

Treatment of this initiating moiety with the surface silanol groups of the fused silica and/or silicon wafers was catalyzed by triethylamine in toluene to provide covalently modified initiating substrate surfaces (i.e., derivatized surfaces). In each of the below examples (i.e., examples 1–8), the total amount of trichlorosilyl-substituted initatorcontrol agent adduct (and dummy molecules where applicable) was $5\times10^{-4}$ mol per 2×3 inch wafer. Depending on the desired chain surface grafting density on the surface, the ratio of linker-modified initiator-control agent adduct to dummy molecule was adjusted. The surface bound initiator-control agent adduct was either

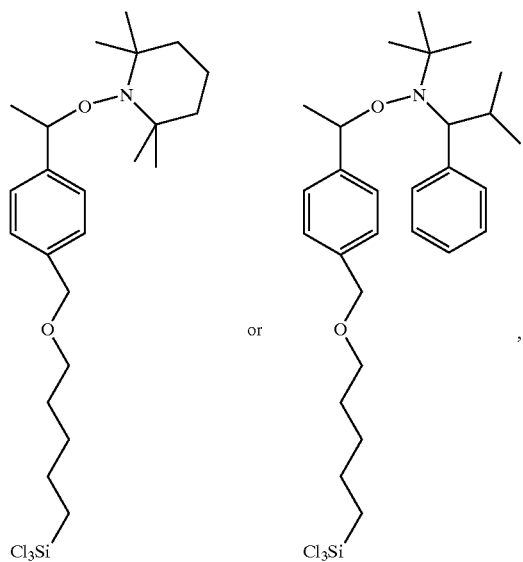

with the Si attached to the surface, as is known. The unbound initiator-control agent in all the examples was

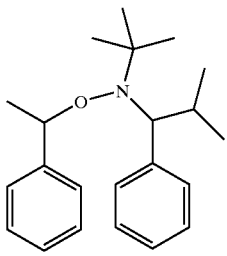

Also in each example, free radical nitroxyl was added, which had the composition

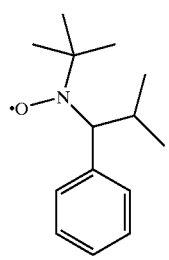

The inactive "dummy" molecule was

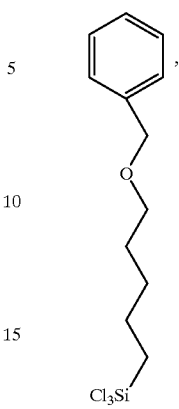

which was synthesized following the same procedure, but starting from benzylchloride.

The surface grafted initiator-control agent adducts were used to form surface-bound polymers as follows. All polymerizations were carried out in a 500 mL sealable vessel with an argon inlet. The total volume of the polymerization reaction mixture was 350 mL. This volume ensured that the wafers were fully covered by the polymerization mixture. Three to six initiator-control agent modified wafers were positioned upright in the reaction vessel leaning against a central Teflon core at a 40° angle. The positioning of the wafer was designed to allow the site to be modified to be fully exposed to the reactants. A small silicon wafer was added to serve as a probe for thickness measurements. The initiator to monomer ratio was controlled by the amount of unbound initiator-control agent adduct in the polymerization reaction mixture. 2–5 mol % of free α-hydrido-nitroxide relative to non-surface-attached initiator-control agent adduct was added in order to control the propagation of monomer, as well as to substitute the TEMPO radical when TEMPO-containing surface-bound adduct was used.

The polymerizations were carried out in bulk or in 50 to 90 weight percent aqueous solutions. The water-soluble monomers were N,N-dimethylacrylamide and N-methyl-N-(2-hydroxyethyl)acrylamide; the latter provided hydroxyl functionality. The monomers were degassed by subjecting them to three freeze-pump-thaw cycles prior to use.

Size Exclusion Chromatography was performed using an automated "Accelerated GPC" system as described in U.S. patent application Ser. Nos. 09/285,363; 09/285,333; 09/285,335; or 09/285,392; each of which was filed on Apr. 2, 1999 and each of which is incorporated herein by reference. In the current apparatus, dimethylformamide containing 0.1% of trifluoroacetic acid at a flow rate of 2 ml/min. and a series of three 30 cm×7.5 mm linear columns calibrated using narrow polystyrene standards. The concentration of the polymer in the eluent was monitored using an evaporative light scattering detector. All of the molecular weight results obtained are relative to linear polystyrene standards. Thickness of the polymers was determined by ellipsometry measurements on the substrate surface. Thickness measurements were made using a Gaertner L116A rotating analyzer ellipsometer, which uses a HeNe laser ($\lambda$=632.8 nm) and an incidence angle of 70°.

Example 2

This example describes the preparation of a surface-bound copolymer having a target molecular weight of 50,000 daltons and 10 mol % of N-methyl-N-(2-hydroxyethyl)-acrylamide and 90 mol % N,N-dimethylacrylamide. Three fused silica wafers and one silicon wafer were used in this experiment. It was assumed that each surface contained hydroxyl functionalities typically in the picomole per square inch range. In order to add an initiator-control agent adduct to each surface hydroxyl functionality, $5 \times 10^{-4}$ mol of the trichlorosilyl-substituted initiator-control agent adduct was used per 2×3 in. wafer. Thus, the surface in this example is considered to have a fraction of chain initiator to the total number of reactive sites on the substrate surface of about 1.

Unbound initiator-control agent adduct (1.9 g) was dissolved in 291 mL of N,N-dimethylacrylamide, 37.9 g of N-methyl-N-(2-hydroxyethyl)acrylamide, 32 mg of α-hydridonitroxide, and 30 mL of water. The reaction vessel was sealed under argon and heated at 130° C. for 48 h. After the polymerization reaction, the wafers were placed in a DMF bath and heated at 50° C. for 12 h to remove non-covalently attached polymer chains, which were then analyzed by SEC, as described above. After washing with water and acetone, the wafers were air-dried and analyzed via ellipsometry to determine the thickness of the surface-bound copolymer film. SEC molecular weight ($M_w$, calibration versus polystyrene standards): 72,000; Film Thickness: 275 Å. Additionally, utilizing the method of determining grafting density described above (see, e.g., "Density Calculation"), the chain grafting density of the resulting polymer brush was found to be about 38 picomol/cm$^2$.

Example 3

This example describes the preparation of a surface-bound copolymer brush having a target molecular weight of 50,000 daltons and 25 mol % incorporation of N-methyl-N-(2-hydroxyethyl)acrylamide.

Substantially following Example 2, three fused silica wafers and one silicon wafer were modified with the trichlorosilyl-substituted initiator/control agent adduct to provide a fraction of chain initiator to the total number of surface functionalities of about 1. 1.9 g of unbound initiator-control agent adduct was dissolved in 232 mL of N,N-dimethylacrylamide, 90.8 g of N-methyl-N-(2-hydroxyethyl)acrylamide, 32 mg of α-hydridonitroxide, and 30 mL of water. The reaction vessel was sealed under argon and heated at 130° C. for 48 h. After the polymerization reaction, the wafers were placed in a DMF bath and heated at 50° C. for 12 h to remove non-covalently attached polymer that was then analyzed by SEC, as described above. After washing with water and acetone, the wafers were air dried and analyzed via ellipsometry to determine the thickness of the surface-bound copolymer film. SEC molecular weight (Mw, calibration versus polystyrene standards): 66,000; Film Thickness: 290 Å; and, Chain Density: ~44 picomol/cm$^2$.

Example 4

This example describes the preparation of a surface-bound copolymer having a target molecular weight of 10,000 daltons and 10 mol % incorporation of N-methyl-N-(2-hydroxyethyl)acrylamide.

Substantially following Example 2, three fused silica wafers and one silicon wafer were modified with the trichlorosilyl-substituted initiator-control agent adduct to provide a fraction of chain initiator to the total number of surface functionalities of about 1.9. 5 g of unbound initiator-control agent adduct was dissolved in 291 mL of N,N-dimethylacrylamide, 37.9 g of N-methyl-N-(2-hydroxyethyl)acrylamide, 160 mg of α-hydridonitroxide, and 30 mL of water. The reaction vessel was sealed under argon and heated at 130° C. for 48 h. After the polymerization reaction, the wafers were placed in a DMF bath and heated at 50 ° C. for 12 h to remove non-covalently attached polymer, which was then analyzed by SEC. After washing with water and acetone, the wafers were air dried and analyzed via ellipsometry to determine the thickness of the surface-bound copolymer film. SEC molecular weight (Mw, calibration versus polystyrene standards): 22,000; Film Thickness: 100 Å; and, Chain Density: ~46 picomol/cm$^2$.

Example 5

This example describes the preparation of a surface-bound copolymer brush having a target molecular weight of 10,000 daltons and 25 mol % incorporation of N-methyl-N-(2-hydroxyethyl)acrylamide.

Substantially following Example 2, three fused silica wafers and one silicon wafer were modified with the trichlorosilyl-substituted initiator-control agent adduct to provide a fraction of chain initiator to the total number of surface functionalities of about 1. 9.1 g of unbound initiator-control agent adduct was dissolved in 232 mL of N,N-dimethylacrylamide, 90.8 g of N-methyl-N-(2-hydroxyethyl)acrylamide, 160 mg of α-hydridonitroxide, and 30 mL of water. The reaction vessel was sealed under argon and heated at 130° C. for 48 h. After the polymerization reaction, the wafers were placed in a DMF bath and heated at 50° C. for 12 h to remove non-covalently attached polymer that was then analyzed by SEC, as described above. After washing with water and acetone, the wafers were air-dried and analyzed via ellipsometry to determine the thickness of the surface-bound copolymer film. SEC molecular weight (Mw, calibration versus polystyrene standards): 21,500; Film Thickness: 120 Å; and, Chain Density: ~56 picomol/cm$^2$.

Example 6

This example describes the preparation of a surface-bound copolymer brush having a target molecular weight of 50,000 daltons and 25 mol % incorporation of N-methyl-N-(2-hydroxyethyl)acrylamide.

Substantially following Example 2, three fused silica wafers and one silicon wafer were modified using 50 mol % of the trichlorosilyl-substituted initiator-control agent adduct and 50 mol % of the non-initiating benzylderivative (i.e., dummy molecule) to provide a fraction of chain initiator to the total number of surface functionalities of about 0.25. 1.9 g of unbound initiator-control agent adduct was dissolved in 232 mL of N,N-dimethylacrylamide, 90.8 g of N-methyl-N-(2-hydroxyethyl)acrylamide, 32 mg of α-hydridonitroxide, and 30 mL of water. The reaction vessel was sealed under argon and heated at 130° C. for 48 h. After the polymerization reaction, the wafers were placed in a DMF bath and heated at 50° C. for 12 h to remove non-covalently attached polymer that was then analyzed by SEC. After washing with water and acetone, the wafers were air dried and analyzed via ellipsometry to determine the thickness of the surface-bound copolymer film. GPC molecular weight (Mw, calibration versus polystyrene standards): 75,000; Film Thickness: 90 Å; and, Chain Density: ~12 picomol/cm$^2$.

Example 7

This example describes the preparation of a surface-bound copolymer brush having a target molecular weight of 50,000 daltons and 25 mol % incorporation of N-methyl-N-(2-hydroxyethyl)acrylamide.

Substantially following Example 2, three fused silica wafers and one silicon wafer were modified using 25 mol % of the trichlorosilyl-substituted initiator-control agent adduct and 75 mol % of the non-initiating benzyl derivative which provided a fraction of chain initiator to the total number of surface functionalities of about 0.25. 1.9 g of unbound initiator-control agent adduct was dissolved in 232 mL of N,N-dimethylacrylamide, 90.8 g of N-methyl-N-(2-hydroxyethyl)acrylamide, 32 mg of α-hydridonitroxide, and 30 mL of water. The reaction vessel was sealed under argon and heated at 130° C. for 48 h. After the polymerization reaction, the wafers were placed in a DMF bath and heated at 50° C. for 12 h to remove non-covalently attached polymer that was then analyzed by SEC. After washing with water and acetone, the wafers were air dried and analyzed via ellipsometry to determine the thickness of the surface-bound copolymer film. SEC molecular weight (Mw, calibration versus polystyrene standards): 68,000; Film Thickness: 55 Å; and, Chain Density: ~8 picomol cm$^2$.

Example 8

This example describes the preparation of a surface-bound copolymer brush having a target molecular weight of 100,000 daltons and 25 mol % incorporation of N-methyl-N-(2-hydroxyethyl)acrylamide.

Substantially following Example 2, three fused silica wafers and one silicon wafer were modified using 50 mol % of the trichlorosilyl-substituted initiator-control agent adduct and 50 mol % of the non-initiating benzyl derivative to provide a fraction of chain initiator to the total number of surface functionalities of about 0.5. 0.95 g of unbound initiator-control agent adduct was dissolved in 291 mL of N,N-dimethylacrylamide, 37.9 g of N-methyl-N-(2-hydroxyethyl)acrylamide, 16 mg of α-hydridonitroxide, and 30 mL of water. The reaction vessel was sealed under argon and heated at 130° C. for 48 h. After the polymerization reactions, the wafers were placed in a DMF bath and heated at 50° C. for 12 h to remove non-covalently attached polymer, which was analyzed by SEC. After washing with water and acetone, the wafers were air dried and analyzed via ellipsometry to determine the thickness of the surface-bound copolymer film. SEC molecular weight (Mw, calibration versus polystyrene standards): 125,000; Film Thickness: 100 Å; and, Chain Density: ~8 picomol/cm$^2$.

Example 9

This example describes the preparation of a surface-bound copolymer brush having a target molecular weight of 100,000 daltons and 25 mol % incorporation of N-methyl-N-(2-hydroxyethyl)acrylamide.

Substantially following Example 2, three fused silica wafers and one silicon wafer were modified using 25 mol % of the trichlorosilyl-substituted initiator-control agent adduct and 75 mol % of the non-initiating benzyl derivative to provide a fraction of chain initiator to the total number of surface functionalities of about 0.25. 0.95 g of unbound initiator-control agent adduct was dissolved in 291 mL of N,N-dimethylacrylamide, 37.9 g of N-methyl-N-(2-hydroxyethyl)acrylamide, 16 mg of a-hydridonitroxide, and 30 mL of water. The reaction vessel was sealed under argon and heated at 130° C. for 48 h. After the polymerization reaction, the wafers were placed in a DMF bath and heated at 50° C. for 12 h to remove non-covalently attached polymer that was then analyzed by SEC. After washing with water and acetone, the wafers were air-dried and analyzed via ellipsometry to determine the thickness of the surface-bound copolymer film. SEC molecular weight (Mw, calibration versus polystyrene standards): 1125,000; Film Thickness: 65 Å; and, Chain Density: ~5 picomol/cm$^2$.

Example 10

This example describes the preparation of a surface-bound copolymer brush having a target molecular weight of 50,000 daltons and 25 mol % incorporation of acrylic acid.

Substantially following Example 2, three fused silica wafers and one silicon wafer were modified using 75 mol % of the trichlorosilyl-substituted initiator-control agent adduct and 25 mol % of the non-initiating benzyl derivative which provided a fraction of chain initiator to the total number of surface functionalities of about 0.75. 2.1 g of unbound initiator-control agent adduct was dissolved in 268 g of N,N-dimethylacrylamide, 50.5 g of acrylic acid, 100 mg of α-hydridonitroxide, and 50 mL of water. The reaction vessel was sealed under argon and heated at 130° C. for 48 h. After the polymerization reaction, the wafers were placed in a DMF bath and heated at 50° C. for 12 h to remove non-covalently attached polymer that was then analyzed by SEC. After washing with water and acetone, the wafers were air dried and analyzed via ellipsometry to determine the thickness of the surface-bound copolymer film. SEC molecular weight (Mw, calibration versus polystyrene standards): 76,000.

Example 11

This example describes the preparation of a surface-bound copolymer brush having a target molecular weight of 50,000 daltons and 25 mol % incorporation of acrylic acid.

Substantially following Example 2, three fused silica wafers and one silicon wafer were modified using 50 mol % of the trichlorosilyl-substituted initiator-control agent adduct and 50 mol % of the non-initiating benzyl derivative which provided a fraction of chain initiator to the total number of surface functionalities of about 0.5. 2.1 g of unbound initiator-control agent adduct was dissolved in 268 g of N,N-dimethylacrylamide, 50.5 g of acrylic acid, 100 mg of a-hydridonitroxide, and 50 mL of water. The reaction vessel was sealed under argon and heated at 130° C. for 48 h. After the polymerization reaction, the wafers were placed in a DMF bath and heated at 50° C. for 12 h to remove non-covalently attached polymer that was then analyzed by SEC. After washing with water and acetone, the wafers were air dried and analyzed via ellipsometry to determine the thickness of the surface-bound copolymer film. SEC molecular weight (Mw, calibration versus polystyrene standards): 76,000.

Example 12

This example describes the preparation of a surface-bound copolymer brush having a target molecular weight of 50,000 daltons and 25 mol % incorporation of acrylic acid.

Substantially following Example 2, three fused silica wafers and one silicon wafer were modified using 25 mol % of the trichlorosilyl-substituted initiator-control agent adduct and 75 mol % of the non-initiating benzyl derivative which provided a fraction of chain initiator to the total number of surface functionalities of about 0.25. 2.1 g of unbound initiator-control agent adduct was dissolved in 268 g of N,N-dimethylacrylamide, 50.5 g of acrylic acid, 100 mg of α-hydridonitroxide, and 50 mL of water. The reaction vessel was sealed under argon and heated at 130° C. for 48 h. After the polymerization reaction, the wafers were placed in a DMF bath and heated at 50° C. for 12 h to remove non-covalently attached polymer that was then analyzed by SEC. After washing with water and acetone, the wafers were air dried and analyzed via ellipsometry to determine the thickness of the surface-bound copolymer film. SEC molecular weight (Mw, calibration versus polystyrene standards): 76,000.

Example 13

This example describes the preparation of a surface-bound copolymer brush having a target molecular weight of 50,000 daltons and 25 mol % incorporation of acrylic acid.

Substantially following Example 2, three fused silica wafers and one silicon wafer were modified using 12.5 mol % of the trichlorosilyl-substituted initiator-control agent adduct and 87.5 mol % of the non-initiating benzyl derivative which provided a fraction of chain initiator to the total number of surface functionalities of about 0.125. 2.1 g of unbound initiator-control agent adduct was dissolved in 268 g of N,N-dimethylacrylamide, 50.5 g of acrylic acid, 100 mg of α-hydridonitroxide, and 50 mL of water. The reaction vessel was sealed under argon and heated at 130° C. for 48 h. After the polymerization reaction, the wafers were placed in a DMF bath and heated at 50° C. for 12 h to remove non-covalently attached polymer that was then analyzed by SEC. After washing with water and acetone, the wafers were air dried and analyzed via ellipsometry to determine the thickness of the surface-bound copolymer film. SEC molecular weight (Mw, calibration versus polystyrene standards): 76,000.

Example 14

This example describes the preparation of a surface-bound copolymer brush having a target molecular weight of 80,000 daltons and 25 mol % incorporation of N-methyl-N-(2-hydroxyethyl)acrylamide.

Substantially following Example 2, three fused silica wafers and one silicon wafer were modified using 75 mol % of the trichlorosilyl-substituted initiator-control agent adduct and 25 mol % of the non-initiating benzyl derivative which provided a fraction of chain initiator to the total number of surface functionalities of about 0.75. 1.9 g of unbound initiator-control agent adduct was dissolved in 232 mL of N,N-dimethylacrylamide, 90.8 g of N-methyl-N-(2-hydroxyethyl)acrylamide, 32 mg of α-hydridonitroxide, and 30 mL of water. The reaction vessel was sealed under argon and heated at 130° C. for 48 h. After the polymerization reaction, the wafers were placed in a DMF bath and heated at 50° C. for 12 h to remove non-covalently attached polymer that was then analyzed by SEC. After washing with water and acetone, the wafers were air dried and analyzed via ellipsometry to determine the thickness of the surface-bound copolymer film. SEC molecular weight (Mw, calibration versus polystyrene standards): 88,000; Film Thickness: 175 Å; and, Chain Density: ~20 picomol/cm$^2$.

After preparation of the slides was complete, each was activated with carbonyldidimidazole as generally described above (see, e.g., "CDI activation of Hydroxyl-functionalized polymers on glass slides"). These were then treated with N-Dansylcystamine, and reductively cleaved to release the dye which was titrated with the HPLC technique as generally described above (see, e.g., Cleavable Dye Test). More specifically, attachment of the cleavable dye is achieved by submerging a brush in about 500 μM of a dye solution for about 12 hours and then washing the brush with anhydrous acetonitrile until the wash does not show any fluorescence as measured by HPLC with a fluorescence detector. The slides are then dried and stored in a dark, dry place. The attached dye molecules are then cleaved off the brush by reaction with 0.5 ml of 0.1 M dithiothreitol (DTT) or other reducing agents in acetonitrile in a cleaving chamber. The cleaved dye is then collected and quantified by HPLC analysis. Separation is performed by reverse-phase chromatrography using a Waters $C_{18}$ bonded reverse-phase column (150 mm×3.9 mm) with 4 μm particle size. A gradient method is run using water and acetonitrile (water/acetonitrile changing from 70/30 to 20/80 in 60 minutes), and a 5 μl injection of the cleaved solution. Fluorescence is measured with a Waters model 474 fluorescence detector using a 530 nm band-pass emission filter and 450 nm band-pass excitation filter in conjunction with a Xenon fluorescence lamp.

The density of functional groups accessible to this specific dye, N-Dansylcystamine, was $2.066 \times 10^3$ pmol/cm$^2$ (i.e., about 86% of the total number of —OH functional sites present on the surface). In terms of functional groups density, these results indicate a significant improvement over slides currently available commercially, which typically have a functional group density of about 25 pmol/cm$^2$.

Examples 15–17
Addition of Control Agent but not Initiator to Solution

Example 15

This example describes the preparation of a surface-bound copolymer brush with 25 mol % incorporation of N-methyl-N-(2-hydroxyethyl)acrylamide with control agent, but without sacrificial initiator-control agent adduct present in the reaction mixture.

Substantially following Example 2, three 1×1 cm silicon wafer were modified using 75 mol % of the trichlorosilyl-substituted initiator-control agent adduct and 25 mol % of the non-initiating benzyl derivative to provide a fraction of chain initiator to the total number of surface functionalities of about 0.75.32 g (0.32 moles) of N,N-dimethylacrylamide, 10.3 g (0.08 moles) of N-methyl-N-(2-hydroxyethyl) acrylamide and 1.864 mg ($8.5 \times 10^3$ mmoles, $2 \times 10^4$ M)of α-hydridonitroxide were placed in a 100 mL flask together with the silicon wafers. The reaction vessel was sealed under argon and heated at 130° C. for a total of 20 h. After 3, 6 and 20 h, respectively one of the wafers was removed and washed with acetone for 2 h, air dried and analyzed via ellipsometry to determine the thickness of the surface-bound copolymer film. Film Thickness: 3 h: 20 Å (mol. wt.~5236 g/mol); 6 h: 31 Å (mol. wt. ~8115 g/mol); 20 h: 46 Å (mol. wt. ~12,042 g/mol).

Example 16

This example describes the preparation of a surface-bound copolymer brush with 25 mol % incorporation of N-methyl-N-(2-hydroxyethyl)acrylamide with control agent, but without sacrificial initiator-control agent adduct present in the reaction mixture.

Substantially following Example 2, three 1×1 cm silicon wafer were modified using 75 mol % of the trichlorosilyl-substituted initiator-control agent adduct and 25 mol % of the non-initiating benzyl derivative to provide a fraction of chain initiator to the total number of surface functionalities of about 0.75. 32 g (0.32 moles) of N,N-dimethylacrylamide, 10.3 g (0.08 moles) of N-methyl-N-(2-hydroxyethyl)acrylamide and 18.64 mg ($8.5 \times 10^{-2}$ mmoles, $2 \times 10^{-3}$ M) of α-hydridonitroxide were placed in a 100 mL flask together with the silicon wafers. The reaction vessel was sealed under argon and heated at 130° C. for a total of 20 h. After 3, 6 and 20 h, respectively one of the wafers was removed and washed with acetone for 2 h, air dried and analyzed via ellipsometry to determine the thickness of the surface-bound copolymer film. Film Thickness: 3 h: 20 Å (mol. wt.~5236 g/mol); 6 h: 31 Å (mol. wt.~8115 g/mol); 20h: 39 Å (mol. wt.~10,209 g/mol).

Example 17

This example describes the preparation of a surface-bound copolymer brush with 25 mol % incorporation of N-methyl-N-(2-hydroxyethyl)acrylamide with control agent, but without sacrificial initiator-control agent adduct present in the reaction mixture.

Substantially following Example 2, three 1×1 cm silicon wafer were modified using 75 mol % of the trichlorosilyl-substituted initiator-control agent adduct and 25 mol % of the non-initiating benzyl derivative to provide a fraction of chain initiator to the total number of surface functionalities of about 0.75. 32 g (0.32 moles) of N,N-dimethylacrylamide, 10.3 g (0.08 moles) of N-methyl-N-(2-hydroxyethyl)acrylamide and 0.1864 mg (8.5×10$^{-4}$ mmoles, 2×10$^{-5}$ M) of α-hydridonitroxide were placed in a 100 mL flask together with the silicon wafers. The reaction vessel was sealed under argon and heated at 130° C. for a total of 20 h. After 3, 6 and 20 h, respectively one of the wafers was removed and washed with acetone for 2 h, air dried and analyzed via ellipsometry to determine the thickness of the surface-bound copolymer film. Film Thickness: 3 h: 16 Å (mol. wt.~4188 g/mol); 6 h: 22 Å (mol. wt.~5759 g/mol); 20 h: 32 Å (mol. wt.~8377 g/mol).

Example 18

Addition of Control Agent but not Initiator to Solution

This example describes an approach similar to Examples 15–17, above, in than no free initiator is present in the polymerization mixture. However, unlike those examples, here the iniferter technique is employed in place of the nitroxide-mediated, controlled polymerization.

1-Synthesis of the initiator p-(Chloromethyl)phenyltrimethoxysilane (0.4 g, 1.62 mmol) and N,N-diethyl dithiocarbamate sodium salt (0.370 mg, 2.17 mmol) were each dissolved separately in 3 mL of dry THF. The N,N-diethyl dithiocarbamate solution was added slowly to the p-(Chloromethyl)-phenyltrimethoxysilane solution via a syringe. The solution was stirred for 7 h at room temperature. A white precipitate was formed almost immediately (NaCl) and, during the reaction period, the solution became more yellow. The mixture was then filtered and the crude product was used without further purification.

2-Surface Grafting of the Initiator

The solution of initiator (0.2–0.3 M in dry THF or dry toluene) was directly used on glass wafers as well as on silicon wafers, prepared as described above with respect to Examples 2–14. Typically each wafer is immersed one after the other in 5 ml of solution for up to about 2 to 3 days at room temperature, to allow the initiator to react with the surface silanol groups. The surfaces were covered by 2–3 mm of solution each time. Then, the wafers were washed with DMF and dried under a prepurified N$_2$ flow at room temperature.

3-Synthesis of Polymer Brushes

Reactions were performed in a glove box with low amount of oxygen (about 1 ppm or less). Each silicon wafer was immersed in distilled dimethylacrylamide (1 ml). As indicated by the table below, various concentrations of the control agent, tetraethylthiuram disulfide (TEDS) were used in each preparation. The surfaces were then placed about 10 cm from a 365–366 nm UV lamp and irradiated for the required time at room temperature. After polymerization, the samples were immersed in 50 ml of dichloromethane overnight to remove homopolymers that may have formed in solution. Finally, the surfaces were dried under a prepurified N$_2$ flow at room temperature. The surfaces were then characterized by ellipsometry measurements.

| Control agent (TEDS) | Irradiation time | Monomer conversion in solution (%) | Polymer thickness (Angstroms) |
|---|---|---|---|
| none(*) | 5 mn | 1 | 0 |
| None | 5 mn | 1 | 41 |
| None | 50 mn | 3 | 333 |
| 0.001 M/L | 50 mn | 5.5 | 158 |
| 0.01 M/L | 780 mn | 80 | 58 |

(*): reference sample with no bound initiator

These experiments show that no polymerization occurs on the wafer, and virtually no polymer is formed in solution when no initiator is grafted on the surface. It also shows a steady increase of the polymer thickness as the irradiation time is prolonged. The addition of control agent actually slows down the growth and provides additional control.

Example 19

Performance Study

The polymer substrate can be evaluated as a biosensor based on the ability of the polymer-bound probes to capture biomolecules (e.g. target) from solution. This performance can be evaluated in terms of the overall efficiency and selectivity of target binding, e.g., by evaluating (1) the total amount of target bound, (2) the ability to detect and quantify the amount of specific target in solution, (3) the ability to detect and quantify the amount of specific target within a complex solution, (4) the ability to enhance the dynamic range through detection of very low concentrations of target, or (5) the combined ability to detect these signals above the background and noise of the system.

This example illustrates a method for testing the performance of the polymers as a substrate for oligonucleotide probe attachment and subsequent DNA target hybridization. In this example, oligonucleotide probes of 50-bases (50 mers) were immobilized to polymer substrates of varying fractions of surface bound chain initiator to the total number of surface functionalities (the fraction ranging from 0.125 to 0.75). Probe concentrations within a 0–200 micromolar range were used to test the loading (chemical attachment) efficiency of these probes to the activated polymer substrates. Complex (gene expression) target solutions were then applied to the probe arrays, where the solution included "spiked" picomolar concentrations of particular targets to test the efficiency of capturing/sampling very low target populations within a complex hybridization solution. The results are illustrated in FIG. 7.

All of the substrates demonstrated a loading capacity that mimicked solution hybridization, suggesting that the loading is not significantly limited or slowed by surface effects or mesh-hindered diffusion. For the range of polymer densities tested, the polymer designed with 0.25 initiator fraction reproducibly demonstrated the best performance in loading capacity for the 50-base probes. This result is consistent with the ~40 Å mesh-size analysis of the polymer architecture, suggesting that the polymer substrate can be tailored to achieve an optimal loading capacity if the mesh is roughly equivalent to half the radius of gyration of the intended probes.

The same polymer (with 0.25 initiator fraction) also reproducibly demonstrated the best performance in target hybridization, presumably due to the increased probe density and solution-like binding performance. For the polymers designed with 0.25 to 0.75 initiator fraction, these substrates significantly increased the dynamic range of the hybridization performance, as shown by the ability to hybridize and recognize ("call") more of the targets present at very low concentrations. In some cases, these substrates accurately called 100% of the targets in the gene expression solution.

It is to be understood that the above description is intended to be illustrative and not restrictive. Many embodiments will be apparent to those of skill in the art upon reading the above description. The scope of the invention should therefore be determined not with reference to the above description, but should instead be determined with reference to the appended claims, along with the full scope of equivalents to which such claims are entitled.

The disclosures of all articles, patents and references, including patent applications and publications, are incorporated herein by reference for all purposes.

Other embodiments are within the following claims.

What is claimed is:

1. A method of preparing a sensor for detecting a biological molecule in an aqueous sample, the method comprising:

bonding an iniferter initiator to a substrate surface at one or more points to form a derivatized surface, said surface-bound iniferter initiator having the formula:

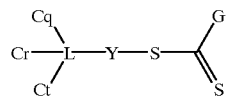

wherein C is a moiety on the surface of the substrate; L is a linker group capable of bonding to at least one C moiety; q, r and t are independently 0 or 1, provided the sum of q+r+t is at least 1; Y is a residue capable of initiating free radical polymerization upon homolytic cleavage of the Y—S bond; S is sulfur; and, G is a nitrogen or an oxygen heteroatom;

contacting said derivatized surface with a composition comprising a water-soluble or water-dispersible free radically polymerizable monomer mixture under reaction conditions to form bound polymer chains comprising a water-dispersible segment having a weight average molecular weight of at least about 1000 grams per mole, wherein (i) the mixture comprises a monomer that has one or more functionalized sites thereon for reaction with a probe selective for the biological molecule and a monomer that does not have a functionalized site for reaction with said probe, and (ii) the mixture comprises an acrylamide-based monomer and at least 1 other monomer; and bonding the probe to the bound polymer chains through the functionalized sites.

2. The method according to claim 1 wherein the surface bound iniferter initiator has the formula:

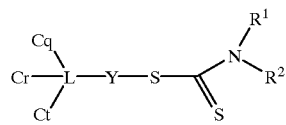

wherein N is nitrogen, and $R^1$ and $R^2$ are independently selected from hydrocarbyl and substituted hydrocarbyl.

3. The method according to claim 2 wherein said surface bound iniferter initiator has the formula:

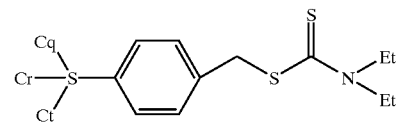

wherein Et is ethyl.

4. The method according to claim 3 wherein C is derived from a hydroxyl group.

5. The method according to claim 3 wherein q=1, r=1 and t=0.

6. The method according to claim 3 wherein q=1, r=1 and t=1.

7. The method according to claim 1 further comprising bonding spacer molecules to said substrate surface at one or more points to form the derivatized surface, said one or more points being different from the points at which said bound polymer chains are formed to space said bound polymer chains apart from each other, wherein the ratio of polymer chains to the sum of polymer chains and spacer molecules is about 0.75:1.

8. The method according to claim 1 wherein the acrylamide-based monomer has the formula:

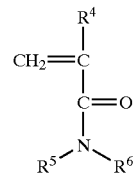

wherein $R^4$ is H or an alkyl group, $R^5$ is methyl and $R^6$ is methyl.

9. The method according to claim 8 wherein the monomer is N,N-dimethylacrylamide.

10. The method according to claim 1 further comprising separating unbound polymer after said derivatized surface is contacted with a composition comprising the monomer mixture to form polymer chains.

11. The method according to claim 10 wherein the monomer mixture additionally comprises an unbound iniferter initiator.

12. The method according to claim 1, wherein the monomer mixture comprises about 10% to about 90% of the monomer having said functionalized sites for reaction with said probe, based on the total mass of monomer in said mixture.

13. The method according to claim 1 wherein the monomer mixture comprises about 15% to about 50% of the monomer having said functionalized sites for reaction with said probe, based on the total mass of monomer in said mixture.

14. The method according to claim 1 wherein the one or more functionalized sites on said functionalized monomer are in their a active state for reaction with said probe.

* * * * *

UNITED STATES PATENT AND TRADEMARK OFFICE
CERTIFICATE OF CORRECTION

PATENT NO. : 6,833,276 B2
DATED : December 21, 2004
INVENTOR(S) : Klaerner et al.

It is certified that error appears in the above-identified patent and that said Letters Patent is hereby corrected as shown below:

Column 54,
Line 1, replace the formula with:

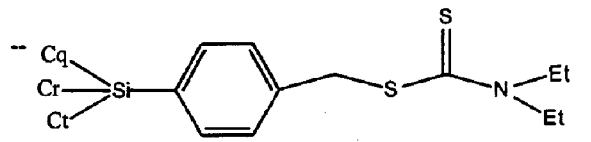

Line 61, delete "a" between "their" and "active"

Signed and Sealed this

Twelfth Day of April, 2005

JON W. DUDAS
*Director of the United States Patent and Trademark Office*